(12) United States Patent
Thormann et al.

(10) Patent No.: US 7,741,354 B2
(45) Date of Patent: Jun. 22, 2010

(54) INHIBITORS OF GLUTAMINYL CYCLASE

(75) Inventors: Michael Thormann, Martinsried (DE); Michael Altmstetter, Martinsried (DE); Andreas Treml, Martinsried (DE); Ulrich Heiser, Halle/Saale (DE); Mirko Buchholz, Halle/Saale (DE)

(73) Assignee: Probiodrug AG, Halle-Saale (DE)

( * ) Notice: Subject to any disclaimer, the term of this patent is extended or adjusted under 35 U.S.C. 154(b) by 117 days.

(21) Appl. No.: 11/937,159

(22) Filed: Nov. 8, 2007

(65) Prior Publication Data
US 2008/0207715 A1 Aug. 28, 2008

Related U.S. Application Data

(60) Provisional application No. 60/864,990, filed on Nov. 9, 2006.

(51) Int. Cl.
*A61K 31/41* (2006.01)
*C07D 257/00* (2006.01)
(52) U.S. Cl. .................. 514/381; 514/389; 548/250
(58) Field of Classification Search .............. 514/359, 514/381; 548/250
See application file for complete search history.

(56) References Cited

U.S. PATENT DOCUMENTS

| | | | |
|---|---|---|---|
| 5,721,234 | A | 2/1998 | Bigge et al. |
| 7,304,086 | B2 | 12/2007 | Schilling |
| 7,371,871 | B2 | 5/2008 | Schilling |
| 7,381,537 | B2 | 6/2008 | Demuth |
| 7,462,599 | B2 | 12/2008 | Schilling |
| 2005/0137142 | A1 | 6/2005 | Schultz |
| 2005/0171112 | A1 | 8/2005 | Schultz |
| 2006/0100253 | A1 | 5/2006 | Niestroj |
| 2007/0191366 | A1 | 8/2007 | Hoffmann |
| 2008/0153892 | A1 | 6/2008 | Schilling |
| 2008/0214620 | A1 | 9/2008 | Heiser |
| 2008/0249083 | A1 | 10/2008 | Schilling |
| 2008/0286810 | A1 | 11/2008 | Demuth |
| 2009/0018087 | A1 | 1/2009 | Schilling |
| 2009/0068699 | A1 | 3/2009 | Schilling |
| 2009/0149394 | A1 | 6/2009 | Schilling |

OTHER PUBLICATIONS

Mayer, et al., Tet. Lett., vol. 46(43), pp. 7393-7396, esp. p. 7395, published Sep. 9, 2005.*
Mayer, et al., Tet. Lett., vol. 46(43), pp. 7393-7396, esp. p. 7393.*
CAS 296898356.
CAS 499974673.
CAS 896058450.
CAS 896058643.
CAS 896060869.
Barreca ML, et al., Computational strategies in discovering novel non-nucleoside inhibitors of HIV-1 RT, J. Med. Chem., 2005, p. 3433-7, vol. 48(9).
Bateman RC, et al., Evidence for essential histidines in human pituitary glutaminyl cyclase, Biochem., 2001, p. 11246-50, vol. 40(37).
Bockers TM, et al., Glutaminyl-cyclase expression in the bovine/porcine hypothalamus and pituitary, J. Neuroendocrinol., 1995, p. 445-53, vol. 7(6).
Busby WH, et al., An enzyme(s) that converts glutaminyl-peptides into pyroglutamyl-peptides. Presence in pituitary, brain, adrenal medulla, and lymphocytes, J. Biol. Chem., 1987, p. 8532-6, vol. 262(18).

(Continued)

*Primary Examiner*—Susannah Chung
(74) *Attorney, Agent, or Firm*—Sonnenschein Nath & Rosenthal LLP

(57) ABSTRACT

The present invention relates to compounds of formula (I), combinations and uses thereof for disease therapy, (I)

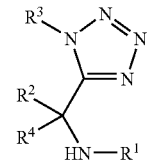

wherein:
$R^1$ represents heteroaryl, -carbocyclyl-heteroaryl, -alkenyl-heteroaryl or -alkylheteroaryl;
$R^2$ represents alkyl, which may optionally be substituted by one or more groups selected from amino, halogen, hydroxyl, -alkoxy, -thioalkyl, —C(O)O-alkyl and —C(O)OH; carbocyclyl, which may optionally be substituted by one or more groups selected from alkyl, haloalkyl, amino, halogen, hydroxyl, alkoxy-, -thioalkyl, —C(O)O-alkyl and —C(O)OH; alkenyl; alkynyl; -alkyl-aryl; -alkyl-heteroaryl; -alkyl-heterocyclyl; -alkyl-carbocyclyl; -aryl-heteroaryl; -heteroaryl-aryl; -heteroaryl-heteroaryl; -aryl-aryl; -aryl (monocyclic or bicyclic); heteroaryl (monocyclic or bicyclic); heterocyclyl; or $R^2$ together with $R^4$ may form a carbocyclyl group optionally substituted by one or more alkyl groups;
$R^3$ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)$_2$, -alkyl(heteroaryl)$_2$, -alkyl(aryl)(heteroaryl), -alkyl-heteroaryl; -alkyl-heterocyclyl which heterocyclyl group may optionally be substituted by one or more groups selected from alkyl, hydroxy and oxo ; -alkyl-carbocyclyl; -aryl-heteroaryl; -heteroaryl-aryl; -aryl-aryl; -aryl-O-aryl, -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.
$R^4$ represents H or alkyl.

23 Claims, No Drawings

OTHER PUBLICATIONS

Consalvo AP, et al., A rapid fluorometric assay for N-terminal glutaminyl cyclase activity using high-performance liquid chromatography, Anal. Biochem., 1998, p. 131-8, vol. 175(1).

Dahl SW, et al., Carica papaya glutamine cyclotransferase belongs to a novel plant enzyme subfamily: cloning and characterization of the recombinant enzyme, Protein Expr. Purif., 2000, p. 27-36, vol. 20(1).

Fischer WH and Spiess J, Identification of a mammalian glutaminyl cyclase converting glutaminyl into pyroglutamyl peptides, PNAS, 1987, p. 3628-31, vol. 84(11).

Messer M, Enzymatic cyclization of L-glutamine and L-glutaminyl peptides, Nature, 1963, p. 1299, vol. 197(4874).

Mironov MA, et al., Ugi reaction with isocyanoindoles, J. Org. Chem., 2004, p. 847-53, vol. 40(6).

Moussaoui A, et al., Revisiting the enzymes stored in the laticifers of Carica papaya in the context of their possible participation in the plant defence mechanism, Cell. Mol. Life Sci., 2001, p. 556-70, vol. 58(4).

Pohl T, et al., Primary structure and functional expression of a glutaminyl cyclase, PNAS, 1991, p. 10059-63, vol. 88(22).

Ugi I, The alpha-addition of immonium ions and anions to isonitriles accompanied by secondary reactions, Agnew. Chem. Internat. Edit., 1962, p. 8-21, vol. 1(1).

* cited by examiner

```
                        SEQUENCE LISTING

<160> NUMBER OF SEQ ID NOS: 20

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
```

```
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 5

Gln Gly Pro Trp Leu Glu Glu Glu Glu Ala Tyr Gly Trp Met Asp
1               5                   10                  15

Phe

<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
```

<213> ORGANISM: Homo sapiens

<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
        50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
65                  70                  75

<210> SEQ ID NO 10
<211> LENGTH: 76
<212> TYPE: PRT
<213> ORGANISM: Homo sapiens

<400> SEQUENCE: 10

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr
65                  70                  75

<210> SEQ ID NO 11
<211> LENGTH: 68
<212> TYPE: PRT
<213> ORGANISM: Homo sapiens

<400> SEQUENCE: 11

Gln Val Gly Thr Asn Lys Glu Leu Cys Cys Leu Val Tyr Thr Ser Trp

```
                1               5                  10                 15
Gln Ile Pro Gln Lys Phe Ile Val Asp Tyr Ser Glu Thr Ser Pro Gln
                20                 25                 30

Cys Pro Lys Pro Gly Val Ile Leu Leu Thr Lys Arg Gly Arg Gln Ile
                35                 40                 45

Cys Ala Asp Pro Asn Lys Lys Trp Val Gln Lys Tyr Ile Ser Asp Leu
                50                 55                 60

Lys Leu Asn Ala
65

<210> SEQ ID NO 12
<211> LENGTH: 373
<212> TYPE: PRT
<213> ORGANISM: Homo sapiens

<400> SEQUENCE: 12

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
                35                  40                  45

Phe Cys Ala Asp Pro Lys Glu Gln Trp Val Lys Asp Ala Met Gln His
                50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
                100                 105                 110

Ser Leu Glu Pro Thr Pro Ser Ser Gln Glu Ala Gln Arg Ala Leu Gly
                115                 120                 125

Thr Ser Pro Glu Leu Pro Thr Gly Val Thr Gly Ser Ser Gly Thr Arg
                130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
                180                 185                 190

Glu Ala Pro Ser Thr Gln Asp Pro Ser Thr Gln Ala Ser Thr Ala Ser
                195                 200                 205

Ser Pro Ala Pro Glu Glu Asn Ala Pro Ser Glu Gly Gln Arg Val Trp
                210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Val Pro Val Ser Ser Glu Gly Thr
                260                 265                 270

Pro Ser Arg Glu Pro Val Ala Ser Gly Ser Trp Thr Pro Lys Ala Glu
                275                 280                 285

Glu Pro Ile His Ala Thr Met Asp Pro Gln Arg Leu Gly Val Leu Ile
                290                 295                 300
```

```
Thr Pro Val Pro Asp Ala Gln Ala Ala Thr Arg Arg Gln Ala Val Gly
305                 310                 315                 320

Leu Leu Ala Phe Leu Gly Leu Phe Cys Leu Gly Val Ala Met Phe
            325                 330                 335

Thr Tyr Gln Ser Leu Gln Gly Cys Pro Arg Lys Met Ala Gly Glu Met
                340                 345                 350

Ala Glu Gly Leu Arg Tyr Ile Pro Arg Ser Cys Gly Ser Asn Ser Tyr
            355                 360                 365

Val Leu Val Pro Val
        370

<210> SEQ ID NO 13
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
50                  55                  60

Lys His Leu Asp Lys Lys Thr Gln Thr Pro Lys Leu
65                  70                  75

<210> SEQ ID NO 14
<211> LENGTH: 33
<212> TYPE: PRT
<213> ORGANISM: Homo sapiens

<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
```

-continued

```
                20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 19
<211> LENGTH: 34
<212> TYPE: PRT
<213> ORGANISM: Artificial sequence
<220> FEATURE:
<223> OTHER INFORMATION: Synthetic peptide

<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```

INHIBITORS OF GLUTAMINYL CYCLASE

CROSS REFERENCE TO RELATED APPLICATIONS

The present application contains subject matter related to U.S. Provisional Application No. 60/864,990 filed on Nov. 9, 2006, the entire contents of which being incorporated herein by reference.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci U S A 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (E I Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous. The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

First inhibitors of QC are described in WO 2004/098625, WO 2004/098591, WO 2005/039548 and WO 2005/075436.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

DEFINITIONS

The terms "$k_i$" or "$K_i$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins were the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-D-homoglutamine to a cyclic pyro-homoglutamine derivative under liberation of ammonia. See therefore schemes 1 and 2.

Scheme 1:
Cyclization of glutamine by QC

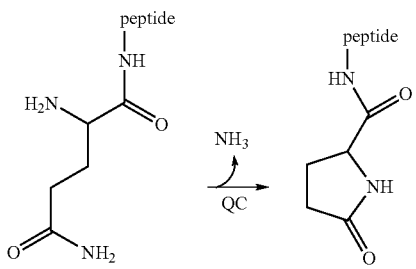

Scheme 2:
Cyclization of L-homoglutamine by QC

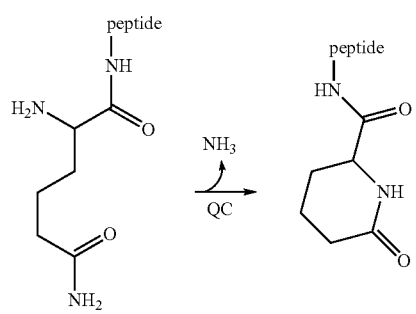

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

Scheme 3:
N-terminal cyclization of uncharged glutamyl peptides by QC (EC)

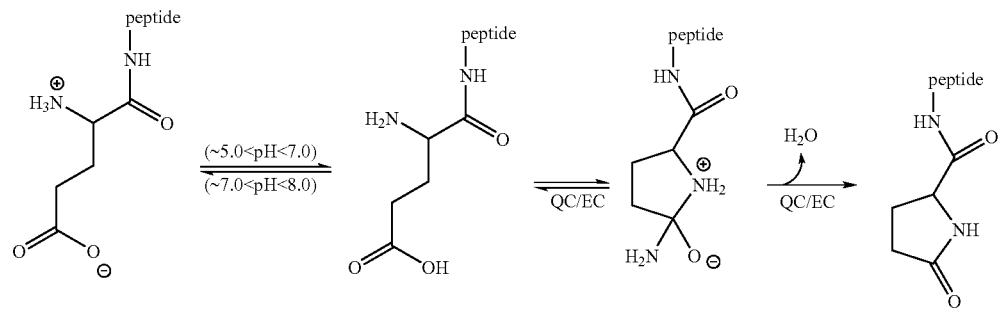

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an $IC_{50}$ for QC inhibition of 10 μM or less, more preferably of 1 μM or less, even more preferably of 0.1 μM or less or 0.01 μM or less, or most preferably 0.001 μM or less. Indeed, inhibitors with $K_i$ values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include vinyl (i.e. ethenyl), propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include ethynyl, propynyl and butynyl.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocylic groups include monocyclic, bicyclic, and tricyclic ring systems, in particular monocyclic and bicyclic ring systems. Other carbocyclyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings), but may also comprise partially or fully unsaturated rings. An example of a typical aryl group with one aromatic ring is phenyl. Examples of aromatic groups with two aromatic rings include naphthyl. Examples of aryl groups which contain partially or fully unsaturated rings include pentalene, indene and indane.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups include pyridine (e.g. pyridin-2-yl, pyridin-3-yl or pyridin-4-yl), pyrimidine, pyrrole, furan, thiophene, oxazole, pyrazole, imidazole (e.g. imidazol-1-yl, imidazol-2-yl or imidazol-4-yl), thiazole, isoxazole, pyrazole (e.g. pyrazol-3-yl), triazole (e.g. 1,2,3-triazole or 1,2,4-triazole), tetrazole, pyridazine, pyrazine and isothiazole.

Exemplary bicyclic heteroaryl groups include quinoline, benzothiophene, indole (e.g. 1H-indol-6-yl), benzimidazole, indazole, purine, chromene, benzodioxolane, benzodioxane (e.g. 2,3-dihydro-benzo[1,4]dioxin-6-yl) and benzodioxepine.

The aforementioned aryl and heteroaryl groups may, where appropriate, optionally be substituted by one or more (e.g. 1, 2 or 3, suitably 1 or 2) monovalent or multivalent functional groups. Suitable substituent groups include alkyl, alkenyl, alkynyl, haloalkyl, -thioalkyl (e.g. -thiomethyl), —$SO_2$alkyl (e.g. $SO_2Me$), alkoxy- (e.g. OMe), cycloalkyl, —$SO_2$cycloalkyl, alkenyloxy-, alkynyloxy-, —C(O)-alkyl (e.g. COMe), alkoxyalkyl-, nitro, halogen (e.g. fluoro, chloro and bromo), cyano, hydroxyl, oxo, —C(O)OH, —C(O)Oalkyl (e.g. —C(O)OMe), —$NH_2$, —NHalkyl (e.g. —NHMe), —N(alkyl)$_2$ (e.g. dimethylamino-), —C(O)N(alkyl)$_2$, —C(O)$NH_2$ and —C(O)NH(alkyl). More typically, substituents will be selected from alkyl (e.g. Me), fluoroalkyl (e.g. $CF_3$), alkoxy (e.g. OMe), halogen and hydroxy. Further suitable substituents include —SOalkyl (e.g. SOMe) and —SOcycloalkyl. Another suitable substituent for a heteroaryl group is —C(NH)$NH_2$.

Examples of substituted aryl groups therefore include fluorophenyl- (e.g. 4-fluoro-phenyl- or 3-fluoro-phenyl-), pentafluoro-phenyl-, 4-hydroxyphenyl-, 3-nitro-phenyl-, 4-(trifluoromethyl)-phenyl- and 4-anilinyl- groups. Exemplary substituted monocyclic heteroaryl groups include methylfuranyl-.

Exemplary substituted bicyclic heteroaryl groups include chromen-4-one, chromen-2-one and methylbenzothiophenyl.

The expression "-alkylaryl", unless specifically limited, denotes an aryl residue which is connected via an alkylene moiety e.g. a $C_{1-4}$alkylene moiety. Examples of -alkylaryl include: -methylaryl and -ethylaryl (e.g. 1-arylethyl- or 2-arylethyl-); or phenylalkyl-, which may be optionally substituted. Specific examples of -alkylaryl functions include: phenylmethyl- (i.e. benzyl), phenylethyl- (e.g. 2-phenyleth-1-yl or 1-phenyl-eth-1-yl), p-tolyl-methyl-, (p-tolyl)-ethyl-, (m-tolyl)-methyl-, (m-tolyl)-ethyl-, (o-tolyl)-methyl-, (o-tolyl)-ethyl-, 2-(4-ethyl-phenyl)-eth-1-yl-, (2,3-dimethyl-phenyl)-methyl-, (2,4-dimethyl-phenyl)-methyl-, (2,5-dimethyl-phenyl)-methyl-, (2,6-dimethyl-phenyl)-methyl-, (3,4-dimethyl-phenyl)-methyl-, (3,5-dimethyl-phenyl)-methyl-, (2,4,6-trimethyl-phenyl)-methyl-, (2,3-dimethyl-phenyl)-ethyl-, (2,4-dimethyl-phenyl)-ethyl-, (2,5-dimethyl-phenyl)-ethyl-, (2,6-dimethyl-phenyl)-ethyl-, (3,4-dimethyl-phenyl)-ethyl-, (3,5-dimethyl-phenyl)-ethyl-, (2,4,6-trimethyl-phenyl)-ethyl-, (2-ethyl-phenyl)-methyl-, (3-ethyl-phenyl)-methyl-, (4-ethyl-phenyl)-methyl-, (2-ethyl-phenyl)-ethyl-, (3-ethyl-phenyl)-ethyl-, (4-ethyl-phenyl)-ethyl-, 2-fluorobenzyl, (1-methyl-2-fluoro-phen-6-yl)-methyl-, (1-methyl-2-fluoro-phen-4-yl)-methyl-, (1-methyl-2-fluoro-phen-6-yl)-ethyl-, (1-methyl-2-fluoro-phen-4-yl)-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, dihydronaphthalinyl-methyl-, dihydronaphthalinyl-ethyl-, or (4-cyclohexyl)-phenyl-methyl-, (4-cyclohexyl)-phenyl-ethyl-.

The expression "-alkylheteroaryl", unless specifically limited, denotes a heteroaryl residue which is connected via an alkylene moiety e.g. a $C_{1-4}$alkylene moiety. Examples of -alkylheteroaryl include -methylheteroaryl and -ethylheteroaryl (e.g. 1-heteroarylethyl- and 2-heteroarylethyl-). Specific examples of -alkylheteroaryl groups include pyridinyl-methyl-, N-methyl-pyrrol-2-methyl-, N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

The expression "-alkyl(aryl)$_2$", unless specifically limited, denotes an alkyl group (e.g. a $C_{1-4}$alkyl group) which is substituted by two aryl residues (e.g. monocyclic aryl), for example diphenylmethyl-.

The term "halogen" or "halo" comprises fluorine (F), chlorine (Cl) and bromine (Br).

The term "amino" refers to a group having amine functionality for example primary amine (—NH$_2$), secondary amine (e.g. —NHalkyl, for example —NHMe) or tertiary amine (e.g. —N(alkyl)$_2$, for example —NMe$_2$, —NEt$_2$).

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution.

The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt or solvate is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxalacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for Example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for Example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

SUMMARY OF THE INVENTION

According to the invention there are provided compounds of formula (I),

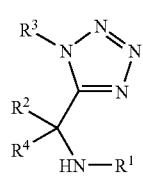

(I)

including pharmaceutically acceptable salts thereof, including all stereoisomers and polymorphs, wherein:

$R^1$ represents heteroaryl, -carbocyclyl-heteroaryl, -alkenylheteroaryl or -alkylheteroaryl;

$R^2$ represents alkyl, which may optionally be substituted by one or more groups selected from amino, halogen, hydroxyl, -alkoxy, -thioalkyl, —C(O)O-alkyl and —C(O)OH; carbocyclyl, which may optionally be substituted by one or more groups selected from alkyl, haloalkyl, amino, halogen, hydroxyl, alkoxy-, -thioalkyl, —C(O)O-alkyl and —C(O)OH; alkenyl; alkynyl; -alkyl-aryl; -alkyl-heteroaryl; -alkyl-heterocyclyl; -alkyl-carbocyclyl; -aryl-heteroaryl; -heteroaryl-aryl; -heteroaryl-heteroaryl; -aryl-aryl; -aryl (monocyclic or bicyclic); heteroaryl (monocyclic or bicyclic); heterocyclyl; or $R^2$ together with $R^4$ may form a carbocyclyl group optionally substituted by one or more alkyl groups;

$R^3$ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)$_2$, -alkyl(heteroaryl)$_2$, -alkyl(aryl)(heteroaryl), -alkyl-heteroaryl; -alkyl-heterocyclyl which heterocyclyl group may optionally be substituted by one or more groups selected from alkyl, hydroxy and oxo ; -alkyl-carbocyclyl; -aryl-heteroaryl; -heteroaryl-aryl; -aryl-aryl; -aryl-O-aryl; -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.

$R^4$ represents H or alkyl.

The compounds of the present invention act as inhibitors of glutaminyl cyclase (QC, EC 2.3.2.5) and QC-like enzymes.

DETAILED DESCRIPTION OF THE INVENTION

According to the invention there are provided compounds of formula (I),

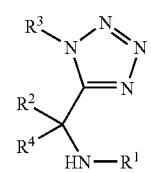

(I)

including pharmaceutically acceptable salts thereof, including all stereoisomers and polymorphs, wherein:

$R^1$ represents heteroaryl, -carbocyclyl-heteroaryl, -alkenylheteroaryl or -alkylheteroaryl;

$R^2$ represents alkyl, which may optionally be substituted by one or more groups selected from amino, halogen, hydroxyl, -alkoxy, -thioalkyl, —C(O)O-alkyl and —C(O)OH; carbocyclyl, which may optionally be substituted by one or more groups selected from alkyl, haloalkyl, amino, halogen, hydroxyl, alkoxy-, -thioalkyl, —C(O)O-alkyl and —C(O)OH; alkenyl; alkynyl; -alkyl-aryl; -alkyl-heteroaryl; -alkyl-heterocyclyl; -alkyl-carbocyclyl; -aryl-heteroaryl; -heteroaryl-aryl; -heteroaryl-heteroaryl; -aryl-aryl; -aryl (monocyclic or bicyclic); heteroaryl (monocyclic or bicyclic); heterocyclyl; or R² together with R⁴ may form a carbocyclyl group optionally substituted by one or more alkyl groups;

R³ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)₂, -alkyl(heteroaryl)₂, -alkyl(aryl)(heteroaryl), -alkyl-heteroaryl; -alkyl-heterocyclyl which heterocyclyl group may optionally be substituted by one or more groups selected from alkyl, hydroxy and oxo; -alkyl-carbocyclyl; -aryl-heteroaryl; -heteroaryl-aryl; -aryl-aryl; -aryl-O-aryl; -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.

R⁴ represents H or alkyl.

In one embodiment, the following compounds are excluded from the scope of formula (I):

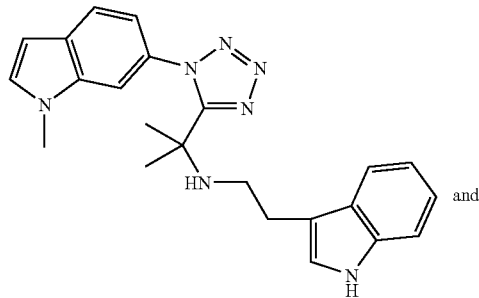

and

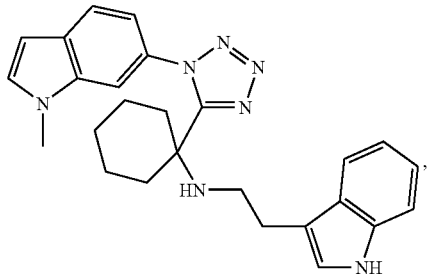

which are disclosed in Russian Journal of Organic Chemistry (Mironov);

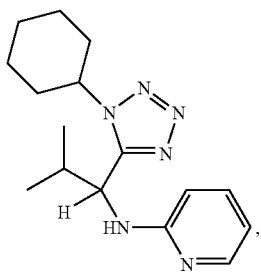

which is disclosed in Angewandte Chemie International Edition, 1962, p 8-21 (Ivar Ugi et al);

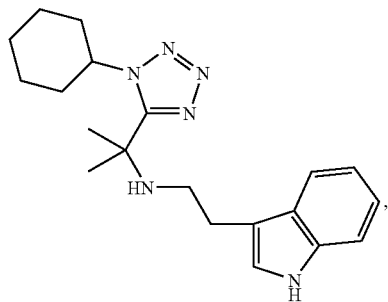

which is disclosed by CAS under Reference 896060-86-9;

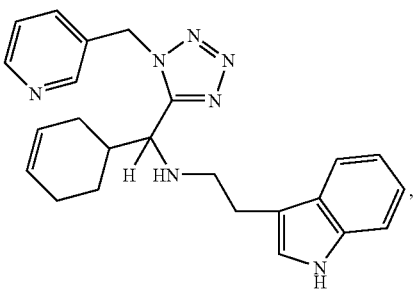

which is disclosed by CAS under Reference 896058-64-3;

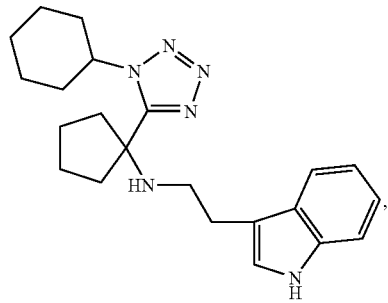

which is disclosed by CAS under Reference 896058-45-0;

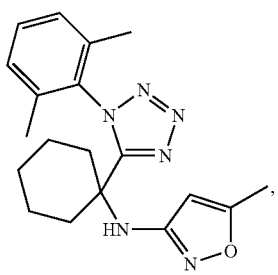

which is disclosed by CAS under Reference 296898-35-6; and

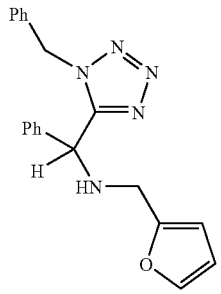

which is disclosed by CAS under Reference 499974-67-3.

When R¹ represents heteroaryl, examples include monocyclic (e.g. 5 and 6 membered) and bicyclic (e.g. 9 and 10 membered, particularly 9 membered) heteroaryl rings, especially rings containing nitrogen atoms (e.g. 1 or 2 nitrogen atoms). A suitable bicyclic heteroaryl ring is a 9-membered heteroaryl ring containing 1 or 2 nitrogen atoms, especially a benzene ring fused to a 5-membered ring containing one or two nitrogen atoms (e.g. 1H-benzoimidazolyl). Most suitably the point of attachment is through a benzene ring, e.g. the group is 1H-benzoimidazol-5-yl. Aforementioned heteroaryl groups may either be unsubstituted (which is more typical) or may suitably be substituted by one or more (e.g. 1 or 2) substituents selected from alkyl (e.g. C$_{1-4}$ alkyl), alkoxy- (e.g. C$_{1-4}$ alkoxy-) and halogen (e.g. F).

When R¹ represents -carbocyclyl-heteroaryl, examples of carbocyclyl include cycloalkyl (e.g. cyclohexyl) and cycloalkenyl (e.g. cyclohexenyl), examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g. C$_{1-4}$ alkyl), alkoxy- (e.g. C$_{1-4}$ alkoxy-) and halogen (e.g. F). A suitable heteroaryl group is imidazol-1-yl. An exemplary -carbocyclyl-heteroaryl group is 3-imidazol-1-yl-cyclohexyl-.

When R¹ represents -alkenylheteroaryl, examples of alkenyl include C$_{2-6}$ alkenyl, especially C$_{2-4}$ alkenyl, in particular propenyl and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g. C$_{1-4}$alkyl), alkoxy- (e.g. C$_{1-4}$ alkoxy-) and halogen (e.g. F). A suitable heteroaryl group is imidazolyl, particularly imidazol-1-yl. An exemplary -alkenylheteroaryl group is 3-imidazol-1-yl-prop-2-enyl-.

When R¹ represents -alkylheteroaryl, examples of alkyl include C$_{1-6}$ alkyl, especially C$_{2-4}$ alkyl, in particular propyl, and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is most typical) or may suitably be substituted by one or more (e.g. 1 or 2) substituents selected from alkyl (e.g. C$_{1-4}$ alkyl), alkoxy- (e.g. C$_{1-4}$ alkoxy-) and halogen (e.g. F). A suitable heteroaryl group is imidazol-1-yl. A particularly suitable -alkylheteroaryl group is 3-imidazol-1-yl-propyl-.

Particular examples of R¹ heteroaryl groups include a 5-membered ring containing 2 or 3 nitrogen atoms, which ring may optionally be substituted (e.g. in particular by one or two groups, such as methyl or —C(NH)NH$_2$), for example:

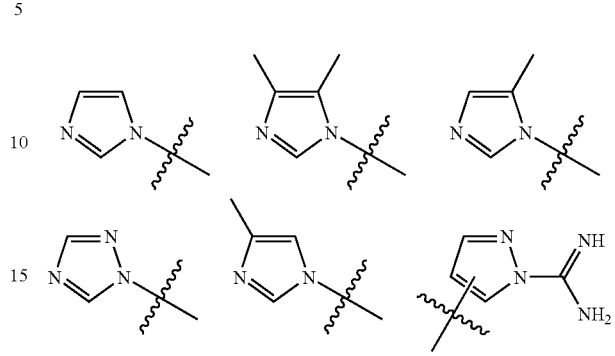

Other examples of R¹ heteroaryl groups include a 9-membered bicyclic ring containing 2 nitrogen atoms, which ring may optionally be substituted, for example:

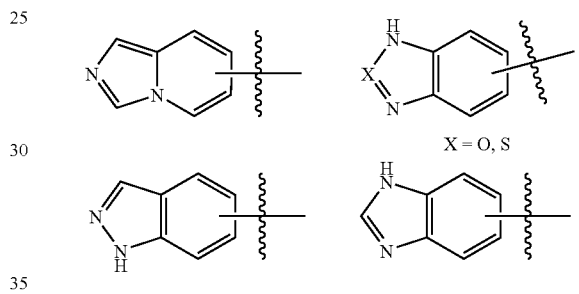

X = O, S

Clearly, the heteroaryl groups shown above may also be present as part of a larger R¹ function such as -carbocyclyl-heteroaryl, -alkenylheteroaryl or -alkylheteroaryl.

When R² represents alkyl (e.g. C$_{1-8}$alkyl), examples include methyl, ethyl, propyl, butyl (e.g. n-butyl, sec-butyl, iso-butyl, tert-butyl), pentyl (e.g. n-pentyl) hexyl (e.g. n-hexyl) (i.e. C$_{1-6}$alkyl), or heptyl (e.g. n-heptyl).

When R² represents -alkyl-amino (e.g. C$_{1-6}$alkyl-amino), examples include dimethylamino-methyl-, 1-dimethylamino-ethyl-, 2-dimethylamino-ethyl-, 1-dimethylamino-propyl-, 2-dimethylamino-propyl-, 3-dimethylamino-propyl-, diethylamino-methyl-, 1-diethylamino-ethyl-, 2-diethylamino-ethyl-, 1-diethylamino-propyl-, 2-diethylamino-propyl- and 3-diethylamino-propyl-.

When R² represents -alkyl-thioalkyl (e.g. C$_{1-4}$alkyl-C$_{1-4}$thioalkyl), examples include —CH$_2$SMe, —CH$_2$CH$_2$SMe and —CH$_2$SEt.

When R² represents haloalkyl- (e.g. —C$_{1-6}$haloalkyl), examples include CF$_3$.

When R² represents hydroxyalkyl- (e.g. —C$_{1-6}$hydroxyalkyl), examples include —CH$_2$OH.

When R² represents -alkyl-alkoxyl (e.g. —C$_{1-4}$alkyl-C$_{1-4}$-alkoxy), examples include —CH$_2$OMe.

When R² represents -alkyl-COOH (e.g. C$_{1-6}$alkyl-COOH), examples include —CH$_2$COOH.

When R² represents -alkyl-C(O)O-alkyl (e.g. C$_{1-4}$alkyl-C(O)O—C$_{1-4}$alkyl), examples include —CH$_2$C(O)OMe, —CH$_2$C(O)OEt, —CH$_2$C(O)OtBu, —CH$_2$CH$_2$C(O)OMe, —CH$_2$CH$_2$C(O)OEt and —CH$_2$CH$_2$C(O)OtBu.

When $R^2$ represents carbocyclyl, examples include cycloalkenyl (e.g. cyclohex-2-enyl, cyclohex-3-enyl, and cycloalkyl (e.g. cyclopropyl, cyclobutyl, cyclopentyl and cyclohexyl).

When $R^2$ represents substituted carbocyclyl, examples include (S)-2-methyl-cyclohex-2-enyl, cyclopropanecarboxylic acid ethyl ester, trifluoromethyl-cyclohexyl-, fluoro-cyclohexyl-, methoxy-cyclohexyl- and 3-methyl-cyclohexyl, aminocyclohexyl, thiomethyl-cyclohexyl-, hydroxycyclohexyl-.

When $R^2$ represents alkenyl (e.g. $C_{2-6}$alkenyl), examples include vinyl (i.e. ethenyl), propenyl (e.g. propen-1-yl, propen-2-yl), butenyl, pentenyl and (1E,3E)-pentadienyl.

When $R^2$ represents alkynyl (e.g. $C_{2-6}$alkynyl), examples include ethynyl.

When $R^2$ represents -alkyl-aryl (e.g. $C_{1-4}$alkyl-aryl), examples include benzyl (i.e. phenyl-methyl-), phenyl-ethyl- (e.g. 1-phenyl-ethyl-, 2-phenyl-ethyl-), phenyl-propyl- (e.g. 1-phenyl-propyl-, 2-phenyl-propyl-, 3-phenyl-propyl-), tolyl-methyl-, tolyl-ethyl- (e.g. 1-tolyl-ethyl-, 2-tolyl-ethyl-), tolyl-propyl- (e.g. 1-tolyl-propyl-, 2-tolyl-propyl-, 3-tolyl-propyl-).

When $R^2$ represents -alkyl-heteroaryl (e.g. $C_{1-4}$alkyl-heteroaryl), examples include -propyl-3-benzo[1,3]dioxol-5-yl, (5-methyl-furan-2-yl)-methyl-, (5-methyl-furan-2-yl)-ethyl-, (5-methyl-furan-2-yl)-propyl-, (5-methyl-furan-3-yl)-methyl-, (5-methyl-furan-3-yl)-ethyl-, (5-methyl-furan-3-yl)-propyl-, (5-methyl-pyrrol-2-yl)-methyl-, (5-methyl-pyrrol-2-yl)-ethyl-, (5-methyl-pyrrol-2-yl)-propyl-, (5-methyl-pyrrol-3-yl)-methyl-, (5-methyl-pyrrol-3-yl)-ethyl-, (5-methyl-pyrrol-3-yl)-propyl-, (5-methyl-thiophen-2-yl)-methyl-, (5-methyl-thiophen-2-yl)-ethyl-, (5-methyl-thiophen-2-yl)-propyl-, (5-methyl-thiophen-3-yl)-methyl-, (5-methyl-thiophen-3-yl)-ethyl-, (5-methyl-thiophen-3-yl)-propyl-.

When $R^2$ represents -aryl heteroaryl (such as -(monocyclic aryl)-(monocyclic heteroaryl)), examples include 4-(pyridin-2-yl)-phenyl-, 4-(pyridin-3-yl)-phenyl-, 4-(pyridin-4-yl)-phenyl-.

When $R^2$ represents -aryl-aryl (such as -(monocyclic aryl)-(monocyclic aryl)), examples include -biphenyl.

When $R^2$ represents -heteroaryl-heteroaryl (such as -(monocyclic heteroaryl)-(monocyclic heteroaryl)), examples include 4-(pyridin-2-yl)-pyridin-2-yl-.

When $R^2$ represents -heteroaryl-aryl (such as -(monocyclic heteroaryl)-(monocyclic aryl)), examples include (4-phenyl)-pyridin-2-yl-.

When $R^2$ represents -alkylcarbocyclyl (e.g. $C_{1-4}$alkyl-carbocyclyl), examples include -methylcycloalkyl e.g.-methyl-cyclohexyl.

When $R^2$ represents -alkylheterocyclyl (e.g. $C_{1-4}$alkyl-heteroyclyl), examples include -methyl-piperidin-1-yl.

When $R^2$ represents -aryl, $R^2$ can be monocyclic or bicyclic but suitably monocyclic. $R^2$ may be unsubstituted (e.g. phenyl or naphthyl) or substituted. Examples of substituted $R^2$ include o-tolyl, m-tolyl, p-tolyl, 2,4-dimethyl-phenyl-, 3,4-dimethyl-phenyl-, 3,5-dimethyl-phenyl-, 2,4,5-trimethyl-phenyl-, 2-methoxy-phenyl-, 3-methoxy-phenyl-, 4-methoxy-phenyl-, 2-fluoro-phenyl-, 3-fluoro-phenyl-, 4-fluoro-phenyl-, 3,4-difluoro-phenyl-, 3,5-difluoro-phenyl-, 2-chloro-phenyl-, 3-chloro-phenyl-, 4-chloro-phenyl-, 3,4-dichloro-phenyl-, 3,5-dichloro-phenyl-, 2-bromo-phenyl-, 3-bromo-phenyl-, 4-bromo-phenyl-, 3,4-dibromo-phenyl-, 3,5-dibromo-phenyl-, 2-hydroxy-phenyl-, 3-hydroxy-phenyl-, 4-hydroxy-phenyl-, 2-hydroxy-5-chloro-phenyl-, 2-hydroxy-5-methyl-phenyl-, 2-methyl-4-methoxy-phenyl-, 3-benzoic acid methyl ester-, 3-bromo-4-methoxy-phenyl-, 3-cyano-4-fluoro-phenyl-, 3-fluoro-4-methoxy-phenyl-, 3-hydroxy-4-methoxy-phenyl-, 3-propoxy-phenyl-, 4-chloro-3-fluoro-phenyl-, 4-chloro-3-nitro-phenyl-, 4-dimethylamino-phenyl-, 4-ethyl-phenyl-, 4-methoxy-2,5-dimethyl-phenyl-, 4-methoxy-2-methyl-phenyl-, 4-methoxy-2-hydroxy-phenyl-, 4-methanesulfonyl-phenyl-, 5-chloro-2-hydroxy-phenyl-.

When $R^2$ represents heteroaryl, examples include monocyclic and bicyclic ring systems, which may be unsubstituted or substituted. When $R^2$ is unsubstituted bicyclic heteroaryl, examples include 1H-indol-3-yl, 1H-indol-5-yl, benzo[c][1,2,5]thiadiazol-5-yl, benzo[b]thiophen-3-yl, benzofuran-2-yl, quinolin-2-yl, quinolin-3-yl and quinolin-4-yl. When $R^2$ is unsubstituted monocyclic heteroaryl, examples include thiophen-2-yl, thiophen-3-yl, furan-2-yl, pyridin-2-yl, pyridin-3-yl and pyridin-4-yl. When $R^2$ is substituted bicyclic heteroaryl, examples include 8-hydroxy-quinolin-2-yl, 6-fluoro-1H-indol-3-yl, 6-methyl-1H-indol-3-yl, chromen-2-one, chromen-4-one, 6-methyl-chromen-4-one and benzo[1,3]dioxol-5-yl. When $R^2$ is substituted monocyclic heteroaryl, examples include 5-methyl-thiophen-2-yl, 5-ethyl-thiophen-2-yl, 5-methyl-furan-2-yl, 5-ethyl-furan-2-yl, 2,4-dimethoxy-pyrimidin-5-yl and 5-methylhydroxy-furan-2-yl.

When $R^2$ represents heterocyclyl, examples include (S)-3,4-dihydro-2H-pyran-2-yl.

When $R^2$ and $R^4$ together form a carbocyclyl group, $R^2$ and $R^4$ may for example together form a cycloalkyl group. For example $R^2$ and $R^4$ may together form a —$(CH_2)_{2-8}$— alkylene chain, suitably —$(CH_2)_{2-5}$—. Specific examples include —$(CH_2)_3$— (i.e. spiro-cyclobutyl), —$(CH_2)_4$— (i.e. spiro-cyclopentyl) and —$(CH_2)_5$— (i.e. spiro-cyclohexyl). Alternatively (and less suitably) $R^2$ and $R^4$ may for example together form a cycloalkenyl group. The carbocyclyl group represented by $R^2$ and $R^4$ together may not be substituted or may be substituted by e.g. 1 or 2 alkyl groups such as methyl groups. Suitably it is not substituted.

In one embodiment, $R^3$ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)$_2$, -alkyl(heteroaryl)$_2$, -alkyl(aryl)(heteroaryl), -alkyl-heteroaryl; -alkyl-heterocyclyl which heterocyclyl group may optionally be substituted by one or more groups selected from alkyl, hydroxy and oxo; -alkyl-carbocyclyl; -aryl-heteroaryl; -heteroaryl-aryl; -aryl-aryl; -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.

When $R^3$ represents alkyl (e.g. $C_{1-6}$alkyl), examples include methyl, ethyl, propyl, butyl (e.g. n-butyl, iso-butyl, sec-butyl, tert-butyl), 2,2-dimethyl-propyl, pentyl (e.g. n-pentyl), hexyl (e.g. n-hexyl).

When $R^3$ represents alkoxy-alkyl- (e.g. $C_{1-4}$alkoxy-$C_{1-4}$alkyl-), examples include methoxy-methyl-, 1-methoxy-ethyl-, 2-methoxy-ethyl-, 1-methoxy-propyl-, 2-methoxy-propyl-, 3-methoxy-propyl-, ethoxy-methyl-, 1-ethoxy-ethyl-, 2-ethoxy-ethyl-, 1-ethoxy-propyl-, 2-ethoxy-propyl- and 3-ethoxy-propyl-.

When $R^3$ represents -alkyl-C(O)Oalkyl (e.g. —$C_{1-4}$alkyl-C(O)O—$C_{1-4}$alkyl), examples include —$CH_2C(O)OMe$, —$CH_2C(O)OEt$, —$CH_2C(O)OPr$, —$CH_2C(O)OtBu$.

When $R^3$ represents -alkyl-amino (e.g. —$C_{1-6}$alkylamino), examples include dimethylamino-methyl-, 1-dimethylamino-ethyl-, 2-dimethylamino-ethyl-, 1-dimethylamino-propyl-, 2-dimethylamino-propyl-, 3-dimethylamino-propyl-, diethylamino-methyl-, 1-diethylamino-ethyl-, 2-diethylamino-ethyl-, 1-diethylamino-propyl-, 2-diethylamino-propyl-, 3-diethylamino-propyl-.

When $R^3$ represents haloalkyl (e.g. —$C_{1-6}$haloalkyl), examples include $CF_3$.

When $R^3$ represents hydroxyalkyl (e.g. —$C_{1-6}$hydroxyalkyl), examples include —$CH_2OH$.

When $R^3$ represents -alkyl-thioalkyl (e.g. —$C_{1-4}$alkyl-$C_{1-4}$-thioalkyl), examples include —$CH_2SMe$.

When $R^3$ represents -alkyl-COOH (e.g. $C_{1-6}$alkyl-COOH), examples include —$CH_2COOH$.

When $R^3$ represents carbocyclyl, it may optionally be substituted. Examples of unsubstituted carbocyclyl include cycloalkenyl (e.g. cyclohex-1-enyl, cyclohex-3-enyl) and cycloalkyl (e.g. cyclopropyl, cyclobutyl, cyclopentyl, cyclohexyl or cycloheptyl). Thus cycloalkyl may represent cyclopropyl, cyclobutyl, cyclopentyl or cycloheptyl. Alternatively it may represent cyclohexyl. Examples of substituted carbocyclyl include cycloalkyl or cycloalkenyl substituted by alkyl (e.g. 2-methyl-cyclohexyl), halogen (e.g. 1, 2 or 3 halogen atoms such as chlorocyclohexyl); -haloalkyl (e.g. $CF_3$), hydroxyl (e.g. hydroxycyclohexyl- and 3,4-dihydroxy-cyclohexyl-); —C(O)O-alkyl (e.g. cyclohexyl substituted by —C(O)OMe or —C(O)OEt); —C(O)OH (e.g. cyclohexyl substituted by —C(O)OH); alkoxy, (e.g. cyclohexyl substituted by methoxy, cyclohexenyl substituted by methoxy-); -thioalkyl (e.g. cyclohexyl substituted by -thioalkyl); amino (e.g. cyclohexyl substituted by amino).

Examples of -cycloalkyl-C(O)Oalkyl (e.g.-cycloalkyl-C(O)O—$C_{1-4}$alkyl) include -cyclopentane-2-carboxylic acid ethyl ester, -cyclopentane-2-carboxylic acid ethyl ester-3-methyl, -cyclohexane-2-carboxylic acid ethyl ester, -cyclopentane-2-(carboxylic acid methyl ester), -cyclopentane-2-carboxylic acid methyl ester, -3-methyl, -cyclohexane-2-carboxylic acid methyl ester.

When $R^3$ represents alkenyl (e.g. $C_{2-6}$alkenyl), examples include vinyl (i.e. ethenyl), propenyl (e.g. propen-1-yl, propen-2-yl (i.e. allyl)), (1E,3E)-butadienyl, (1E,3E)-pentadienyl.

When $R^3$ represents -alkyl aryl (e.g. —$C_{1-4}$alkyl aryl), examples include benzyl, 1-phenyl-ethyl-, 2-phenyl-ethyl-, 1-tolyl-ethyl-, 2-tolyl-ethyl-, 3-phenyl-propyl-, 3-tolyl-propyl-, 4-phenyl-butyl-, 4-tolyl-butyl-, 2-chloro-benzyl-, 3-chloro-benzyl- and 4-chloro-benzyl-. In one embodiment, examples include 1-phenyl-ethyl-, 2-phenyl-ethyl-, 1-tolyl-ethyl-, 2-tolyl-ethyl-, 3-phenyl-propyl-, 3-tolyl-propyl-, 4-phenyl-butyl-, 4-tolyl-butyl-, 2-chloro-benzyl-, 3-chloro-benzyl- and 4-chloro-benzyl-. Further examples include (2-fluorophenyl)-methyl-, (3-fluorophenyl)-methyl-, (4-fluorophenyl)-methyl- and (2,4-difluorophenyl)-methyl-.

When $R^3$ represents -alkyl(aryl)$_2$ (e.g. —$C_{1-4}$alkyl(aryl)$_2$), examples include diphenylmethyl-, 1,2-diphenyl-ethyl-, 2,2-diphenyl-ethyl-, 3,3-diphenyl-propyl-, ditolylmethyl-, 2,2-ditolyl-ethyl-, and 3,3-ditolyl-propyl-.

When $R^3$ represents -alkyl(heteroaryl)$_2$ (e.g. —$C_{1-4}$alkyl (heteroaryl)$_2$), examples include 2,2-pyridinyl-methyl-, 2,2-pyridinyl-ethyl- and 3,3-pyridinyl-propyl-.

When $R^3$ represents -alkyl(aryl)(heteroaryl) (e.g. —$C_{1-4}$alkyl(aryl)(heteroaryl)) examples include 2-phenyl-2-pyridinyl-methyl-, 2-phenyl-2-pyridinyl-ethyl- and 3-phenyl-3-pyridinyl-propyl-.

When $R^3$ represents -alkyl-heteroaryl (e.g. —$C_{1-4}$alkyl-heteroaryl), examples include pyridin-2-yl-methyl-, pyridin-3-yl-methyl-, pyridin-4-yl-methyl-, 2-thiophen-2-yl-ethyl-, furan-2-yl-methyl- and pyrrolyl-methyl-. In one embodiment examples include pyridin-2-yl-methyl-, pyridin-4-yl-methyl-, 2-thiophen-2-yl-ethyl-, furan-2-yl-methyl- and pyrrolyl-methyl-.

When $R^3$ represents -alkyl heterocyclyl (e.g. —$C_{1-4}$alkyl heterocyclyl) which heterocycyl group may optionally be substituted by one or more groups selected from alkyl, hydroxyl and oxo, examples include 2,2-dimethyl-[1,3]dioxolan-4-ylmethyl-, (tetrahydro-furan-2-yl)methyl- and -propyl-3-pyrrolidin-2-one. Suitably heterocyclyl is not substituted.

When $R^3$ represents -alkylcarbocyclyl (e.g. $C_{1-4}$alkyl-carbocyclyl), examples include -methylcycloalkyl e.g.-methylcyclohexyl.

When $R^3$ represents -aryl-heteroaryl (such as -(monocyclic aryl)-(monocyclic heteroaryl)), examples include 4-pyridin-2-yl-phenyl-.

When $R^3$ represents -aryl-aryl (such as -(monocyclic aryl)-(monocyclic aryl)), examples include -biphenyl.

When $R^3$ represents -aryl-O-aryl examples include phenoxyphenyl (e.g. 4-phenoxyphenyl).

When $R^3$ represents -heteroaryl-heteroaryl (such as -(monocyclic heteroaryl)-(monocyclic heteroaryl)), examples include 4-(pyridin-2-yl)-pyridin-2-yl-.

When $R^3$ represents -heteroaryl-aryl (such as -(monocyclic heteroaryl)-(monocyclic aryl)), examples include (4-phenyl)-pyridin-2-yl-.

When $R^3$ represents aryl, examples include phenyl optionally substituted by one or more substituents e.g. one or more substituents selected from nitro, alkyl (e.g. tert-butyl), alkoxy, halogen and haloalkyl; e.g. one substituent, e.g. one substituent at the 4-position. Thus when $R^3$ represents aryl, examples include 4-nitro-phenyl- and 4-tert-butyl-phenyl-.

When $R^3$ represents heteroaryl, examples include 2,3-dihydro-benzo[1,4]dioxin-6-yl. Another example is benzo-1,3-dioxol-5-yl. Further examples include furanyl, pyrrolyl and thiophenyl.

When $R^3$ represents heterocyclyl, examples include tetrahydrofuran-2-yl, 3,4-dihydro-2H-pyranyl, piperidinyl and pyrrolidinyl.

When $R^3$ represents -aryl-alkyl-aryl (e.g. -aryl-$C_{1-4}$alkyl-aryl, especially wherein aryl represents monocyclic aryl), examples include 4-benzyl-phenyl- and 4-(4-methyl-benzyl)-phenyl-.

When $R^3$ represents -aryl-Oalkyl-aryl (e.g. -aryl-O—$C_{1-4}$ alkyl-aryl, especially wherein aryl represents monocyclic aryl), examples include 2-benzyloxy-phenyl-.

When $R^3$ represents -alkyl-C(O)—NH-alkyl-aryl (e.g. —$C_{1-4}$alkyl-C(O)—NH—$C_{1-4}$alkyl-aryl), examples include —$CH_2$—C(O)—N-alkyl-aryl, (e.g. —$CH_2$—C(O)—N—$CH_2$-phenyl).

When $R^3$ represents -alkyl-C(O)—NH-alkyl-heteroaryl (e.g. —$C_{1-4}$alkyl-C(O)—NH—$C_{1-4}$ alkyl-heteroaryl), examples include -methyl-CONH-ethyl-heteroaryl e.g. $CH_2C(O)N$—$CH_2CH_2$-(1H-indol-3-yl).

When $R^3$ represents alkyl-C(O)—(N-piperidinyl) or -alkyl-C(O)—(N-pyrrolidinyl) in which piperidinyl or pyrrolidinyl may optionally be fused to optionally substituted phenyl, examples include -methyl-C(O)—(N-piperidinyl) or -methyl-C(O)—(N-pyrrolidinyl) in which piperidinyl or pyrrolidinyl may optionally be fused (e.g. between the 3 and 4 position) to phenyl.

When $R^3$ represents -alkyl-C(O)—NH-alkyl-heterocyclyl (e.g. —$C_{1-4}$alkyl-C(O)—NH—$C_{1-4}$ alkyl-heterocyclyl), examples include —$CH_2CONHCH_2$(piperidin-1-yl).

When $R^4$ represents alkyl (e.g. $C_{1-4}$alkyl), examples include methyl, ethyl and propyl. Suitably, $R^1$ represents represents heteroaryl or -alkylheteroaryl, particularly -alkylheteroaryl.

Suitably, when $R^1$ represents heteroaryl, $R^1$ represents bicyclic heteroaryl, especially 9-membered bicyclic heteroaryl. More suitably, $R^1$ represents a bicyclic heteroaryl ring system and in particular a phenyl ring fused with a 5 membered heteroaryl ring containing one or more (e.g. one or two, suitably one) nitrogen atoms. Suitably $R^1$ represents unsubstituted heteroaryl. In particular, $R^1$ suitably represents 1H-benzoimidazolyl, especially 1H-benzoimidazol-5-yl.

Suitably, when $R^1$ represents -alkylheteroaryl, alkyl represents $C_{2-4}$ alkyl, e.g. $C_{3-4}$ alkyl most suitably propyl. When $R^1$ represents -alkylheteroaryl, $R^1$ heteroaryl is suitably 5 or 6 membered monocyclic heteroaryl, especially 5 membered monocyclic heteroaryl. Suitably, when $R^1$ represents -alkylheteroaryl, the heteroaryl ring contains nitrogen atoms (e.g. 1 or 2 nitrogen atoms, suitably 2 nitrogen atoms) and is suitably unsubstituted. A particularly suitable heteroaryl group is imidazolyl, especially imidazol-1-yl. Most suitably, when $R^1$ represents -alkylheteroaryl, $R^1$ represents 3-imidazol-1-yl-propyl-.

Suitably, $R^2$ represents alkyl, which may optionally be substituted by one or more groups selected from -thioalkyl and —C(O)O-alkyl; carbocyclyl, which may optionally be substituted by one or more groups selected from -alkyl, -thioalkyl and —C(O)O-alkyl; alkenyl; -alkyl-aryl; -alkyl-heteroaryl; -aryl heteroaryl; -aryl (e.g. optionally substituted phenyl); heteroaryl (monocyclic or bicyclic); heterocyclyl; or $R^2$ together with $R^4$ represents carbocyclyl optionally substituted by one or more (e.g. 1 or 2) methyl groups. More suitably, $R^2$ represents -aryl-heteroaryl, aryl or heteroaryl; or $R^2$ together with $R^4$ represents cycloalkyl (e.g. cyclobutyl). Most suitably, $R^2$ represents -aryl or heteroaryl; or $R^2$ together with $R^4$ represents cycloalkyl (e.g. cyclobutyl). Particularly suitably $R^2$ represents aryl or heteroaryl, especially aryl.

When $R^2$ represents -aryl-heteroaryl, $R^2$ is suitably 4-pyridin-2-yl-phenyl-.

When $R^2$ represents aryl, $R^2$ is suitably monocyclic, especially substituted phenyl. Most suitably, $R^2$ represents: 2-hydroxy-5-methyl-phenyl-, 2-methyl-4-methoxy-phenyl-, 3,4-dichloro-phenyl-, 3,5-dibromo-phenyl-, 2-benzoic acid methyl ester, 3-bromo-4-methoxy-phenyl-, 3-hydroxy-4-methoxy-phenyl-, 3-propoxy-phenyl-, 4-bromo-phenyl-, 4-chloro-3-nitro-phenyl-, 4-methoxy-2-methyl-phenyl-, 4-methoxy-phenyl.

When $R^2$ represents heteroaryl, $R^2$ is suitably bicyclic. Most suitably, $R^2$ represents 1H-indol-5-yl, 2-quinolin-8-ol, benzo[1,2,5]thiophen-3-yl, benzo[b]thiophen-3-yl, benzofuran-2-yl, quinolin-2-yl, quinolin-3-yl, benzo[1,3]dioxol-5-yl.

Suitably $R^3$ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)$_2$, -alkyl(heteroaryl)$_2$, -alkyl(aryl)(heteroaryl), -alkyl-heteroaryl; -alkyl-heterocyclyl which heterocyclyl group may optionally be substituted by one or more groups selected from alkyl, hydroxy and oxo; -alkyl-carbocyclyl; -alkyl-heteroaryl; -heteroaryl-aryl; -aryl-aryl; -heteroaryl-heteroaryl; -aryl; -heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.

More suitably, $R^3$ represents alkyl, which may optionally be substituted by one or more groups selected from amino, alkoxy-, and —C(O)O-alkyl; carbocyclyl, which may optionally be substituted by one or more groups selected from alkyl, amino, alkoxy-, and —C(O)O-alkyl; alkenyl; -alkyl-aryl; -alkyl(aryl)$_2$, -alkyl-heteroaryl; -alkyl-heterocyclyl which heterocyclyl group may optionally be substituted by one or more (e.g. 1 or 2) groups selected from alkyl (e.g. methyl) and oxo; -aryl; heteroaryl (monocyclic or bicyclic); -aryl-Oalkyl-aryl; -alkyl-C(O)—NH-alkyl-heteroaryl; -alkyl-C(O)NH—(N-piperidinyl) in which piperidinyl or pyrrolidinyl may optionally be fused to optionally substituted phenyl. More suitably, $R^3$ represents alkyl or cycloalkyl either of which can be unsubstituted or substituted by —C(O)Oalkyl; alkyl substituted by alkoxy; -aryl-Oalkyl-aryl; -alkyl-aryl; -alkyl-heteroaryl; -alkyl-heterocyclyl; -alkyl-C(O)—NH-alkyl-heteroaryl. Yet more suitably, $R^3$ represents unsubstituted alkyl, alkyl substituted by —C(O)Oalkyl; -alkyl-aryl; or -alkyl-heteroaryl, especially unsubstituted alkyl (e.g. $C_{1-6}$alkyl). When $R^3$ represents a moiety comprising an aryl group, aryl is suitably substituted aryl (such as substituted phenyl).

Suitably, when $R^3$ represents unsubstituted alkyl, $R^3$ represents n-butyl, t-butyl or 2,2-dimethyl-propyl, particularly 2,2-dimethylpropyl.

Suitably, when $R^3$ represents unsubstituted cycloalkyl, $R^3$ represents cyclopentyl or cyclohexyl.

Suitably, when $R^3$ represents -alkyl-C(O)Oalkyl, $R^3$ represents —CH$_2$C(O)OMe or —CH$_2$C(O)OtBu.

Suitably, when $R^3$ represents -cycloalkyl-C(O)Oalkyl, $R^3$ represents cyclohexane-2-carboxylic acid ethyl ester.

Suitably, when $R^3$ represents alkoxy-alkyl-, $R^3$ represents 3-methoxy-propyl-.

Suitably, when $R^3$ represents -aryl-Oalkyl-aryl, $R^3$ represents 2-benzyloxy-phenyl-.

Suitably, when $R^3$ represents -alkyl-aryl, aryl represents phenyl or substituted phenyl, e.g. phenyl substituted by one or more halogen atoms. For example, $R^3$ may represent benzyl, 2-chloro-benzyl- or 4-chloro-benzyl.

Suitably, when $R^3$ represents -alkyl-heteroaryl, $R^3$ represents pyridin-3-yl-methyl- or 2-thiophen-2-yl-ethyl-.

Suitably, when $R^3$ represents -alkyl-heterocyclyl which heterocyclyl group may optionally be substituted by one or more groups selected from alkyl, hydroxyl and oxo, $R^3$ represents 1-(tetrahydro-furan-2-yl)methyl- e.g. (S)-1-(tetrahydro-furan-2-yl)methyl-.

Suitably, when $R^3$ represents -alkyl-C(O)—N-alkyl-aryl, $R^3$ represents —CH$_2$C(O)N-(2-(1H-indol-3-yl)-ethyl).

When $R^2$ together with $R^4$ does not form a carbocyclyl group, suitably $R^4$ represents hydrogen.

Processes

A process for preparation of compounds of formula (I) or a protected derivative thereof comprises reaction of a compound of formula (II)

(II)

or a protected derivative thereof, wherein $R^1$ and $R^2$ are as defined above, with a suitable azide such as trimethylsilylazide and a compound of formula (III)

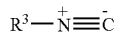
(III)

or a protected derivative thereof, wherein $R^3$ is as defined above.

The reagents will typically be combined in a polar protic organic solvent (e.g. an alcohol such as methanol).

Compounds of formula (III) are either known or may be prepared by conventional methods known per se.

Compounds of formula (II) or a protected derivative thereof may be prepared by reaction of a compound of formula (IV),

(IV)

or a protected derivative thereof, wherein $R^2$ is as defined above, with a compound of formula (V)

(V)

or a protected derivative thereof, wherein $R^1$ is as defined above under suitable imine-forming reaction conditions. Suitable conditions include combining the reagents in a polar protic solvent at ambient or elevated temperature.

In a suitable method of preparing compounds of formula (I), compounds of formula (II) are prepared in situ and are not isolated before further reaction with (III).

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16, CCL 18, Fractalkine, Orexin A, [Gln$^3$]-glucagon (3-29), [Gln$^5$]-substance P(5-11) and the peptide QYNAD. For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
| --- | --- | --- |
| Abeta(1-42) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(1-40) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(3-42) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(3-40) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(11-42) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(11-40) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri | EASNCFA IRHFENKFAV ETLIC SRTVKKNIIEEN | Pyroglutamated form plays a role in Familial British Dementia |

TABLE 1-continued

Amino acid sequences of physiological active peptides with an N-terminal glutamine residue, which are prone to be cyclized to final pGlu

| Peptide | Amino acid sequence | Function |
|---|---|---|
| ADan | EASNCFA IRHFENKFAV ETLIC FNLFLNSQEKHY | Pyroglutamated form plays a role in Familial Danish Dementia |
| Gastrin 17 Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/ neuromodulator in the central and peripheral nervous systems. |
| GnRH Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16) Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (small inducible cytokine A2) Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| CCL18 (small inducible cytokine A18) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible cytokine A7) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |
| QYNAD | Gln-Tyr-Asn-Ala-Asp | Acts on voltage-gated sodium channels. |

Glutamate is found in positions 3, 11 and 22 of the amyloid μ-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid 1-peptides 1-40 (42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the -secretase enzyme 1-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophic releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2, CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, Down Syndrome, Huntington's disease, Kennedy's disease, ulcer disease, duodenal cancer with or w/o *Helicobacter* pylori infections, colorectal cancer, Zolliger-Ellison syndrome, gastric cancer with or without *Helicobacter* pylori infections, pathogenic psychotic conditions, schizophrenia, infertility, neoplasia, inflammatory host responses, cancer, malign metastasis, melanoma, psoriasis, rheumatoid arthritis, atherosclerosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, arteriosclerosis and multiple sclerosis.

The present invention also provides a method of treatment of the aforementioned diseases comprising the administration of a therapeutically active amount of at least one compound of formula (I) to a mammal, preferably a human.

Most preferably, said method and corresponding uses are for the treatment of a disease selected from the group consisting of mild cognitive impairment, Alzheimer's disease, Familial British Dementia, Familial Danish Dementia, Down Syndrome, Parkinson disease and Chorea Huntington, comprising the administration of a therapeutically active amount of at least one compound of formula (I) to a mammal, preferably a human.

Even preferably, the present invention provides a method of treatment and corresponding uses for the treatment of rheumatoid arthritis or atherosclerosis.

Even preferably, the present invention provides a method of treatment and corresponding uses for the treatment of pancreatitis and restenosis.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said QC inhibitor is a compound of formula (I) of the present invention. More specifically, the aforementioned other agent is selected from the group consisting PEP-inhibitors, LiCl, inhibitors of dipeptidyl aminopeptidases, preferably inhibitors of DP IV or DP IV-like enzymes; acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Further, the aforementioned other agent may be selected from the group consisting of beta-amyloid antibodies, cysteine protease inhibitors and MCP-1 antagonists.

Furthermore, the other agent may be, for example, an anti-anxiety drug or antidepressant selected from the group consisting of (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene, (b) Selective serotonin re-uptake inhibitors (SSRI's), e.g. citalopram, fluoxetine, fluvoxamine, escitalopram, sertraline, paroxetine, (c) Tricyclic antidepressants, e.g. amitryptiline, clomipramine, desipramine, doxepin, imipramine (d) Monoamine oxidase (MAO) inhibitors, (e) Azapirones, e.g. buspirone, tandopsirone, (f) Serotonin-norepinephrine reuptake inhibitors (SNRI's), e.g. venlafaxine, duloxetine, (g) Mirtazapine,
(h) Norepinephrine reuptake inhibitors (NRI's), e.g. reboxetine,
(i) Bupropione,
(j) Nefazodone,
(k) beta-blockers,
(l) NPY-receptor ligands: NPY agonists or antagonists.

In a further embodiment, the other agent may be, for example, an anti-multiple sclerosis drug selected from the group consisting of
  a) dihydroorotase dehydrogenase inhibitors, e.g. SC-12267, teriflunomide, MNA-715, HMR-1279 (syn. to HMR-1715, MNA-279),
  b) autoimmune suppressant, e.g. laquinimod,
  c) paclitaxel,
  d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
  e) peptide nucleic acid (PNA) preparations, e.g. reticulose,
  f) interferon alpha, e.g. Alfaferone, human alpha interferon (syn. to Omniferon, Alpha Leukoferon),
  g) interferon beta, e.g. Frone, interferon beta-1a like Avonex, Betron (Rebif), interferon beta analogs, interferon beta-transferrin fusion protein, recombinant interferon beta-1b like Betaseron,
  h) interferon tau,
  i) peptides, e.g. AT-008, AnergiX.MS, Immunokine (alpha-Immunokine-NNSO3), cyclic peptides like ZD-7349,
  j) therapeutic enzymes, e.g. soluble CD8 (sCD8),
  k) multiple sclerosis-specific autoantigen-encoding plasmid and cytokine-encoding plasmid, e.g. BHT-3009;
  l) inhibitor of TN F-alpha, e.g. BLX-1002, thalidomide, SH-636,
  m) TNF antagonists, e.g. solimastat, lenercept (syn. to RO-45-2081, Tenefuse), onercept (sTNFR1), CC-1069,
  n) TNF alpha, e.g. etanercept (syn. to Enbrel, TNR-001)
  o) CD28 antagonists, e.g. abatacept,
  p) Lck tyrosine kinase inhibitors,
  q) cathepsin K inhibitors,
  r) analogs of the neuron-targeting membrane transporter protein taurine and the plant-derived calpain inhibitor leupeptin, e.g. Neurodur,
  s) chemokine receptor-1 (CCR1) antagonist, e.g. BX-471,
  t) CCR2 antagonists,
  u) AMPA receptor antagonists, e.g. ER-167288-01 and ER-099487, E-2007, talampanel,
  v) potassium channel blockers, e.g. fampridine,
  w) tosyl-proline-phenylalanine small-molecule antagonists of the VLA-4/VCAM interaction, e.g. TBC-3342,
  x) cell adhesion molecule inhibitors, e.g. TBC-772,
  y) antisense oligonucleotides, e.g. EN-101,
  z) antagonists of free immunoglobulin light chain (IgLC) binding to mast cell receptors, e.g. F-991,
  aa) apoptosis inducing antigenes, e.g. Apogen MS,
  bb) alpha-2 adrenoceptor agonist, e.g. tizanidine (syn. to Zanaflex, Ternelin, Sirdalvo, Sirdalud, Mionidine),
  cc) copolymer of L-tyrosine, L-lysine, L-glutamic acid and L-alanine, e.g. glatiramer acetate (syn. to Copaxone, COP-1, copolymer-),
  dd) topoisomerase II modulators, e.g. mitoxantrone hydrochloride,
  ee) adenosine deaminase inhibitor, e.g. cladribine (syn. to Leustatin, Mylinax, RWJ-26251),
  ff) interlaukin-10, e.g. ilodecakin (syn. to Tenovil, Sch-52000, CSIF),
  gg) interleukin-12 antagonists, e.g. lisofylline (syn. to CT-1501R, LSF, lysofylline),
  hh) Ethanaminum, e.g. SRI-62-834 (syn. to CRC-8605, NSC-614383),
  ii) immunomodulators, e.g. SAIK-MS, PNU-156804, alpha-fetoprotein peptide (AFP), IPDS,
  jj) retinoid receptor agonists, e.g. adapalene (syn. to Differin, CD-271),
  kk) TGF-beta, e.g. GDF-1 (growth and differentiation factor 1),
  ll) TGF-beta-2, e.g. BetaKine,
  mm) MMP inhibitors, e.g. glycomed,
  nn) phosphodiesterase 4 (PDE4) inhibitors, e.g. RPR-122818,
  oo) purine nucleoside phosphorylase inhibitors, e.g. 9-(3-pyridylmethyl)-9-deazaguanine, peldesine (syn. to BCX-34, TO-200),
  pp) alpha-4/beta-1 integrin antagonists, e.g. ISIS-104278,
  qq) antisense alpha4 integrin (CD49d), e.g. ISIS-17044, ISIS-27104,
  rr) cytokine-inducing agents, e.g. nucleosides, ICN-17261,
  ss) cytokine inhibitors,
  tt) heat shock protein vaccines, e.g. HSPPC-96,
  uu) neuregulin growth factors, e.g. GGF-2 (syn. to neuregulin, glial growth factor 2),
  vv) cathepsin S-inhibitors,
  ww) bropirimine analogs, e.g. PNU-56169, PNU-63693,
  xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor of formula (I) optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor of formula (I) and at least one of the other agents or the sequential administration thereof.

Co-administration includes administration of a formulation, which comprises at least one QC inhibitor of formula (I) and at least one of the other agents or the essentially simultaneous administration of separate formulations of each agent.

Examples of suitable PIMT enhancers are 10-aminoaliphatyl-dibenz[b, f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No.

7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.) and DNP-004089 (De Novo Pharmaceuticals Ltd.).

Inhibitors of gamma secretase and compositions containing such inhibitors are described, e.g. in WO2005/008250, WO2006/004880, U.S. Pat. No. 7,122,675, U.S. Pat. No. 7,030,239, U.S. Pat. No. 6,992,081, U.S. Pat. No. 6,982,264, WO2005/097768, WO2005/028440, WO2004/101562, U.S. Pat. No. 6,756,511, U.S. Pat. No. 6,683,091, WO03/066592, WO03/014075, WO03/013527, WO02/36555, WO01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. No. 6,713,276, U.S. Pat. No. 6,686,449, WO03/091278, U.S. Pat. No. 6,649,196, U.S. Pat. No. 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.).

A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416-457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Welcome Co.); CX-157 (Krenitsky Pharmaceuticals Inc.); desoxypeganine (H F Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

Suitable histamine H3 antagonists for the purpose of the present invention are, e.g. A-331440, A-349821 (Abbott Laboratories); 3874-HI (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); 1S,2S)-2-(2-Aminoethyl)-1-(1H-imidazol-4-yl)cyclopropane (Hokkaido University); JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221,752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Suitable examples of beta-amyloid antibodies are ACU-5A5, huCO91 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Suitable cysteine protease inhibitors are inhibitors of cathepsin B. Inhibitors of cathepsin B and compositions containing such inhibitors are described, e.g. in WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TE1-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Other suitable compounds that can be used according to the present invention in combination with QC-inhibitors are NPY, a NPY mimetic or a NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1 h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N-2-(diphenylacetyl)-(R)—N-[1-(4-hydroxy-phenyl)ethyl]arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth) and CI-101/(PD-151832) (Pfizer Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (Whanln).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); EpiCept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, $C_{1-1041}$) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-CI-kynurenine (4-CI-KYN)), 7-chloro-kynurenic acid (7-CI-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N2-(adamantly)-hexamethylene-imine) (RAMS); Lancicemine (AR-R-15896) (AstraZeneca); EVT-102, Ro-25-6981 and Ro-63-1908 (Hoffmann-La Roche AG/Evotec).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124, 305; U.S. Pat. No. 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613; WO2006/009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo NordiskA/S).

Other preferred DP IV-inhibitors are (i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;

(ii) peptide structures, disclosed in WO 03/002593, e.g. tripeptides;

(iii) peptidylketones, disclosed in WO 03/033524;

(vi) substituted aminoketones, disclosed in WO 03/040174;

(v) topically active DP IV-inhibitors, disclosed in WO 01/14318;

(vi) prodrugs of DP IV-inhibitors, disclosed in WO 99/67278 and WO 99/67279; and (v) glutaminyl based DP IV-inhibitors, disclosed in WO 03/072556 and WO 2004/099134.

Most preferably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:

a QC inhibitor, in particular a QC inhibitor of formula (I), in combination with Atorvastatin for the treatment and/or prevention of arteriosclerosis a QC inhibitor, in particular a QC inhibitor of formula (I), in combination with immunosuppressive agents, preferably rapamycin for the prevention and/or treatment of restenosis a QC inhibitor, in particular a QC inhibitor of formula (I), in combination with immunosuppressive agents, preferably paclitaxel for the prevention and/or treatment of restenosis a QC inhibitor, in particular a QC inhibitor of formula (I), in combination with AChE inhibitors, preferably Donepezil, for the prevention and/or treatment of Alzheimer's disease a QC inhibitor, in particular a QC inhibitor of formula (I), in combination with interferons, preferably Aronex, for the prevention and/or treatment of multiple sclerosis a QC inhibitor, in particular a QC inhibitor of formula (I), in combination with interferons, preferably betaferon, for the prevention and/or treatment of multiple sclerosis a QC inhibitor, in particular a QC inhibitor of formula (I), in combination with interferons, preferably Rebif, for the prevention and/or treatment of multiple sclerosis a QC inhibitor, in particular a QC inhibitor of formula (I), in combination with Copaxone, for the prevention and/or treatment of multiple sclerosis.

Such a combination therapy is in particular useful for the treatment of mild cognitive impairment, Alzheimers Disease, Familial British Dementia, Familial Danish Dementia and neurodegeneration in Down syndrome as well as atherosclerosis, rheumatoid arthritis, restenosis and pancreatitis.

Such combination therapies might result in a better therapeutic effect (less plaque formation, less proliferation as well as less inflammation, a stimulus for proliferation) than would occur with either agent alone.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, auto injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl eneoxide-polyllysine substituted with palmitoyl residue. Furthermore, the compounds of the present invention may be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I) optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

| Ex. No. | IUPAC Name | Calc. [M + H] | Det. [M + H] | Calc. [M + H] | Det. [M + H] | $IC_{50}$ [uM] |
|---|---|---|---|---|---|---|
| 1 | [[1-(4-Chloro-benzyl)-1H-tetrazol-5-yl]-(3,4-dichloro-phenyl)-methyl]-(3-imidazol-1-yl-propyl)-amine | 476.12 | 476.13 | 498.1 | 0 | 2.2 |
| 2 | [[1-(4-Chloro-benzyl)-1H-tetrazol-5-yl]-(3,4-dimethyl-phenyl)-methyl]-(3-imidazol-1-yl-propyl)-amine | 436.224 | 436.23 | 458.22 | 0 | 6.7 |
| 3 | 2-[[1-(4-Chloro-benzyl)-1H-tetrazol-5-yl]-(3-imidazol-1-yl-propylamino)-methyl]-4-methyl-phenol | 438.22 | 438.2 | 460.2 | 0 | 0.4 |
| 4 | 2-[[1-(4-Chloro-benzyl)-1H-tetrazol-5-yl]-(3-imidazol-1-yl-propylamino)-methyl]-quinolin-8-ol | 475.21 | 475.21 | 497.19 | 0 | 4.9 |
| 5 | 5-[[1-(4-Chloro-benzyl)-1H-tetrazol-5-yl]-(3-imidazol-1-yl-propylamino)-methyl]-2-fluoro-benzonitrile | 451.18 | 451.19 | 437.17 | 0 | 6.7 |
| 6 | [[1-(4-Chloro-benzyl)-1H-tetrazol-5-yl]-(1H-indol-5-yl)-methyl]-(3-imidazol-1-yl propyl)-amine | 447.21 | 447.22 | 469.2 | 0 | 0.4 |
| 7 | {[1-(4-Chloro-benzyl)-1H-tetrazol-5-yl]-quinolin-2-yl-methyl}-(3-imidazol-1-yl-propyl)-amine | 459.21 | 459.23 | 481.2 | 0 | 1.3 |
| 8 | [[1-(4-Chloro-benzyl)-1H-tetrazol-5-yl]-((S)-2-methyl-cyclohex-2-enyl)-methyl]-(3-imidazol-1-yl-propyl)-amine | 426.26 | 0 | 448.24 | 0 | 4 |
| 9 | {(S)-[1-(4-Chloro-benzyl)-1H-tetrazol-5-yl]-3,4-dihydro-2H-pyran-2-yl-methyl}-(3- | 414.22 | 0 | 436.2 | 0 | 4.9 |

| | | | | | | |
|---|---|---|---|---|---|---|
| 10 | ((3,4-Dichloro-phenyl)-{1-[(S)-1-(tetrahydro-furan 2-yl)methyl]-1H-tetrazol-5-yl}-methyl)-(3-imidazol-1-yl-propyl)-amine | 436.18 | 436.18 | 458.16 | 0 | 4 |
| 11 | 2-((3-Imidazol-1-yl-propylamino)-{1-[(S)-1-(tetrahydro-furan-2-yl)methyl]-1H-tetrazol-5-yl}-methyl)-4-methyl-phenol | 398.27 | 398.27 | 420.26 | 420.27 | 3.1 |
| 12 | 2-((3-Imidazol-1-yl-propylamino)-{1-[(S)-1-(tetrahydro-furan-2-yl)methyl]-1H-tetrazol-5-yl}-methyl)-quinolin-8-ol | 435.27 | 435.26 | 457.25 | 457.24 | 2.2 |
| 13 | (3-Imidazol-1-yl-propyl)-((1H-indol-5-yl)-{1-[(S)-1-(tetrahydro-furan-2-yl)methyl]-1H-tetrazol-5-yl}-methyl)-amine | 407.27 | 407.28 | 429.25 | 0 | 6.7 |
| 14 | (3-Imidazol-1-yl-propyl)-(quinolin-2-yl-{1-[(S)-1-(tetrahydro-furan-2-yl)methyl]-1H-tetrazol-5-yl}-methyl)-amine | 419.27 | 419.27 | 441.25 | 0 | 2.2 |
| 15 | (Benzofuran-2-yl-{1-[(S)-1-(tetrahydro-furan-2-yl)methyl]-1H-tetrazol-5-yl}-methyl)-(3-imidazol-1-yl-propyl)-amine | 408.25 | 408.25 | 430.24 | 430.29 | 6.7 |
| 16 | (3-Imidazol-1-yl-propyl)-((6-methyl-1H-indol-3-yl)-{1-[(S)-1-(tetrahydro-furan-2-yl)methyl]-1H-tetrazol-5-yl}-methyl)-amine | 421.29 | 421.28 | 443.27 | 0 | 7.6 |
| 17 | (3-Imidazol-1-yl-propyl)-[{1-[(S)-1-(tetrahydro-furan-2-yl)methyl]-1H-tetrazol-5-yl}-(2,4,5-trimethyl-phenyl)-methyl]-amine | 410.32 | 410.31 | 432.3 | 0 | 4 |
| 18 | [(1-Butyl-1H-tetrazol-5-yl)-(3,4-dichloro-phenyl)-methyl]-(3-imidazol-1-yl-propyl)-amine | 408.18 | 408.19 | 430.16 | 0 | 7.6 |
| 19 | 2[(1-Butyl-1H-tetrazol-5-yl)-(3-imidazol-1-yl-propylamino)-mehtyl]-4-methyl-phenol | 370.28 | 370.27 | 392.26 | 0 | 2.2 |
| 20 | 2-[(1-Butyl-1H-tetrazol-5-yl)-(3-imidazol-1-yl- | 407.27 | 407.26 | 429.25 | 0 | 2.2 |

-continued

| | | | | | | |
|---|---|---|---|---|---|---|
| | propylamino)-methyl]-quinolin-8-ol | | | | | |
| 21 | [(1-Butyl-1H-tetrazol-5-yl)-(1H-indol-5-yl)-methyl]-(3-imidazol-1-yl-propyl)-amine | 379.28 | 379.27 | 401.26 | 0 | 6.7 |
| 22 | [(1-Butyl-1H-tetrazol-5-yl)-quinolin-2-yl-methyl]-(3-imidazol-1-yl-propyl)-amine | 391.28 | 391.27 | 413.26 | 413.29 | 3.1 |
| 23 | [Benzofuran-2-yl-(1-butyl-1H-tetrazol-5-yl)-methyl]-(3-imidazol-1-yl-propyl)-amine | 380.26 | 380.26 | 402.24 | 402.28 | 9.4 |
| 24 | [(1-Butyl-1H-tetrazol-5-yl)-(2,4,5-trimethyl-phenyl)-methy]-(3-imidazol-1-yl-propyl)-amine | 382.32 | 382.31 | 404.31 | 404.31 | 4.9 |
| 25 | 2-[(1-Cyclopentyl-1H-tetrazol-5-yl)-(3-imidazol-1-yl-propylamino)-methyl]-quinolin-8-ol | 419.27 | 0 | 441.25 | 0 | 2.2 |
| 26 | [(Cyclopentyl-1H-tetrazol-5-yl)-(1H-indol-5-yl)-methyl]-(3-imidazol-1-yl-propyl)-amine | 391.28 | 391.27 | 413.26 | 0 | 3.1 |
| 27 | [(1-Cyclopentyl-1H-tetrazol-5-yl)-((S)-2-methyl-cyclohex-2-enyl)-methyl]-(3-imidazol-1-yl-propyl)-amine | 370.33 | 0 | 392.31 | 0 | 6.7 |
| 28 | [(S)-(1-Cyclopentyl-1H-tetrazol-5-yl)-3,4-dihydro-2H-pyran-2-yl-methyl]-(3-imidazol-1-yl-propyl)-amine | 358.28 | 0 | 380.26 | 0 | 0.4 |
| 29 | 2-[(3-imidazol-1-yl-propylamino)-(1-methyl-1H-tetrazol-5-yl)-methyl]-quinolin-8-ol | 365.21 | 0 | 387.2 | 0 | 3.1 |
| 30 | (3-Imidazol-1-yl-propyl)-[(1H-indol-5-yl)-(1-methyl-1H-tetrazol-5-yl)-methyl]-amine | 337.22 | 337.22 | 359.2 | 0 | 4 |
| 31 | (3-Imidazol-1-yl-propyl)-[(1-methyl-1H-tetrazol-5-yl)-quinolin-2-yl-methyl]-amine | 349.22 | 349.24 | 371.2 | 0 | 4.9 |
| 32 | {(3,4-Dichloro-phenyl)-[1-(3-methoxy-propyl)-1H-tetrazol-5-yl]-methyl}-(3-imidazol-1-yl-propyl)-amine | 424.18 | 424.19 | 446.16 | 0 | 7.6 |
| 33 | 3-{(3-Imidazol-1-yl-propylamino)-[1-(3-methoxy- | 386.27 | 386.27 | 408.26 | 0 | 4 |

| | -continued | | | | | |
|---|---|---|---|---|---|---|
| | propyl)-1H-tetrazol-5-yl]-methyl}-4-methyl-phenol | | | | | |
| 34 | 2-{(3-Imidazol-1-yl-propylamino)-[1-(3-methoxy-propyl)-1H-tetrazol-5-yl]-methyl}-quinolin-8-ol | 423.27 | 423.27 | 445.25 | 0 | 2.2 |
| 35 | (3-Imidazol-1-yl-propyl)-{(1H-indol-5-yl)-[1-(3-methoxy-propyl)-1H-tetrazol-5-yl]-methyl}-amine | 395.27 | 395.27 | 417.25 | 0 | 7.6 |
| 36 | (3-Imidazol-1-yl-propyl)-{[1-(3-methoxy-propyl)-1H-tetrazol-5-yl]-quinolin-2-yl-methyl}-amine | 407.27 | 407.27 | 429.25 | 0 | 3.1 |
| 37 | 2-[[1-(2-Dimethylamino-ethyl)-1H-tetrazol-5-yl]-(3-imidazol-1-yl-propylamino)-methyl]-quinolin-8-ol | 422.28 | 0 | 444.27 | 0 | 4.9 |
| 38 | {(S)-3,4-Dihydro-2H-pyran-2-yl[1-(2-dimethylamino-ethyl)-1H-tetrazol-5-yl]-methyl}-(3-imidazol-1-yl-propyl)-amine | 361.29 | 0 | 383.28 | 0 | 0.4 |
| 39 | 2-{(3-Imidazol-1-yl-propylamino)-[1-(2-methoxy-ethyl)-1H-tetrazol-5-yl]-methyl}-4-methyl-phenol | 372.26 | 372.25 | 394.24 | 0 | 8.5 |
| 40 | 2-{(3-Imidazol-1-yl-propylamino)-[1-(2-methoxy-ethyl)-1H-tetrazol-5-yl]-methyl}-quinolin-8-ol | 409.25 | 409.25 | 431.23 | 0 | 3.1 |
| 41 | (3-Imidazol-1-yl-propyl)-{(1H-indol-5-yl)-[1-(2-methoxy-ethyl)-1H-tetrazol-5-yl]-methyl}-amine | 381.25 | 381.26 | 403.23 | 0 | 4.9 |
| 42 | (3-Imidazol-1-yl-propyl)-{[1-(2-methoxy-ethyl)-1H-tetrazol-5-yl]-quinolin-2-yl-methyl}-amine | 393.25 | 393.26 | 415.23 | 0 | 5.8 |
| 43 | (3-Imidazol-1-yl-propyl)-[[1-(2-methoxy-ethyl)-1H-tetrazol-5-yl]-(2,4,5-trimethyl-phenyl)-methyl]-amine | 384.3 | 384.3 | 406.28 | 0 | 7.6 |
| 44 | 2-[(1-Allyl-1H-tetrazol-5-yl)-(3-imidazol-1-yl-propylamino)-methyl]-4-methyl-phenol | 354.24 | 354.24 | 376.22 | 0 | 4.9 |
| 45 | 2-[(1-Allyl-1H-tetrazol-5-yl)-(3-imidazol-1-yl-propylamino)- | 391.23 | 391.24 | 413.21 | 0 | 4 |

|    |                                                                                                          |        |        |        |        |     |
|----|----------------------------------------------------------------------------------------------------------|--------|--------|--------|--------|-----|
|    | methyl]-quinolin-8-ol                                                                                    |        |        |        |        |     |
| 46 | [(1-Allyl-1H-tetrazol-5-yl)-(1H-indol-5-yl)-methyl]-(3-imidazol-1-yl-propyl)-amine                       | 363.24 | 363.25 | 385.22 | 0      | 7.6 |
| 47 | [(1-Allyl-1H-tetrazol-5-yl)-quinolin-2-yl-methyl]-(3-imidazol-1-yl-propyl)-amine                         | 375.24 | 375.24 | 397.22 | 0      | 3.1 |
| 48 | [(1-Allyl-1H-tetrazol-5-yl)-(2,4,5-trimethyl-phenyl)-methyl]-(3-imidazol-1-yl-propyl)-amine              | 366.29 | 366.26 | 388.27 | 0      | 9.4 |
| 49 | {5-[1-(3-Imidazol-1-yl-propylamino)-cyclobutyl]-tetrazol-1-yl}-acetic methyl ester                       | 320.22 | 320.21 | 342.2  | 0      | 0.4 |
| 50 | {5-[(3,4-Dichloro-phenyl)-(3-imidazol-1-yl-propylamino)-methyl]-tetrazol-1-yl}-acetic methyl ester       | 424.13 | 424.15 | 446.11 | 0      | 4   |
| 51 | {5-[(2-Hydroxy-5-methyl-phenyl)-(3-imidazol-1-yl-propylamino)-methyl]-tetrazol-1-yl}-acetic methyl ester | 386.23 | 386.25 | 408.21 | 0      | 2.2 |
| 52 | {5-[(8-Hydroxy-quinolin-2-yl)-(3-imidazol-1-yl-propylamino)-methyl]-tetrazol-1-yl}-acetic methyl ester   | 423.22 | 423.23 | 445.2  | 0      | 4.9 |
| 53 | {5-[(3-Cyano-4-fluoro-phenyl)-(3-imidazol-1-yl-propylamino)-methyl]-tetrazol-1-yl}-acetic methyl ester   | 399.2  | 399.21 | 421.18 | 421.22 | 4   |
| 54 | {5-[(3-Imidazol-1-yl-propylamino)-(1H-indol-5-yl)-methyl]-tetrazol-1-yl}-acetic methyl ester             | 395.23 | 0      | 417.21 | 0      | 5.8 |
| 55 | {5-[(3-Imidazol-1-yl-propylamino)-quinolin-2-yl-methyl]-tetrazol-1-yl}-acetic methyl ester               | 407.23 | 407.24 | 429.21 | 0      | 2.2 |
| 56 | {5-[(S)-3,4-Dihydro-2H-pyran-2-yl-(3-imidazol-1-yl-propylamino)-methyl]-tetrazol-1-yl}-acetic methyl ester | 362.23 | 362.23 | 384.21 | 0      | 4.9 |
| 57 | {5-[Cyclopropyl-(3-imidazol-1-yl-propylamino)-                                                           | 320.22 | 0      | 342.2  | 0      | 0.4 |

| | -continued | | | | | |
|---|---|---|---|---|---|---|
| | methyl]-tetrazol-1-yl}-acetic methyl ester | | | | | |
| 58 | {5-[(3-Hydroxy-4-methoxy-phenyl)-(3-imidazol-1-yl-propylamino)-methyl]-tetrazol-1-yl}-acetic methyl ester | 402.22 | 0 | 424.21 | 0 | 4 |
| 59 | 2-[(1-tert-Butyl-1H-tetrazol-5-yl)-(3-imidazol-1-yl-propylamino)-methyl]-4-methyl-phenol | 370.28 | 370.27 | 392.26 | 0 | 1.3 |
| 60 | 2-[(1-tert-Butyl-1H-tetrazol-5-yl)-(3-imidazol-1-yl-propylamino)-methyl]-quinolin-8-ol | 407.27 | 407.27 | 429.25 | 0 | 0.4 |
| 61 | [(S)-(1-tert-Butyl-1H-tetrazol-5-yl)-3,4-dihydro-2H-pyran-2-yl-methyl]-(3-imidazol-1-yl-propyl)-amine | 346.28 | 346.27 | 368.26 | 0 | 6.7 |
| 62 | [(1-tert-Butyl-1H-tetrazol-5-yl)-(2,4-dimethoxy-pyrimidin-5-yl)-methyl]-(3-imidazol-1-yl-propyl)-amine | 402.28 | 402.28 | 424.26 | 0 | 8.5 |
| 63 | 2-[[1-(2,2-Dimethyl-propyl)-1H-tetrazol-5-yl]-(3-imidazol-1-yl-propylamino)-methyl]-4-methyl-phenol | 384.3 | 384.3 | 406.28 | 0 | 0.04 |
| 64 | 2-[[1-(2,2-Dimethyl-propyl)-1H-tetrazol-5-yl]-(3-imidazol-1-yl-propylamino)-methyl]-quinolin-8-ol | 421.29 | 421.29 | 443.27 | 443.29 | 0.4 |
| 65 | [[1-(2,2-Dimethyl-propyl)-1H-tetrazol-5-yl]-(1H-indol-5-yl)-methyl]-(3-imidazol-1-yl-propyl)-amine | 393.3 | 393.3 | 415.28 | 0 | 4.9 |
| 66 | {[1-(2,2-Dimethyl-propyl)-1H-tetrazol-5-yl]-quinolin-2-yl-methyl}-(3-imidazol-1-yl-propyl)-amine | 405.3 | 405.3 | 427.28 | 0 | 3.1 |
| 67 | {(S)-3,4-Dihydro-2H-pyran-2-yl[1-(2,2-dimethyl-propyl)-1H-tetrazol-5-yl]-methyl}-(3-imidazol-1-yl-propyl)-amine | 360.3 | 360.29 | 382.28 | 0 | 6.7 |
| 68 | 2-[(1-Cyclopropyl-1H-tetrazol-5-yl)-(3-imidazol-1-yl-propylamino)-methyl]-4-methyl-phenol | 354.24 | 354.16 | 376.22 | 376.27 | 0.4 |

| | -continued | | | | | |
|---|---|---|---|---|---|---|
| 69 | [(1-Cyclopropyl-1H-tetrazol-5-yl)-(1H-indol-5-yl)-methyl]-(3-imidazol-1-yl-propyl)-amine | 363.24 | 363.24 | 385.22 | 0 | 4.9 |
| 70 | [(1-Cyclopropyl-1H-tetrazol-5-yl)-quinolin-2-yl-methyl]-(3-imidazol-1-yl-propyl)-amine | 375.24 | 375.25 | 397.22 | 0 | 5.8 |
| 71 | [(S)-(1-Cyclopropyl-1H-tetrazol-5-yl)-3,4-dihydro-2H-pyran-2-yl-methyl]-(3-imidazol-1-yl-propyl)-amine | 330.24 | 330.24 | 352.22 | 0 | 9.4 |
| 72 | (1H-Benzoimidazol-5-yl)-[(1-cyclohexyl-1H-tetrazol-5-yl)-(4-methoxy-phenyl)-methyl]-amine | 404.26 | 404.24 | 426.24 | 426.21 | 2.2 |
| 73 | (1H-Benzoimidazol-5-yl)-[2-phenyl-1-(1-pyridin-3-ylmethyl-1H-tetrazol-5-yl)-ethyl]-amine | 397.22 | 397.21 | 419.2 | 0 | 5.8 |
| 74 | (1H-Benzoimidazol-5-yl)-[(3-propoxy-phenyl)-(1-pyridin-3-ylmethyl-1H-tetrazol-5-yl)-methyl]-amine | 441.25 | 441.24 | 463.23 | 0 | 2.2 |
| 75 | (1H-Benzoimidazol-5-yl)-[[1-(4-chloro-benzyl)-1H-tetrazol-5-yl]-(4-methoxy-2-methyl-phenyl)-methyl]-amine | 460.2 | 460.19 | 482.18 | 0 | 2.2 |
| 76 | (1H-Benzoimidazol-5-yl)-{(4-pyridin-2-yl-phenyl)-[1-(tetrahydro-furan-2-ylmethyl)-1H-tetrazol-5-yl]-methyl}-amine | 453.25 | 453.24 | 475.23 | 0 | 3.1 |
| 77 | (1H-Benzoimidazol-5-yl)-[[1-(2-chloro-benzyl)-1H-tetrazol-5-yl]-(4-methoxy-2-methyl-phenyl)-methyl]-amine | 460.2 | 460.19 | 482.18 | 0 | 1.3 |
| 78 | {Benzo[b]thiophen-3-yl[1-(tetrahydro-furan-2-ylmethyl)-1H-tetrazol-5-yl]-methyl}-(1H-benzoimidazol-5-yl)-amine | 432.19 | 432.19 | 454.17 | 0 | 1.3 |
| 79 | [Benzofuran-2-yl-(1-cyclohexyl-1H-tetrazol-5-yl)-methyl]-(1H-benzoimidazol-5-yl)-amine | 414.24 | 414.23 | 436.22 | 0 | 3.1 |

| | -continued | | | | | |
|---|---|---|---|---|---|---|
| 80 | (1H-Benzoimidazol-5-yl)-{(6-methyl-1H-indol-3-yl)-[1-(tetrahydro-furan-2-ylmethyl)-1H-tetrazol-5-yl]-methyl}-amine | 429.25 | 429.24 | 451.23 | 0 | 6.7 |
| 81 | (1H-Benzoimidazol-5-yl)-[(1-cyclohexyl-1H-tetrazol-5-yl)-(6-fluoro-1H-indol-3-yl)-methyl]-amine | 431.24 | 431.23 | 453.23 | 0 | 3.1 |
| 82 | (1H-Benzoimidazol-5-yl)-[(4-ethyl-phenyl)-(1-pyridin-3-ylmethyl-1H-tetrazol-5-yl)-methyl]-amine | 411.24 | 411.23 | 433.22 | 0 | 4 |
| 83 | (1H-Benzoimidazol-5-yl)-{(3,4-dimethyl-phenyl)-[1-(tetrahydro-furan-2-ylmethyl)-1H-tetrazol-5-yl]-methyl}-amine | 404.26 | 404.25 | 426.24 | 0 | 4.9 |
| 84 | 2-{5-[(1H-Benzoimidazol-5-ylamino)-(4-chloro-3-fluoro-phenyl)-methyl]-tetrazol-1-yl}-cyclohexanecarboxylic acid ethyl ester | 498.22 | 498.23 | 520.2 | 0 | 6.7 |
| 85 | 3-{(1H-Benzoimidazol-5-ylamino)-[1-(4-chloro-benzyl)-1H-tetrazol-5-yl]-methyl}-benzoic acid methyl ester | 474.17 | 474.18 | 496.15 | 0 | 1.3 |
| 86 | 3-{(1H-Benzoimidazol-5-ylamino)-[1-(tetrahydro-furan-2-ylmethyl)-1H-tetrazol-5-yl]-methyl}-6-methyl-chromen-4-one | 458.23 | 458.23 | 480.21 | 0 | 9.4 |
| 87 | {5-[(1H-Benzoimidazol-5-ylamino)-(4-bromo-phenyl)-methyl]-tetrazol-1-yl}-acetic acid tert-butyl ester | 484.14 | 484.14 | 506.12 | 0 | 1.3 |
| 88 | (1H-Benzoimidazol-5-yl)-{(4-methoxy-phenyl)-[1-(tetrahydro-furan-2-ylmethyl)-1H-tetrazol-5-yl]-methyl}-amine | 406.23 | 406.22 | 428.22 | 428.21 | 4.9 |
| 89 | (1H-Benzoimidazol-5-yl)-{(3-methoxy-phenyl)-[1-(tetrahydro-furan-2-ylmethyl)-1H-tetrazol-5-yl]-methyl}-amine | 406.23 | 406.23 | 428.22 | 428.2 | 7.6 |

| | | -continued | | | | |
|---|---|---|---|---|---|---|
| 90 | {Benzofuran-2-yl-[1-(2-chloro-benzyl)-1H-tetrazol-5-yl]-methyl}-(1H-benzoimidazol-5-yl)-amine | 456.16 | 456.17 | 478.14 | 0 | 22.2 |
| 91 | {5-[(1H-Benzoimidazol-5-ylamino)-(4-chloro-3-fluoro-phenyl)-methyl]-tetrazol-11-yl}-acetic acid tert-butyl ester | 458.18 | 458.18 | 480.16 | 0 | 4 |
| 92 | (1H-Benzoimidazol-5-yl)-{(2E,4E)-1-[1-(2,2-dimethyl-[1,3]dioxolan-4-ylmethyl)-1H-tetrazol-5-yl]-hexa-2,4-dienyl}-amine | 396.25 | 396.24 | 418.24 | 0 | 4.9 |
| 93 | {3-Benzo[1,3]dioxol-5-yl-2-methyl-1-[1-(tetrahydro-furan-2-ylmethyl)-1H-tetrazol-5-yl]-propyl}-(1H-benzoimidazol-5-yl)-amine | 462.27 | 462.26 | 484.25 | 0 | 7.6 |
| 94 | 2-{5-[(1H-Benzoimidazol-5-ylamino)-(4-chloro-phenyl)-methyl]-tetrazol-1-yl}-cyclohexanecarboxylic acid ethyl ester | 480.23 | 480.22 | 502.21 | 0 | 9.4 |
| 95 | [1-(1-Benzhydryl-1H-tetrazol-5-yl)-3-methylsulfanyl-propyl]-(1H-benzoimidazol-5-yl)-amine | 456.23 | 456.22 | 478.22 | 0 | 4.9 |
| 96 | (1H-Benzoimidazol-5-yl)-[1-(1-cyclohexyl-1H-tetrazol-5-yl)-3-(5-methyl-furan-2-yl)-butyl]-amine | 420.3 | 420.28 | 442.28 | 0 | 4.9 |
| 97 | (1H-Benzoimidazol-5-yl)-{3-phenyl-1-[1-(tetrahydro-furan-2-ylmethyl)-1H-tetrazol-5-yl]-butyl}-amine | 418.28 | 418.27 | 440.26 | 0 | 4 |
| 98 | 2-{5-[1-(1H-Benzoimidazol-5-ylamino)-2-methyl-pentyl]-tetrazol-1-yl}-1-(3,4-dihydro-1H-isoquinolin-2-yl)-ethanone | 459.31 | 459.3 | 481.29 | 0 | 6.7 |
| 99 | (1H-Benzoimidazol-5-yl)-[(1-tert-butyl-1H-tetrazol-5-yl)-(4-methoxy-2,5-dimethyl-pentyl)-methyl]-amine | 406.28 | 406.26 | 428.26 | 0 | 8.5 |

| | | | | | | |
|---|---|---|---|---|---|---|
| 100 | (1H-Benzoimidazol-5-yl)-{2-phenyl-1-[1-(tetrahydro-furan-2-ylmethyl)-1H-tetrazol-5-yl]-propyl}-amine | 404.26 | 404.24 | 426.24 | 0 | 7.6 |
| 101 | {Benzofuran-2-yl-[1-(tetrahydro-furan-2-ylmethyl)-1H-tetrazol-5-yl]-methyl}-(1H-benzoimidazol-5-yl)-amine | 416.21 | 416.22 | 438.2 | 0 | 4.9 |
| 102 | (1H-Benzoimidazol-5-yl)-{quinolin-3-yl-[1-(tetrahydro-furan-2-ylmethyl)-1H-tetrazol-5-yl]-methyl}-amine | 427.23 | 427.22 | 449.21 | 0 | 2.2 |
| 103 | 2-{5-[(1H-Benzoimidazol-5-ylamino)-(4-bromo-phenyl)-methyl]-tetrazol-1-yl}-cyclohexanecarboxylic acid ethyl ester | 524.18 | 524.18 | 546.16 | 0 | 4.9 |
| 104 | 2{(1H-Benzoimidazol-5-ylamino)-[1-(2-thiophen-2-yl-ethyl)-1H-tetrazol-5-yl]-methyl}-cyclopropanecarboxylic acid ethyl ester | 438.21 | 438.2 | 460.19 | 0 | 4 |
| 105 | (1H-Benzoimidazol-5-yl)-[benzo[c][1,2,5]-thiadiazol-5-yl-[1-(tetrahydro-furan-2-ylmethyl)-1H-tetrazol-5-yl]-methyl]-amine | 434.18 | 434.18 | 456.16 | 0 | 4.9 |
| 106 | (1H-Benzoimidazol-5-yl)-[1-(1-tert-butyl-1H-tetrazol-5-yl)-3-phenyl-butyl]-amine | 390.28 | 390.27 | 412.27 | 0 | 6.7 |
| 107 | (1H-Benzoimidazol-5-yl)-[(4-chloro-3-fluoro-phenyl)-(1-cyclohexyl-1H-tetrazol-5-yl)-methyl]-amine | 426.19 | 426.19 | 448.17 | 0 | 4.9 |
| 108 | (1H-Benzoimidazol-5-yl)-{(4-dimethylamino-phenyl)-[1-(tetrahydro-furan-2-ylmethyl)-1H-tetrazol-5-yl]-methyl}-amine | 419.27 | 419.26 | 441.25 | 0 | 5.8 |
| 109 | (1H-Benzoimidazol-5-yl)-{(3-bromo-4-methoxy-phenyl)-[1-(tetrahydro-furan-2-ylmethyl)-1H-tetrazol-5-yl]-methyl}-amine | 484.14 | 484.14 | 506.12 | 0 | 1.3 |

| | | | | | | |
|---|---|---|---|---|---|---|
| 110 | (1H-Benzoimidazol-5-yl)-[1-(1-benzyl-1H-tetrazol-5-yl)-butyl]-amine | 348.23 | 348.21 | 370.21 | 370.2 | 5.8 |
| 111 | (1H-Benzoimidazol-5-yl)-{3-(5-methyl-furan-2-yl)-1-[1-(tetrahydro-furan-2-ylmethyl)-1H-tetrazol-5-yl]-butyl}-amine | 422.27 | 422.25 | 444.26 | 444.24 | 5.8 |
| 112 | [(1-Benzhydryl-1H-tetrazol-5-yl)-benzo[c][1,2,5]thia-diazol-5-yl-methyl]-(1H-benzoimidazol-5-yl)-amine | 516.2 | 516.22 | 538.18 | 538.19 | 5.8 |
| 113 | {3-Benzo[1,3]dioxol-5-yl-1-[1-92-chloro-benzyl)-1H-tetrazol-5-yl]-2-methyl-propyl}-(1H-benzoimidazol-5-yl)-amine | 502.21 | 502.21 | 524.19 | 0 | 3.1 |
| 114 | (1H-Benzoimidazol-5-yl)[(1-cyclohexyl-1H-tetrazol-5-yl)-(3,4-dihydro-2H-pyran-2-yl)-methyl]-amine | 380.26 | 380.25 | 402.24 | 402.25 | 6.7 |
| 115 | (1H-Benzoimidazol-5-yl)-[(4-dimethylamino-phenyl)-(1-pyridin-3-ylmethyl-1H-tetrazol-5-yl)-methyl]-amine | 426.25 | 426.24 | 448.23 | 0 | 5.8 |
| 116 | [3-Benzo[1,3]dioxol-5-yl-1-(1-cyclohexyl-1H-tetrazol-5-yl)-2-methyl-propyl]-(1H-benzoimidazol-5-yl)-amine | 460.29 | 460.28 | 482.27 | 0 | 7.6 |
| 117 | (1H-Benzoimidazol-5-yl)-{benzo[c][1,2,5]thiadiazol-5-yl-[1-(4-tert-butyl-phenyl)-1H-tetrazol-5-yl]-methyl}-amine | 482.22 | 482.23 | 504.2 | 0 | 4 |
| 118 | {Benzo[1,3]dioxol-5-yl[1-(tetrahydro-furan-2-ylmethyl)-1H-tetrazol-5-yl]-methyl}-(1H-benzoimidazol-5-yl)-amine | 420.21 | 420.21 | 442.19 | 0 | 6.7 |
| 119 | {5-[Benzo[1,3]dioxol-5-yl-(1H-benzoimidazol-5-ylamino)-methyl]-tetrazol-1-yl}-acetic acid tert-butyl ester | 450.22 | 450.23 | 472.2 | 0 | 2.2 |

-continued

| | | | | | | |
|---|---|---|---|---|---|---|
| 120 | 2-{5-[(1H-Benzoimidazol-5-ylamino)-thiophen-2-yl-methyl]-tetrazol-1-yl}-1-(3,4-dihydro-1H-isoquinolin-2-yl)-ethanone | 471.2 | 471.2 | 493.18 | 0 | 8.5 |
| 121 | (5-{(1H-Benzoimidazol-5-ylamino)-[1-(4-chloro-benzyl)-1H-tetrazol-5-yl]-methyl}-furan-2-yl)-methanol | 436.15 | 436.16 | 458.13 | 0 | 4.9 |
| 122 | 3-{(1H-Benzoimidazol-5-ylamino)-[1-(2-thiophen-2-yl-ethyl)-1H-tetrazol-5-yl]-methyl}-chromen-4-one | 470.16 | 470.17 | 492.15 | 0 | 4.9 |
| 123 | [Benzo-[b]thiophen-3-yl-(1-tert-butyl-1H-tetrazol-5-yl)-methyl]-(1H-benzoimidazol-5-yl)-amine | 404.2 | 404.2 | 426.18 | 0 | 8.5 |
| 124 | (1H-Benzoimidazol-5-yl)-[(1-benzyl-1H-tetrazol-5-yl)-(3,5-dimethyl-phenyl)-methyl]-amine | 410.24 | 410.25 | 432.23 | 432.25 | 5.8 |
| 125 | (1H-Benzoimidazol-5-yl)-[[1-(4-chloro-benzyl)-1H-tetrazol-5-yl]-(3-fluoro-4-methoxy-phenyl)-methyl]-amine | 464.16 | 464.18 | 486.15 | 0 | 3.1 |
| 126 | [(1-Benzhydryl-1H-tetrazol-5-yl)-quinolin-3-yl-methyl]-(1H-benzoimidazol-5-yl)-amine | 509.25 | 509.26 | 531.23 | 0 | 4.9 |
| 127 | (1H-Benzoimidazol-5-yl)-[[1-(2-chloro-benzyl)-1H-tetrazol-5-yl]-(4-chloro-phenyl)-methyl]-amine | 450.12 | 450.14 | 472.1 | 0 | 3.1 |
| 128 | 3-{(1H-Benzoimidazol-5-ylamino)-[1-(4-tert-butyl-phenyl)-1H-tetrazol-5-yl]-methyl}-benzoic acid methyl ester | 482.27 | 482.27 | 504.25 | 504.24 | 6.7 |
| 129 | (1H-Benzoimidazol-5-yl)-{(5-ethyl-thiophen-2-yl)-[1-(tetrahydro-furan-2-ylmethyl)-1H-tetrazol-5-yl]-methyl}-amine | 410.21 | 410.21 | 432.19 | 0 | 8.5 |
| 130 | (1H-Benzoimidazol-5-yl)-[[1-(2,2-dimethyl-[1,3]dioxolan-4-ylmethyl)-1H- | 452.22 | 452.23 | 474.21 | 0 | 7.6 |

-continued

| | | | | | | |
|---|---|---|---|---|---|---|
| | tetrazol-5-yl]-(4-methylsulfanyl-phenyl)-methyl]-amine | | | | | |
| 131 | 4-{(1H-Benzoimidazol-5-ylamino)-[1-(tetrahydro-furan-2-ylmethyl)-1H-tetrazol-5-yl]-methyl}-2,6-dimethyl-phenol | 420.25 | 420.25 | 442.24 | 0 | 6.7 |
| 132 | 2-{5-[(1H-Benzoimidazol-5-ylamino)-(3-fluoro-4-methoxy-phenyl)-methyl]-tetrazol-1-yl}-cyclohexanecarboxylic acid ethyl ester | 494.27 | 494.28 | 516.26 | 0 | 8.5 |
| 133 | (1H-Benzoimidazol-5-yl)-[(1-benzyl-1H-tetrazol-5-yl)-(5-ethyl-thiophen-2-yl)-methyl]-amine | 416.2 | 416.2 | 438.18 | 0 | 3.1 |
| 134 | (1H-Benzoimidazol-5-yl)-{(4-pyrolidin-1-yl-phenyl)-[1-(tetrahydro-furan-2-ylmethyl)-1H-tetrazol-5-yl]-methyl}-amine | 445.29 | 445.28 | 467.27 | 0 | 6.7 |
| 135 | (1H-Benzoimidazol-5-yl)-{[1-(2-chloro-benzyl)-1H-tetrazol-5-yl]-pyridin-3-yl-methyl}-amine | 417.16 | 417.16 | 439.14 | 0 | 8.5 |
| 136 | (1H-Benzoimidazol-5-yl)-[[1-(4-chloro-benzyl)-1H-tetrazol-5-yl]-(4-chloro-phenyl)-methyl]-amine | 450.12 | 450.14 | 472.1 | 0 | 4 |
| 137 | 2-{5-[(1H-Benzoimidazol-5-ylamino)-(3,5-dimethyl-phenyl)-methyl]-tetrazol-1-yl}-1-(3,4-dihydro-1H-isoquinolin-2-yl)-ethanone | 493.29 | 493.28 | 515.27 | 0 | 4.9 |
| 138 | {Benzo[1,3]dioxol-5-yl-[1-(2,2-dimethyl-[1,3]dioxolan-4-ylmethyl)-1H-tetrazol-5-yl]-methyl}-(1H-benzoimidazol-5-yl)-amine | 450.22 | 450.23 | 472.2 | 0 | 9.4 |
| 139 | {Benzo[1,3]dioxol-5-yl-[1-(4-phenoxy-phenyl)-1H-tetrazol-5-yl]-methyl}-(1H-benzoimidazol-5-yl)-amine | 504.2 | 504.22 | 526.19 | 0 | 4 |
| 140 | (1H-Benzoimidazol-5-yl)-{(4-methylsulfanyl-phenyl)-[1-(tetrahydro-furan- | 422.21 | 422.2 | 444.19 | 0 | 6.7 |

-continued

| | | | | | | |
|---|---|---|---|---|---|---|
| | 2-ylmethyl)-1H-tetrazol-5-yl]-methyl}-amine | | | | | |
| 141 | (1H-Benzoimidazol-5-yl)-{(3-propoxy-phenyl)-[1-(tetrahydro-furan-2-ylmethyl)-1H-tetrazol-5-yl]-methyl}-amine | 434.27 | 434.25 | 456.25 | 0 | 4 |
| 142 | (1H-Benzoimidazol-5-yl)-[(3-bromo-4-methoxy-phenyl)-(1-pyridin-3-ylmethyl-1H-tetrazol-5-yl)-methyl]-amine | 491.12 | 491.12 | 513.1 | 0 | 0.4 |
| 143 | (5-{(1H-Benzoimidazol-5-ylamino)-[1-(2-benzyloxy-phenyl)-1H-tetrazol-5-yl]-methyl}-furan-2-yl)-methanol | 494.23 | 494.22 | 516.21 | 0 | 4.9 |
| 144 | (1H-Benzoimidazol-5-yl)-{(6-fluoro-1H-indol-3-yl)-[1-(tetrahydro-furan-2-ylmethyl)-1H-tetrazol-5-yl]-methyl}-amine | 433.22 | 433.21 | 455.2 | 0 | 5.8 |
| 145 | 2-{5-[Benzo[b]thiophen-3-yl-(1H-benzoimidazol-5-ylamino)-methyl]-tetrazol-1-yl}-cyclohexanecarboxylic acid ethyl ester | 502.24 | 502.24 | 524.22 | 524.21 | 1.3 |
| 146 | (1H-Benzoimidazol-5-yl)-{(4-chloro-3-nitro-phenyl)-[1-(tetrahydro-furan-2-ylmethyl)-1H-tetrazol-5-yl]-methyl}amine | 455.16 | 455.16 | 477.14 | 0 | 3.1 |
| 147 | (1H-Benzoimidazol-5-yl)-[benzo[c][1,2,5]thiadiazol-5-yl-(1-benzyl-1H-tetrazol-5-yl)-methyl]-amine | 440.16 | 440.17 | 462.14 | 0 | 1.3 |
| 148 | (1H-Benzoimidazol-5-yl)-[[1-(2-chloro-benzyl)-1H-tetrazol-5-yl]-(4-chloro-3-nitro-phenyl)-methyl]-amine | 495.1 | 495.12 | 517.08 | 0 | 1.3 |
| 149 | {5-[3-Benzo[1,3]dioxol-5-yl-1-(1H-benzoimidazol-5-ylamino)-2-methyl-propyl]-tetrazol-1-yl}-acetic acid tert-butyl ester | 492.28 | 492.27 | 514.26 | 514.26 | 4.9 |
| 150 | 2-{5-[(1H-Benzoimidazol-5- | 492.26 | 492.26 | 514.25 | 514.24 | 4 |

-continued

| | | | | | | |
|---|---|---|---|---|---|---|
| | ylamino)-(4-methylsulfanyl-phenyl)-methyl]-tetrazol-1-yl}-cyclohexanecarboxylic acid ethyl ester | | | | | |
| 151 | (1H-Benzoimidazol-5-yl-[(1-benzyl-1H-tetrazol-5-yl)-(2-methoxy-phenyl)-methyl]-amine | 412.22 | 412.2 | 434.2 | 0 | 5.8 |
| 152 | 3-{(1H-Benzoimidazol-5-ylamino)[1-(tetrahydro-furan-2-ylmethyl)-1H-tetrazol-5-yl]-methyl}-phenol | 392.21 | 392.21 | 414.2 | 0 | 9.4 |
| 153 | (1H-Benzoimidazol-5-yl)-[[1-(2-chloro-benzyl)-1H-tetrazol-5-yl](2-methoxy-phenyl)-methyl]-amine | 446.18 | 446.19 | 468.16 | 0 | 3.1 |
| 154 | 3-{(1H-Benzoimidazol-5-ylamino)-[1-(tetrahydro-furan-2-ylmethyl)-1H-tetrazol-5-yl]-methyl}-benzoic acid methyl ester | 434.23 | 434.23 | 456.21 | 456.23 | 5.8 |
| 155 | 2-{5-[(1H-Benzoimidazol-5-ylamino)-(3,4-dimethyl-phenyl)-methyl]-tetrazol-1-yl}-cyclohexanecarboxylic acid ethyl ester | 474.31 | 474.3 | 496.29 | 496.29 | 4.9 |
| 156 | (1H-Benzoimidazol-5-yl)-{[1-(2,2-dimethyl-[1,3]dioxolan-4-ylmethyl)-1H-tetrazol-5-yl]-quinolin-3-yl-methyl}-amine | 457.24 | 457.24 | 479.23 | 0 | 4.9 |
| 157 | 2-{5-[(1H)-Benzoimidazol-5-ylamino)-(3,5-dimethyl-phenyl)-methyl]-tetrazol-1-yl}-cyclohexanecarboxylic acid ethyl ester | 474.31 | 474.3 | 496.29 | 496.27 | 5.8 |
| 158 | [(1-Benzhydryl-1H-tetrazol-5-yl)-pyridin-3-yl-methyl]-(1H-benzoimidazol-5-yl)-amine | 459.23 | 459.24 | 481.22 | 0 | 9.4 |
| 159 | 3-{(1H-Benzoimidazol-5-ylamino)-[1-(tetrahydro-furan-2-ylmethyl)-1H-tetrazol-5-yl]-mthyl}-chromen-4-one | 444.21 | 444.21 | 466.19 | 0 | 9.4 |
| 160 | {Benzo[1,3]dioxol-5-yl-[1-(4-chloro-benzyl)-1H- | 460.15 | 460.17 | 482.23 | 0 | 0.4 |

| | | | | | | |
|---|---|---|---|---|---|---|
| | tetrazol-5-yl]-methyl}-(1H-benzoimidazol-5-yl)-amine | | | | | |
| 161 | (1H-Benzoimidazol-5-yl)-{(2E,4E)-1-[1-(2-thiophen-2-yl-ethyl)-1H-tetrazol-5-yl]-hexa-2,4-dienyl}-amine | 392.2 | 392.19 | 414.18 | 0 | 5.8 |
| 162 | 2-{5-[benzo[1,3]dioxol-5-yl-(1H-benzoimidazol-5-ylamino)-methyl]-tetrazol-1-yl}-cyclohexanecarboxylic acid ethyl ester | 490.26 | 490.26 | 512.24 | 0 | 5.8 |
| 163 | (1H-Benzoimidazol-5-yl)-{(3-fluoro-4-methoxy-phenyl)-[1-(tetrahydro-furan-2-ylmethyl)-1H-tetrazol-5-yl]-methyl}-amine | 424.22 | 424.22 | 446.2 | 446.26 | 8.5 |
| 164 | 1-(3-{5-[(1H-Benzoimidazol-5-ylamino)-(3,4-dimethyl-phenyl)-methyl]-tetrazol-1-yl}-propyl)-pyrrolidin-2-one | 445.29 | 445.28 | 467.27 | 467.26 | 4.9 |
| 165 | 4-{(1H-Benzoimidazol-5-ylamino)-[1-(2,2-dimethyl-[1,3]dioxolan-4-ylmethyl)-1H-tetrazol-5-yl]-methyl}-2,6-dimethyl-phenol | 450.27 | 450.26 | 472.25 | 0 | 5.8 |
| 166 | (1H-Benzoimidazol-5-yl)-{benzo[c][1,2,5]thiadiazol-5-yl[1-(4-chloro-benzyl)-1H-tetrazol-5-yl]-methyl}-amine | 474.12 | 474.14 | 496.1 | 0 | 0.4 |
| 167 | (1H-Benzoimidazol-5-yl)-{cyclohex-3-enyl-[1-(2-thiophen-2-yl-ethyl)-1H-tetrazol-5-yl]-methyl}-amine | 406.22 | 406.21 | 428.2 | 0 | 8.5 |
| 168 | 2-{5-[(1H-Benzoimidazol-5-ylamino)-(4-ethyl-phenyl)-methyl]-tetrazol-1-yl}-cyclohexanecarboxylic acid ethyl ester | 474.31 | 474.3 | 496.29 | 496.27 | 5.8 |
| 169 | 2-{5-[(1H-Benzoimidazol-5-ylamino)-(5-chloro-2-hydroxy-phenyl)-methyl]-tetrazol-1-yl}-cyclohexacarboxylic acid ethyl ester | 496.23 | 496.21 | 518.21 | 0 | 7.6 |
| 170 | (1H-Benzoimidazol-5- | 532.04 | 532.04 | 554.02 | 0 | 4.9 |

| | | | | | | |
|---|---|---|---|---|---|---|
| | yl)-{(3,5-dibromo-phenyl)-[1-(tetrahydro-furan-2-ylmethyl)-1H-tetrazol-5-yl]-methyl}-amine | | | | | |
| 171 | (1H-Benzoimidazol-5-yl)-{(4-chloro-3-nitro-phenyl)-[1-(2,2-dimethyl-[1,3]dioxolan-4-ylmethyl)-1H-tetrazol-5-yl]-methyl}-amine | 485.17 | 485.18 | 507.16 | 0 | 8.5 |
| 172 | {5-[(1H-Benzoimidazol-5-ylamino)-(4-methoxy-phenyl)-methyl]-tetrazol-1-yl}-acetic acid tert-butyl ester | 436.25 | 436.25 | 458.23 | 0 | 4 |
| 173 | (1H-Benzoimidazol-5-yl)-[(2E,4E)-1-(1-pyridin-3-ylmethyl-1H-tetrazol-5-yl)-hexa-2,4-dienyl]-amine | 373.22 | 373.17 | 395.2 | 0 | 8.5 |
| 174 | (1H-Benzoimidazol-5-yl)-{(2E,4E)-1-[1-(tetrahydro-furan-2-ylmethyl)-1H-tetrazol-5-yl]-hexa-2,4-dienyl}-amine | 366.24 | 366.23 | 388.22 | 0 | 8.5 |
| 175 | (1H-Benzoimidazol-5-yl)-[(1-cyclohexyl-1H-tetrazol-5-yl)-(3,5-dibromo-phenyl)-methyl]-amine | 530.06 | 530.07 | 552.04 | 0 | 3.1 |
| 176 | 1-(3-{5-[(1H-Benzoimidazol-5-ylamino)-(3,5-dibromo-phenyl)-methyl]-tetrazol-1-yl}-propyl)-pyrrolidin-2-one | 573.07 | 573.08 | 595.05 | 0 | 5.8 |
| 177 | (1H-Benzoimidazol-5-yl)-{(3,5-dibromo-phenyl)-[1-(2-thiophen-2-yl-ethyl)-1H-tetrazol-5-yl]-methyl}-amine | 557.99 | 558.01 | 579.97 | 0 | 2.2 |
| 178 | (1H-Benzoimidazol-5-yl)-{(3,5-dibromo-phenyl)-[1-(4-phenoxy-phenyl)-1H-tetrazol-5-yl]-methyl}-amine | 616.03 | 616.06 | 638.01 | 0 | 5.8 |
| 179 | (1H-Benzoimidazol-5-yl)-{(3,5-dibromo-phenyl)-[1-(2,3-dihydro-benzo[1,4]dioxin-6-yl)-1H-tetrazol-5-yl]-methyl}-amine | 582.01 | 582.1 | 603.99 | 0 | 4 |
| 180 | (1H-Benzoimidazol-5-yl)-[[1-(2- | 630.05 | 630.08 | 652.03 | 0 | 4.9 |

-continued

| | | | | | | |
|---|---|---|---|---|---|---|
| | benzyloxy-phenyl)-1H-tetrazol-5-yl]-(3,5-dibromo-phenyl)-methyl]-amine | | | | | |
| 181 | (1H-Benzoimidazol-5-yl)-{benzo[c][1,2,5]thia-diazol-5-yl[1-(2-thiophen-2-yl-ethyl)-1H-tetrazol-5-yl]-methyl}-amine | 460.13 | 460.15 | 482.11 | 0 | 0.4 |
| 182 | (1H-Benzoimidazol-5-yl)-{(3,4-dihydro-2H-pyran-2-yl)-[1-(2-thiophen-2-yl-ethyl)-1H-tetrazol-5-yl]-methyl}-amine | 408.19 | 408.19 | 430.17 | 430.17 | 5.8 |
| 183 | 2-{5-[(1H-Benzoimidazol-5-ylamino)-(2-methoxy-phenyl)-methyl]-tetrazol-1-yl}-cyclohexanecar-boxylic acid ethyl ester | 476.29 | 476.28 | 498.27 | 498.24 | 8.5 |
| 184 | 2-{5-[(1H-Benzoimidazol-5-ylamino)-(4-methoxy-phenyl)-methyl]-tetrazol-1-yl}-cyclohexanecar-boxylic acid ethyl ester | 476.29 | 476.28 | 498.27 | 498.27 | 5.8 |
| 185 | (1H-Benzoimidazol-5-yl)-[benzo[c][1,2,5]thia-diazol-5-yl-(1-pyridin-3-ylmethyl-1H-tetrazol-5-yl)-methyl]-amine | 441.15 | 441.17 | 463.14 | 0 | 6.7 |
| 186 | [(1-Benzhydryl-1H-tetrazol-5-yl)-(3,5-dibromo-phenyl)-methyl]-(1H-benzoimidazol-5-yl)-amine | 614.06 | 614.07 | 636.04 | 0 | 5.8 |
| 187 | 2-{5-[(1H-Benzoimidazol-5-ylamino)-(3,5-dibromo-phenyl)-methyl]-tetrazol-1-yl}-N-[2-(1H-indol-3-yl)-ethyl]-acetamide | 648.08 | 648.1 | 670.06 | 0 | 1.3 |
| 188 | (1H-Benzoimidazol-5-yl)-{(3,5-dibromo-phenyl)-[1-(3,3-diphenyl-propyl)-1H-tetrazol-5-yl]-methyl}-amine | 642.1 | 642.12 | 664.08 | 0 | 4 |
| 189 | (1H-Benzoimidazol-5-yl)-{(3,5-dibromo-phenyl)-[1-(4-phenyl-butyl)-1H-tetrazol-5-yl]-methyl}-amine | 580.08 | 580.09 | 602.06 | 0 | 3.1 |

| | -continued | | | | | |
|---|---|---|---|---|---|---|
| 190 | (1H-Benzoimidazol-5-yl)-[(1-benzyl-1H-tetrazol-5-yl)-(3,5-dibromo-phenyl)-methyl]-amine | 538.02 | 538.04 | 560 | 0 | 1.3 |
| 191 | 4-{(1H-Benzoimidazol-5-ylamino)-[1-(4-chloro-benzyl)-1H-tetrazol-5-yl]-methyl}-phenol | 432.16 | 432.17 | 454.14 | 0 | 3.1 |
| 192 | 2-{5-[(1H-Benzoimidazol-5-ylamino)-(3-methoxy-phenyl)-methyl]-tetrazol-1-yl}-cyclohexanecarboxylic acid ethyl ester | 476.29 | 476.28 | 498.27 | 498.27 | 8.5 |
| 193 | 2-[(1H-Benzoimidazol-5-ylamino)-(1-cyclohexyl-1H-tetrazol-5-yl)-methyl]-4-chloro-phenol | 424.2 | 424.22 | 446.18 | 0 | 5.8 |
| 194 | 1-(3-{5-[(1H-Benzoimidazol-5-ylamino)-(4-bromo-phenyl)-methyl]-tetrazol-1-yl}-propyl)-pyrrolidn-2-one | 495.16 | 495.17 | 517.14 | 0 | 8.5 |
| 195 | 3-{(1H-Benzoimidazol-5-ylamino)-[1-(2-ethoxycarbonyl-cyclohexyl)-1H-tetrazol-5-yl]-methyl}-benzoic acid methyl ester | 504.28 | 504.28 | 526.26 | 526.27 | 5.8 |
| 196 | 2-{5-[(1H-Benzoimidazol-5-ylamino)-(6-methyl-1H-indol-3-yl)-methyl]-tetrazol-1-yl}-cyclohexanecarboxylic acid ethyl ester | 499.3 | 499.3 | 521.29 | 0 | 8.5 |
| 197 | (1H-Benzoimidazol-5-yl)-[[1-(4-chloro-benzyl)-1H-tetrazol-5-yl]-(4-chloro-3-nitro-phenyl)-methyl]-amine | 495.1 | 495.12 | 517.08 | 0 | 2.2 |
| 198 | (1H-Benzoimidazol-5-yl)-[(1-cyclohexyl-1H-tetrazol-5-yl)-(4-ethyl-phenyl)-methyl]-amine | 402.28 | 402.28 | 424.27 | 424.26 | 4.9 |
| 199 | 2-{5-[(1H-Benzoimidazol-5-ylamino)-(4-bromo-phenyl)-methyl]-tetrazol-1-yl}-1-(3,4-dihydro-1H-isoquinolin-2-yl)-ethanone | 543.16 | 543.16 | 565.14 | 0 | 2.2 |
| 200 | 2-{5-[(1H-Benzoimidazol-5-ylamino)-(4-bromo-phenyl)-methyl]-tetrazol-1- | 570.17 | 570.18 | 592.15 | 592.23 | 2.2 |

-continued

| | | | | | | |
|---|---|---|---|---|---|---|
| | yl}-N-[2-(1H-indol-3-yl)-ethyl]-acetamide | | | | | |
| 201 | (1H-Benzoimidazol-5-yl)-[(4-bromo-phenyl)-(1-pyridin-3-ylmethyl-1H-tetrazol-5-yl)-methyl]-amine | 461.11 | 461.12 | 483.09 | 0 | 4 |
| 202 | 2-{5-[1-(1H-Benzoimidazol-5-ylamino)-3-(5-methyl-furan-2-yl)-butyl]-tetrazol-1-yl}-cyclohexanecarboxylic acid ethyl ester | 492.33 | 492.31 | 514.31 | 0 | 6.7 |
| 203 | (1H-Benzoimidazol-5-yl)-[[1-(2-benzyloxy-phenyl)-1H-tetrazol-5-yl]-(4-bromo-phenyl)-methyl]-amine | 552.14 | 552.16 | 574.13 | 574.12 | 2.2 |
| 204 | (1H-Benzoimidazol-5-yl)-{1-[1-(4-phenoxy-phenyl)-1H-tetrazol-5-yl]-3-phenyl-butyl}-amine | 502.28 | 502.28 | 524.26 | 524.24 | 6.7 |
| 205 | (1H-Benzoimidazol-5-yl)-{benzo[c][1,2,5]thiadiazol-5-yl-[1-(2-chloro-benzyl)-1H-tetrazol-5-yl]-methyl}-amine | 474.112 | 474.14 | 496.1 | 0 | 2.2 |
| 206 | {Benzo[b]thiophen-3-yl-[1-(4-nitrophenyl)-1H-tetrazol-5-yl]-methyl}-(1H-benzoimidazol-5-yl)-amine | 469.14 | 469.14 | 491.12 | 0 | 8.5 |
| 207 | (1H-Benzoimidazol-5-yl)-{(4-chloro-3-fluoro-phenyl)-[1-(2-thiophen-2-yl-ethyl)-1H-tetrazol-5-yl]-methyl}-amine | 454.12 | 454.14 | 476.1 | 0 | 4 |
| 208 | 2-{5-[(1H-Benzoimidazol-5-ylamino)-(3-propoxy-phenyl)-methyl]-tetrazol-1-yl}-cyclohexanecarboxylic acid ethyl ester | 504.33 | 504.32 | 526.31 | 526.3 | 2.2 |
| 209 | 2-{5-[(1H-Benzoimidazol-5-ylamino)-(4-methoxy-phenyl)-methyl]-tetrazol-1-yl}-1-(3,4-dihydro-1H-isoquinolin-2-yl)-ethanone | 495.26 | 495.29 | 517.25 | 517.26 | 4 |
| 210 | (1H-Benzoimidazol-5-yl)-[[1-(2-benzyloxy- | 504.25 | 504.26 | 526.23 | 0 | 2.2 |

| | | | | | | |
|---|---|---|---|---|---|---|
| | phenyl)-1H-tetrazol-5-yl]-(4-methoxy-phenyl)-methyl]-amine | | | | | |
| 211 | (1H-Benzoimidazol-5-yl)-{(4-pyridin-2-yl-phenyl)-[1-(2-thiophen-2-yl-ethyl)-1H-tetrazol-5-yl]-methyl}-amine | 479.21 | 479.22 | 501.19 | 0 | 2.2 |
| 212 | {5-[(1H-Benzoimidazol-5-ylamino)-(4-pyridin-2-yl-phenyl)-methyl]-tetrazol-1-yl}-acetic acid tert-butyl ester | 483.26 | 483.27 | 505.25 | 0 | 2.2 |
| Ex. No. | Structure |
|---|---|
| 1 | 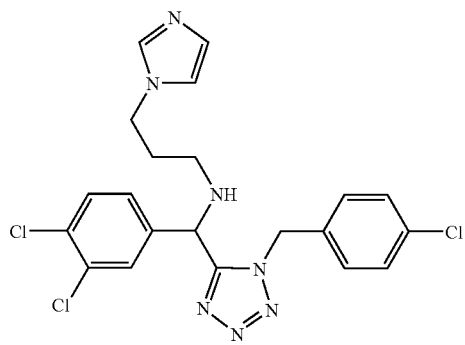 |
| 2 | 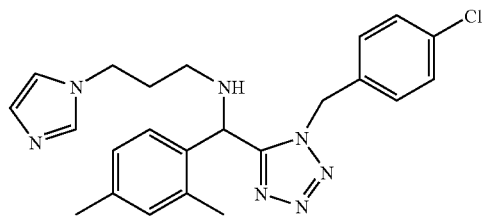 |
| 3 | 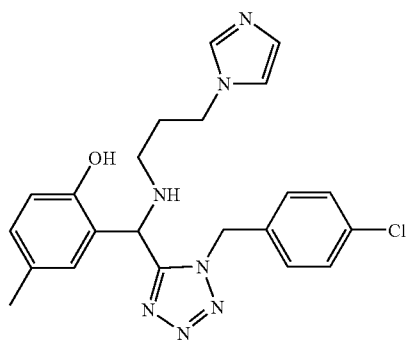 |

-continued
| | |
|---|---|
| 4 | 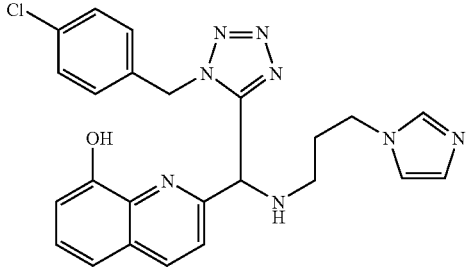 |
| 5 | 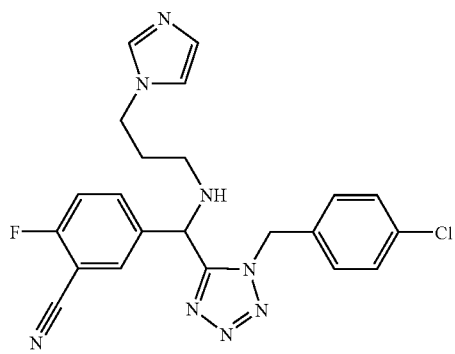 |
| 6 | 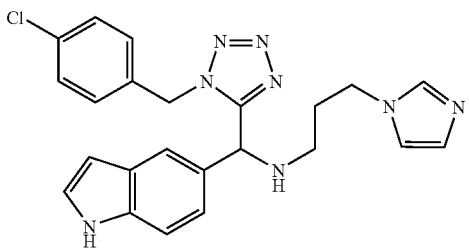 |
| 7 | 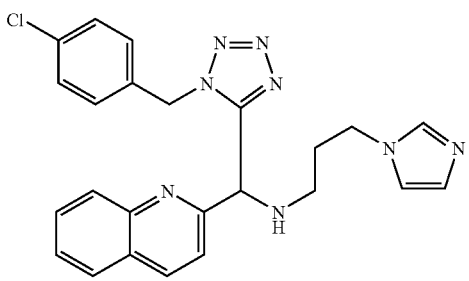 |
| 8 | 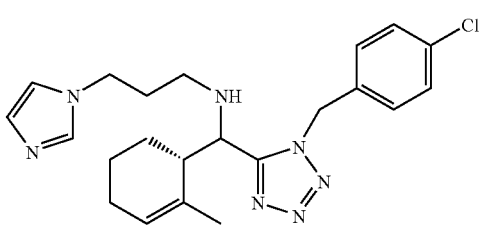 |
| 9 | 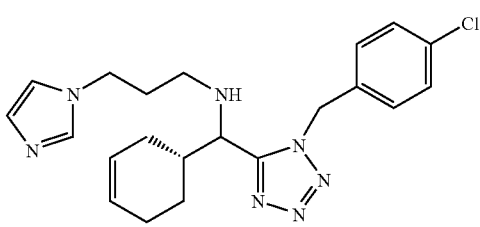 |

10 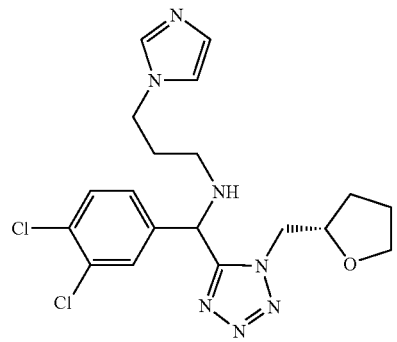
11 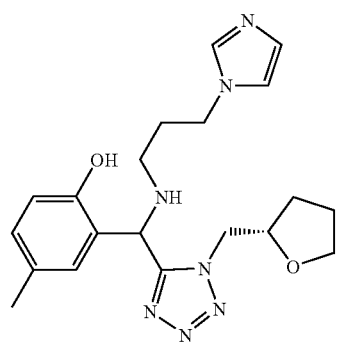
12 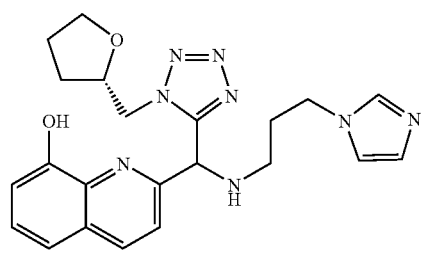
13 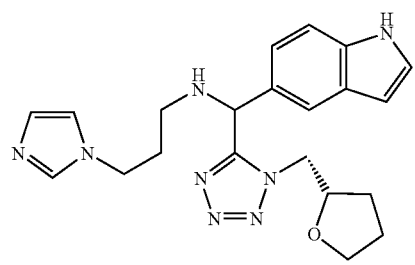
14 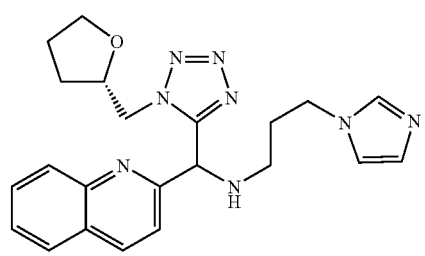

-continued
15
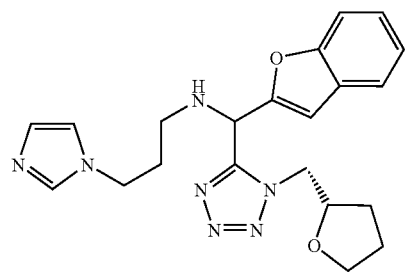
16
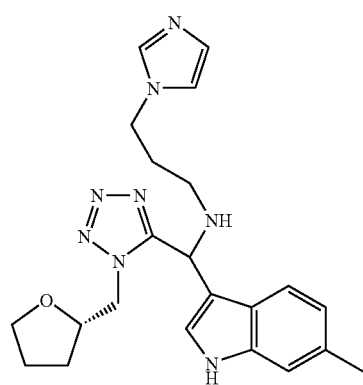
17
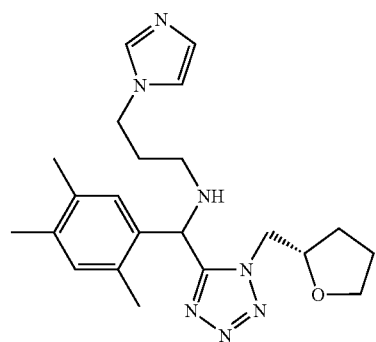
18
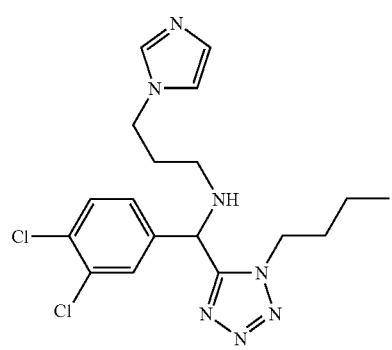

-continued
| | |
|---|---|
| 19 | 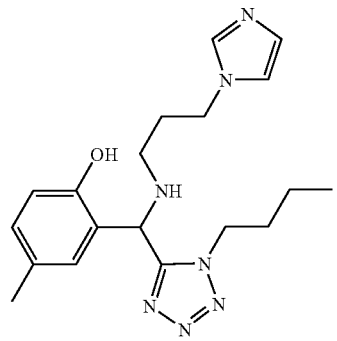 |
| 20 | 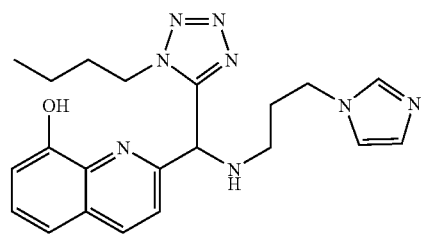 |
| 21 | 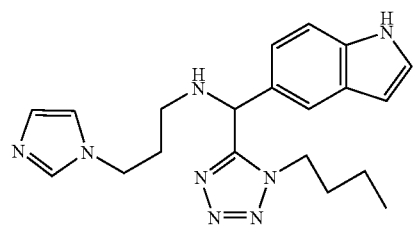 |
| 22 | 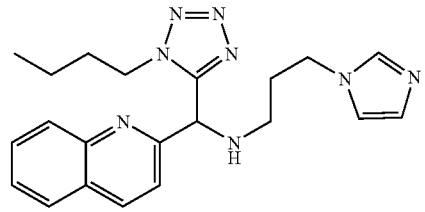 |
| 23 | 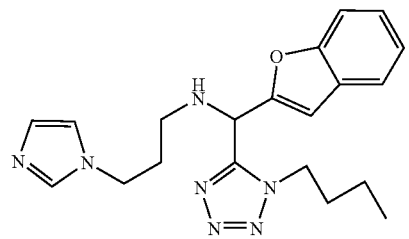 |
| 24 | 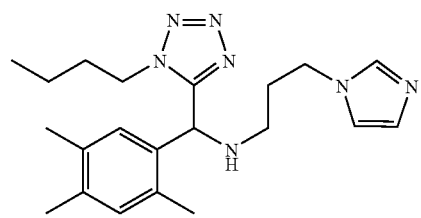 |

-continued
25
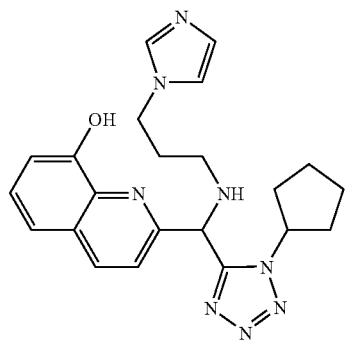
26
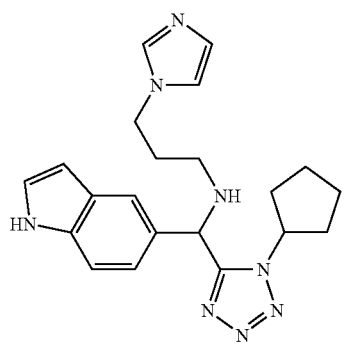
27
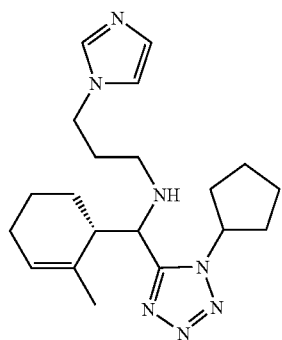
28
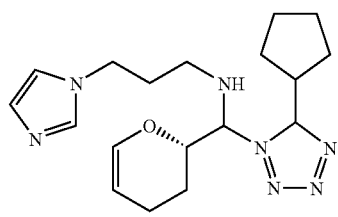
29
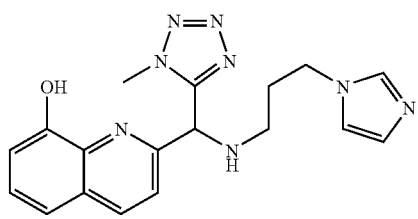

-continued
30 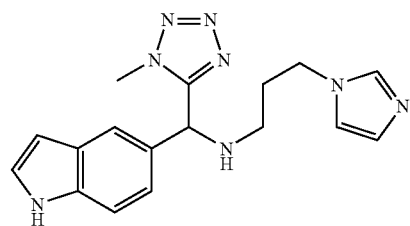
31 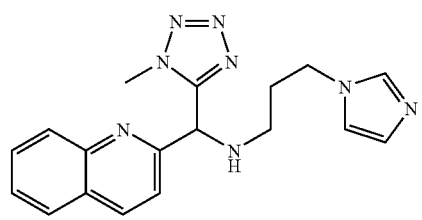
32 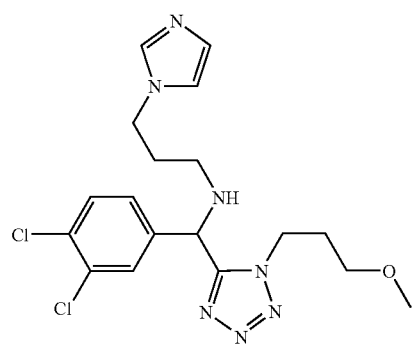
33 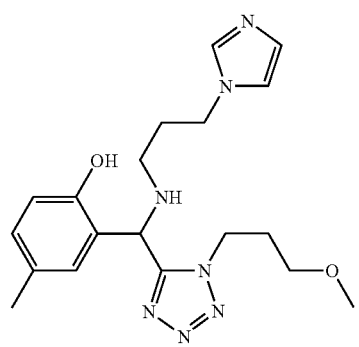
34 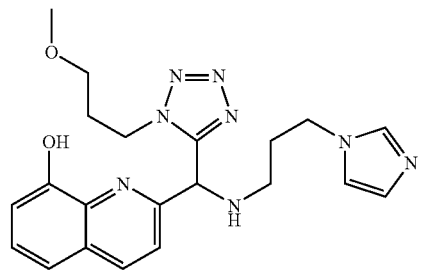

-continued
35 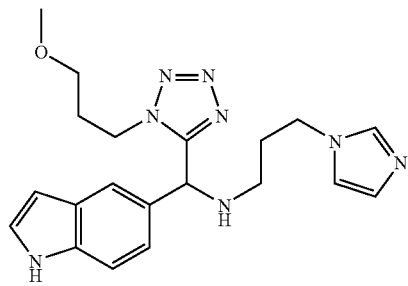
36 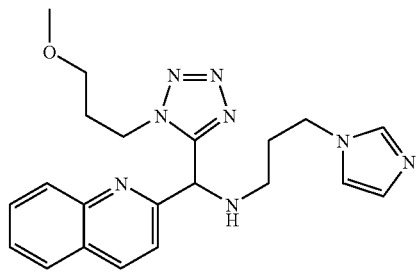
37 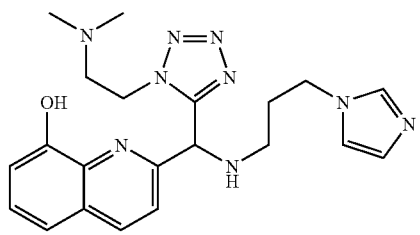
38 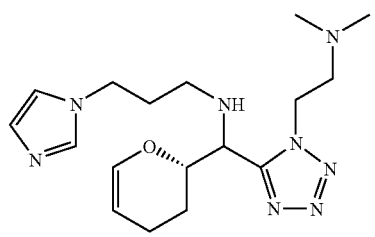
39 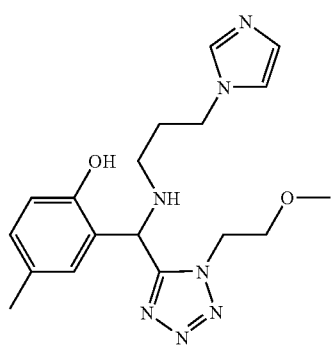
40 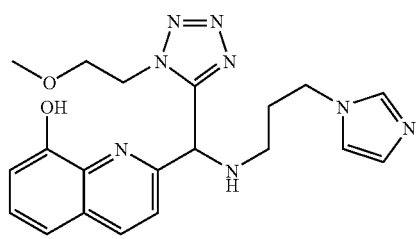

-continued
41 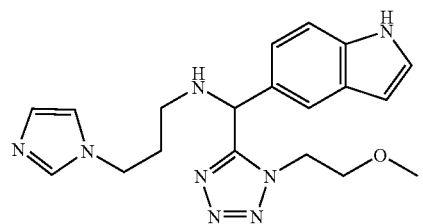
42 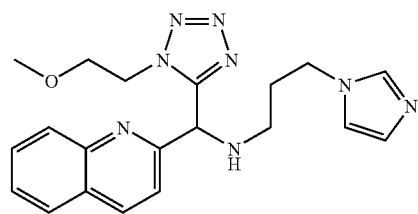
43 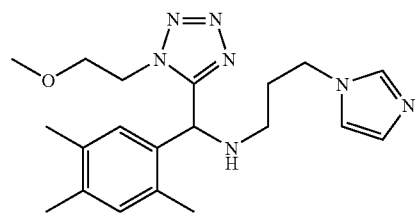
44 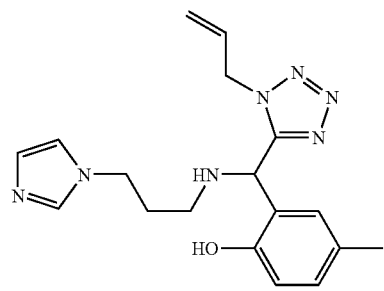
45 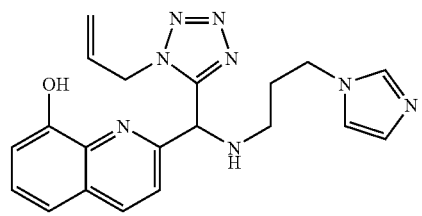
46 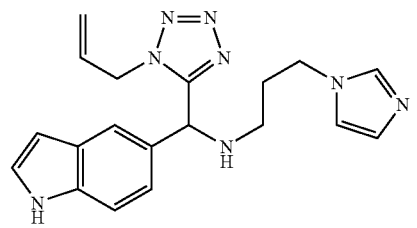

-continued
| | |
|---|---|
| 47 | 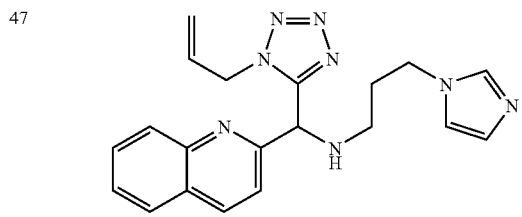 |
| 48 | 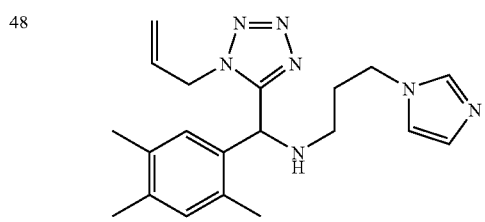 |
| 49 | 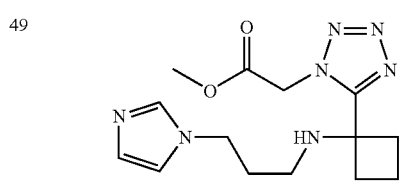 |
| 50 | 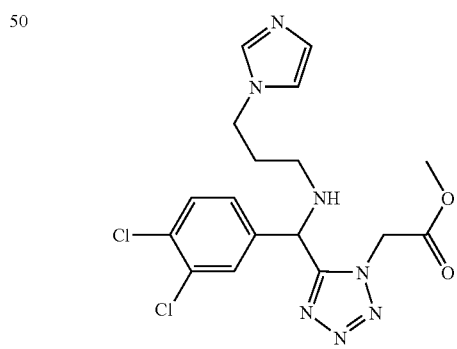 |
| 51 | 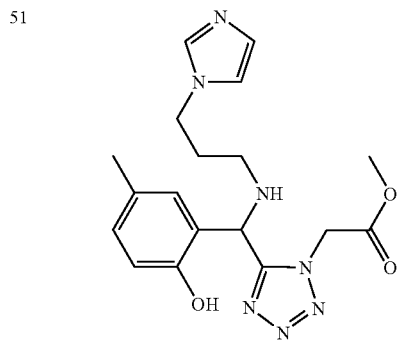 |
| 52 | 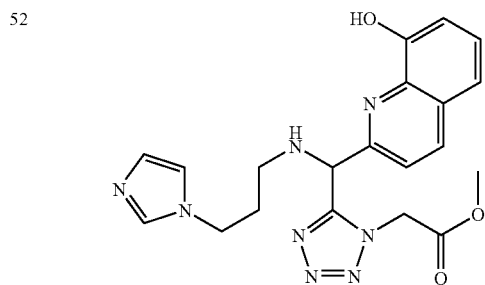 |

-continued
53
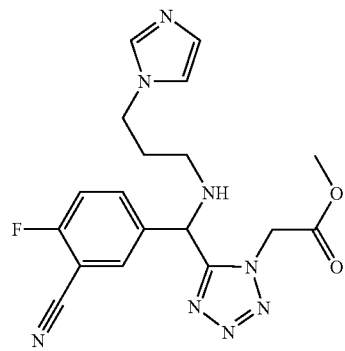
54
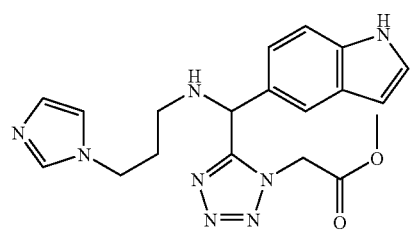
55
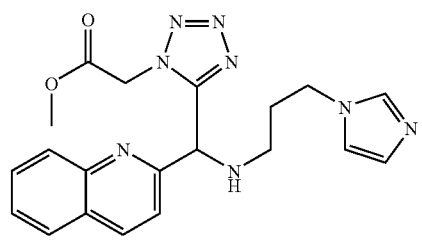
56
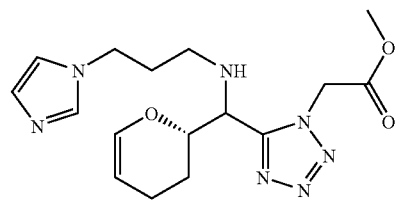
57
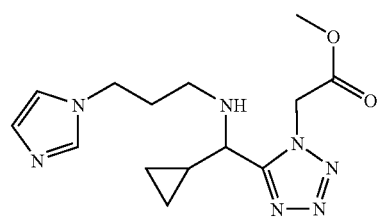
58
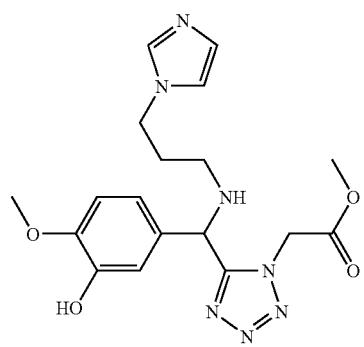

-continued
59
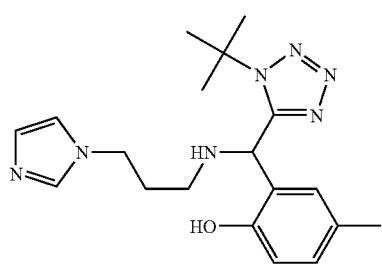
60
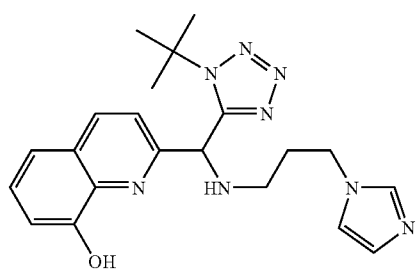
61
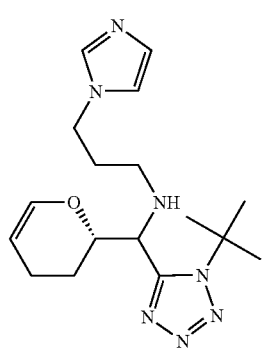
62
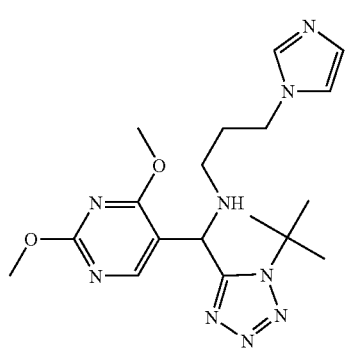
63
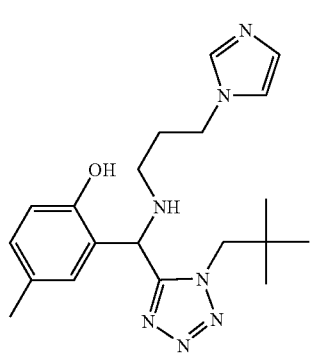

-continued
64
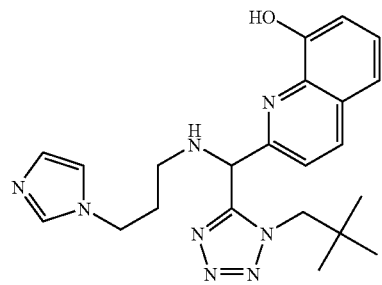
65
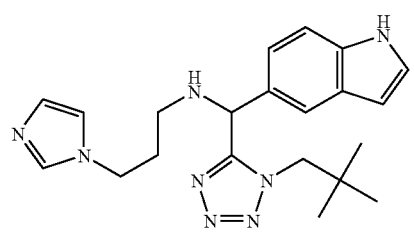
66
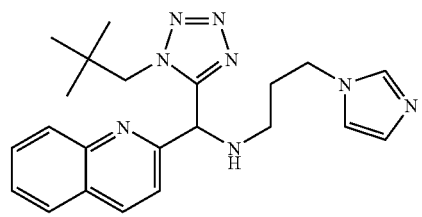
67
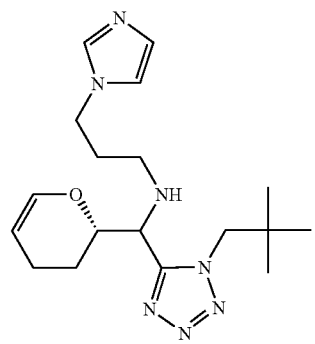
68
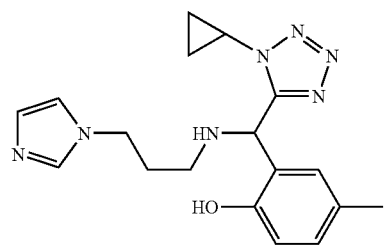

-continued
| | |
|---|---|
| 69 | 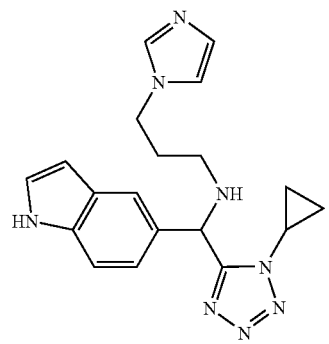 |
| 70 | 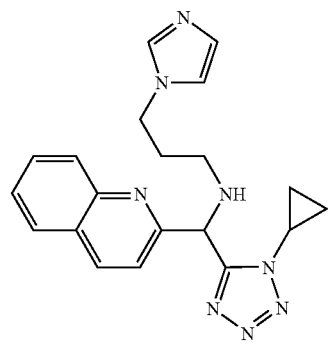 |
| 71 | 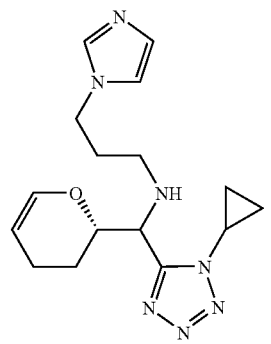 |
| 72 | 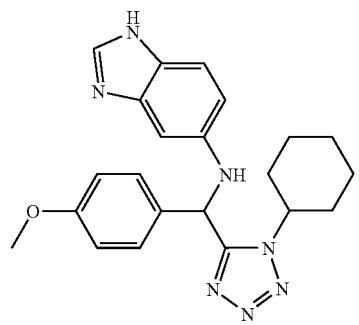 |

-continued
73
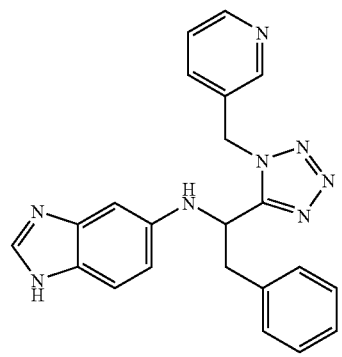
74
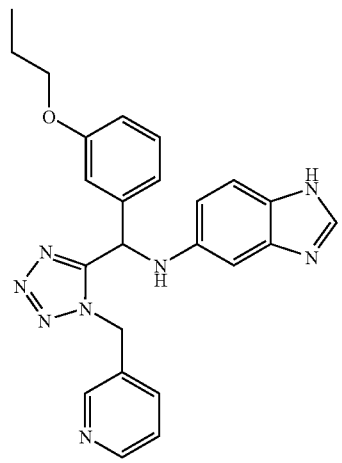
75
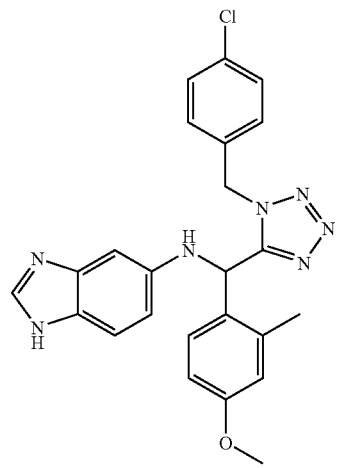

76 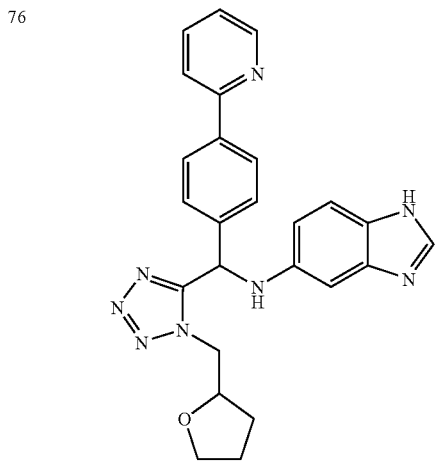
77 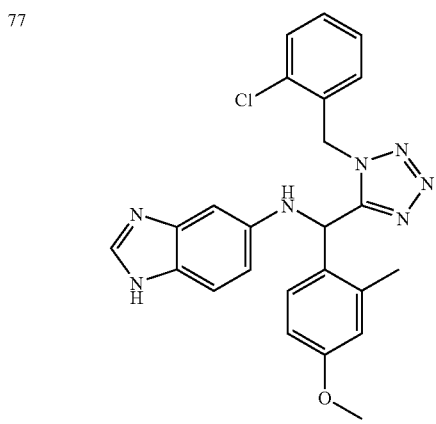
78 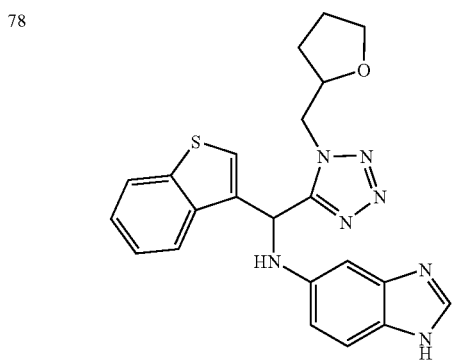
79 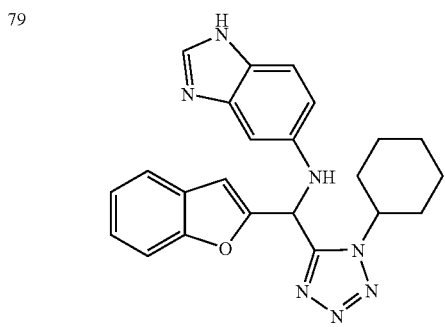

80 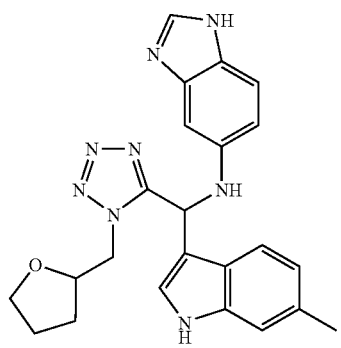
81 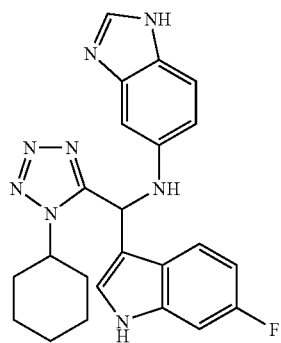
82 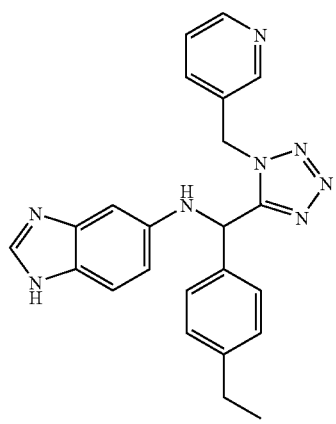
83 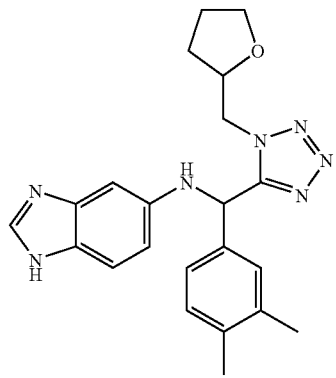

-continued
84
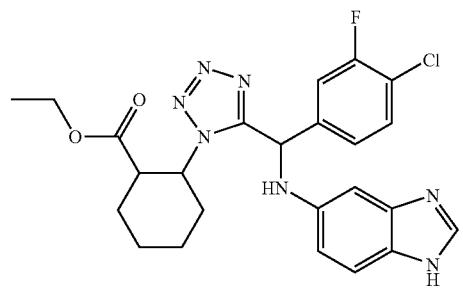
85
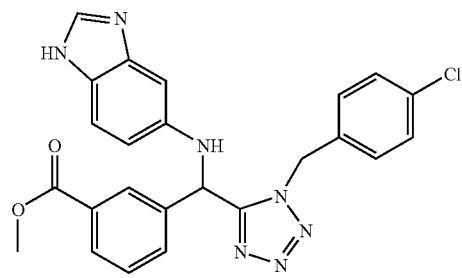
86
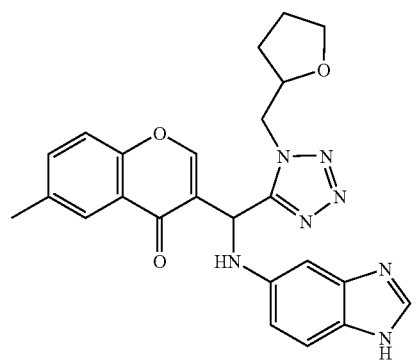
87
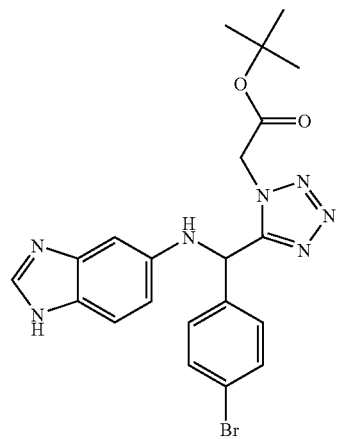

-continued
| | |
|---|---|
| 88 | 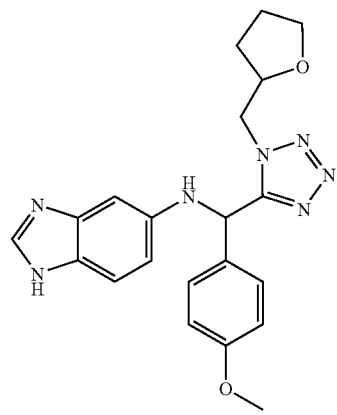 |
| 89 | 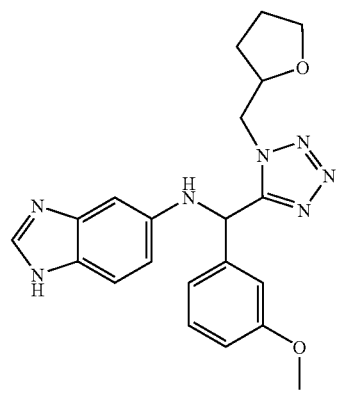 |
| 90 | 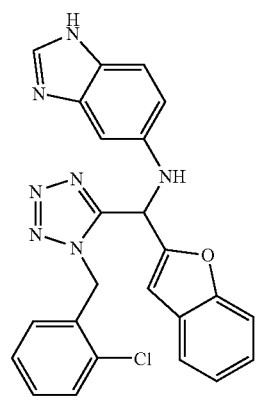 |
| 91 | 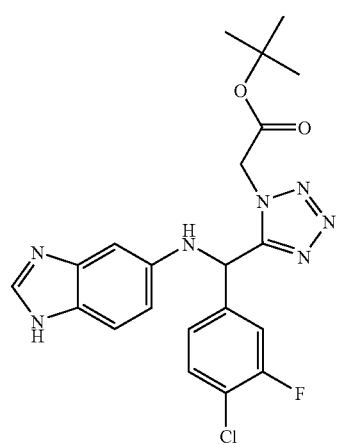 |

-continued
92
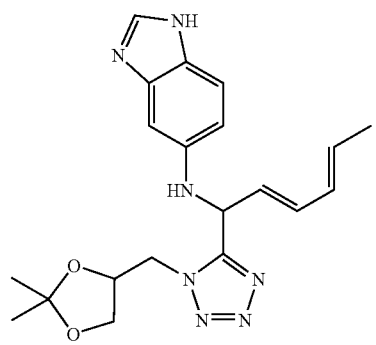
93
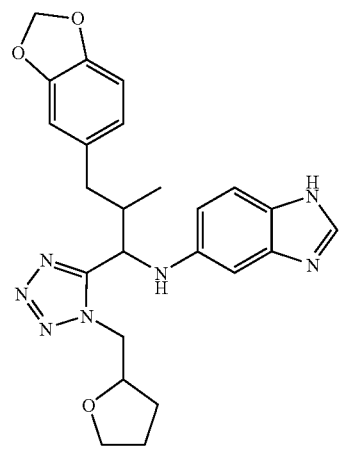
94
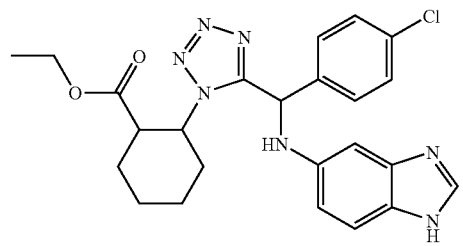
95
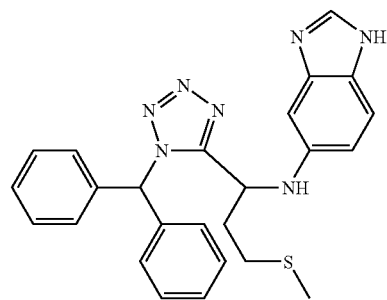

-continued
96
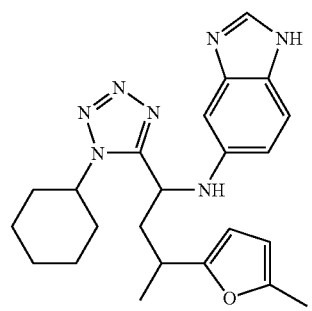
97
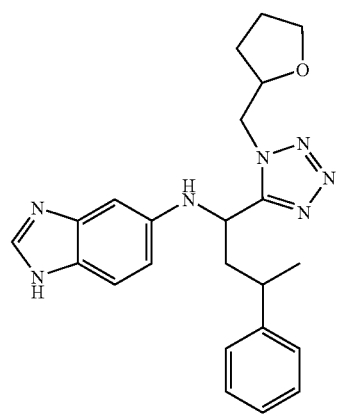
98
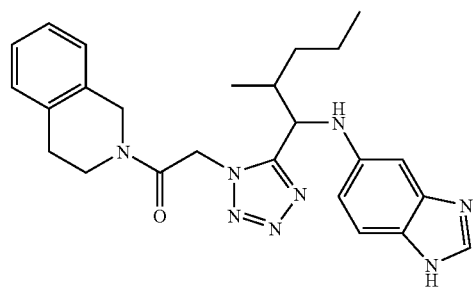
99
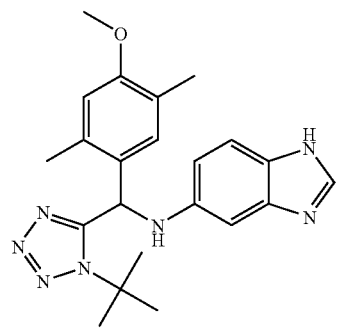

-continued
100 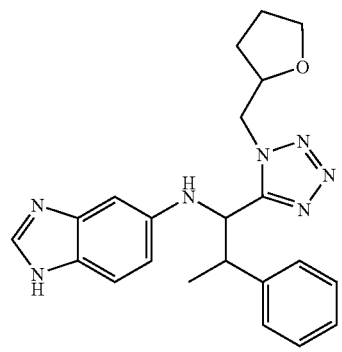
101 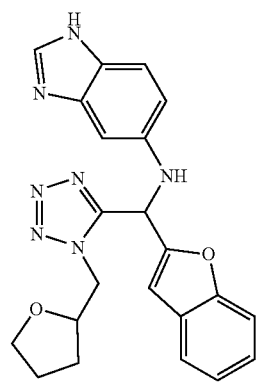
102 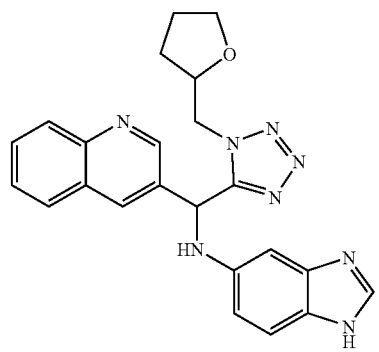
103 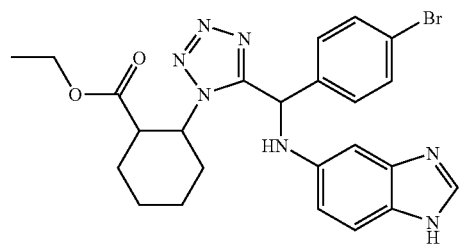
104 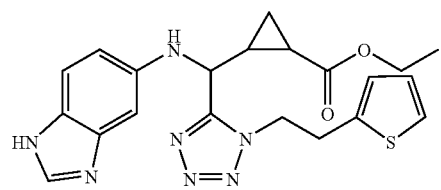

-continued
105
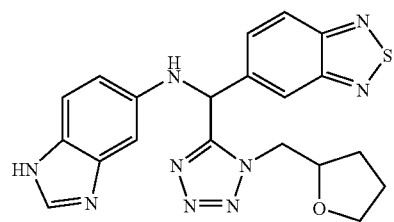
106
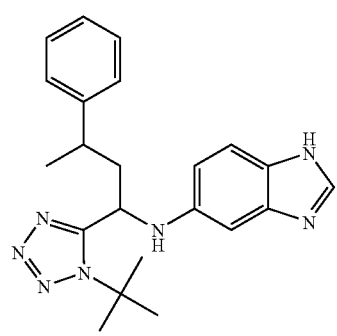
107
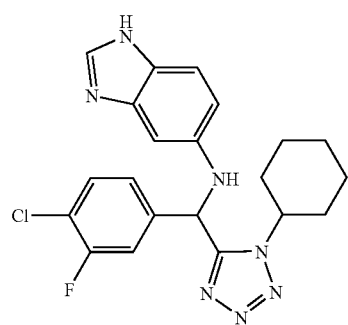
108
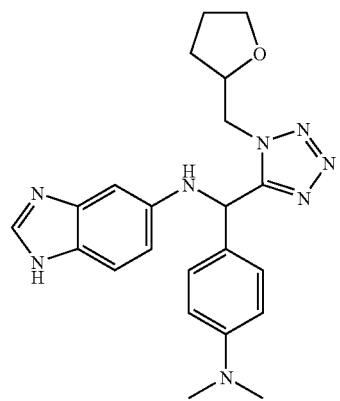

-continued
109
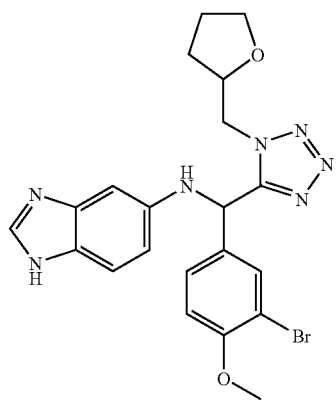
110
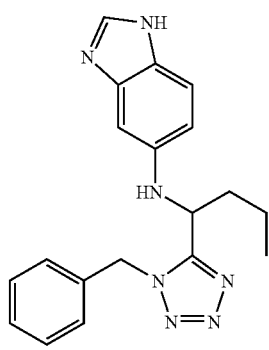
111
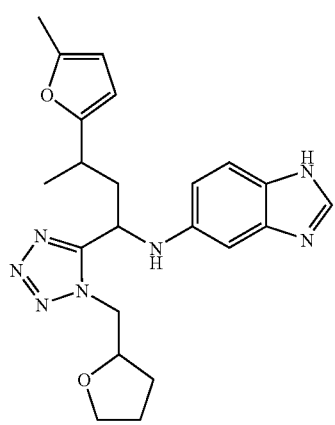
112
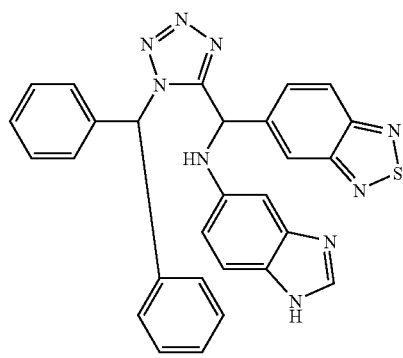

113 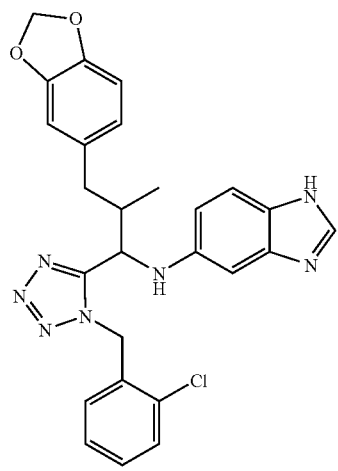
114 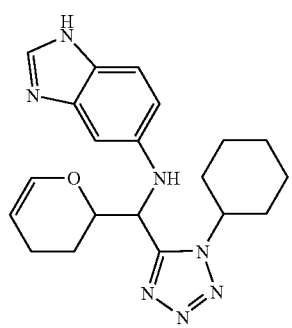
115 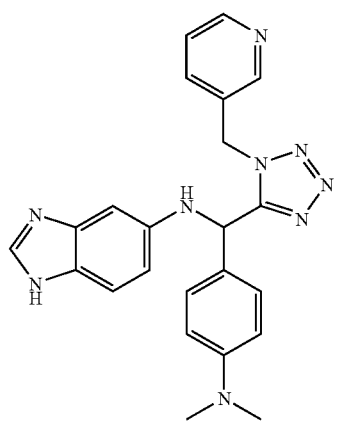
116 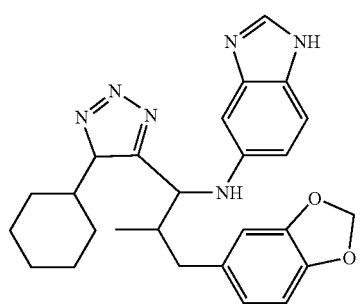

-continued
117 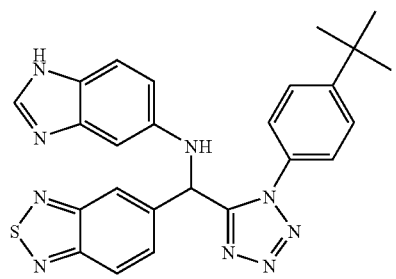
118 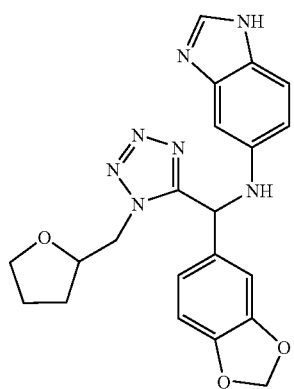
119 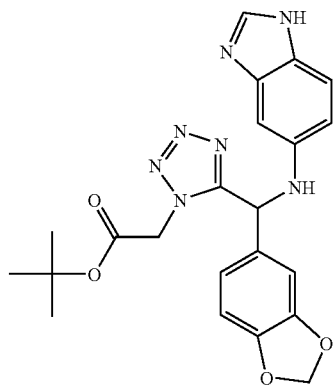
120 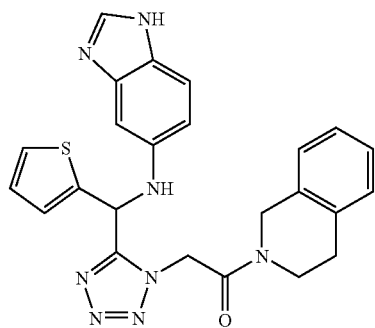

| 121 | 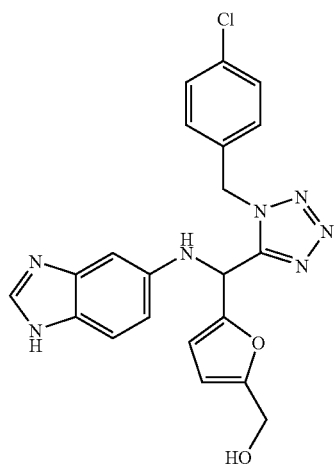 |
| 122 | 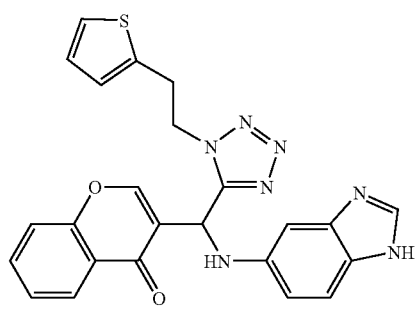 |
| 123 | 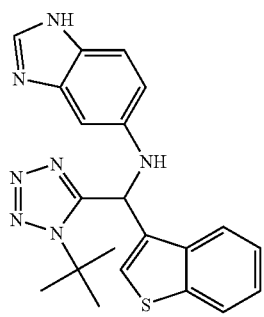 |
| 124 | 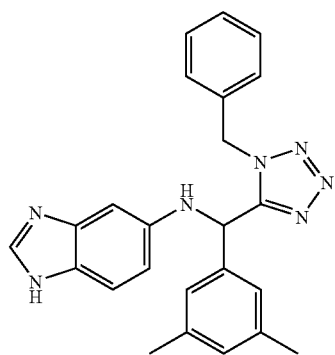 |

-continued
125
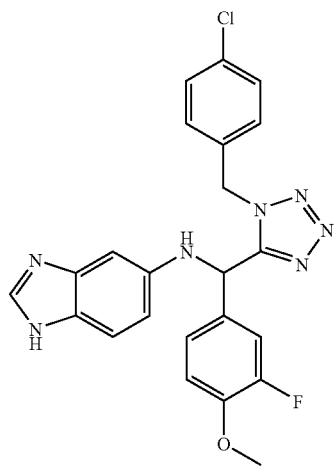
126
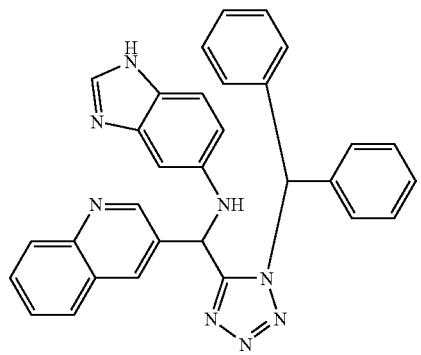
127
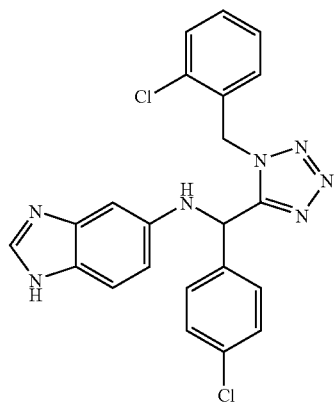
128
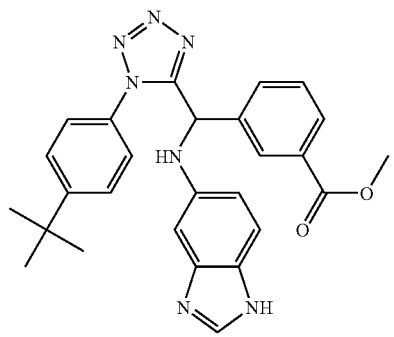

129 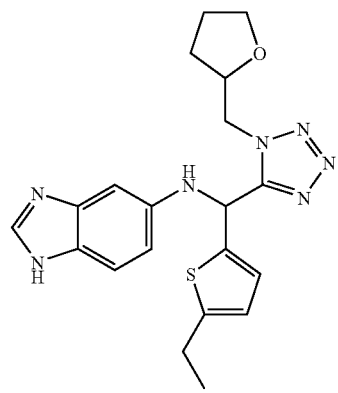
130 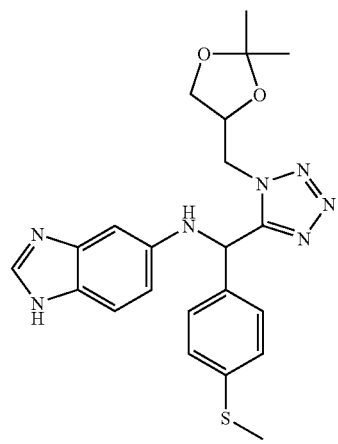
131 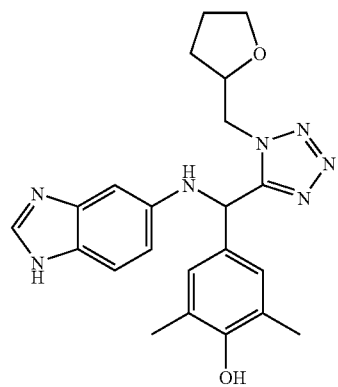
132 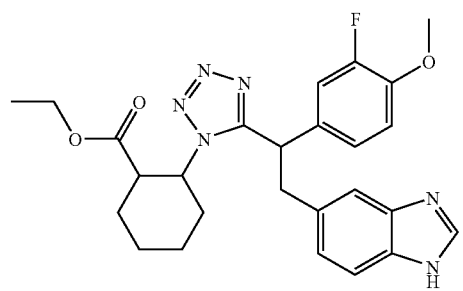

-continued
133 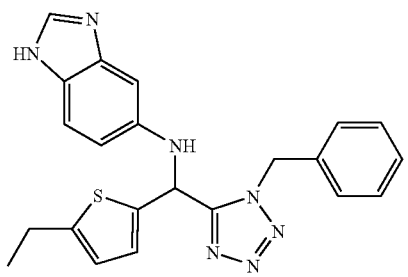
134 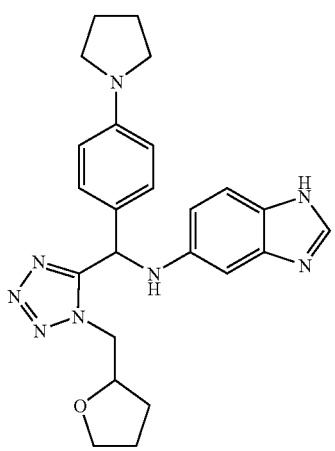
135 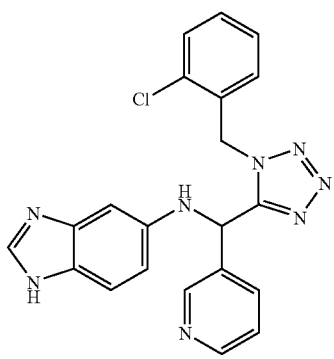
136 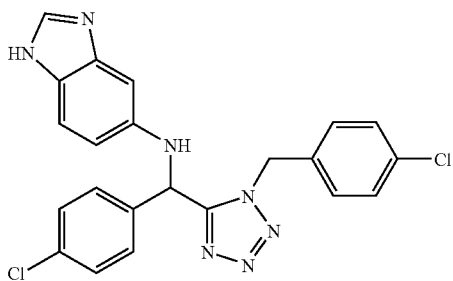

-continued
| 137 | 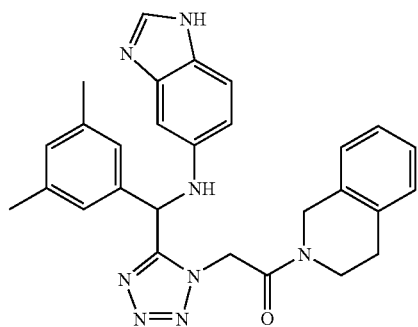 |
| --- | --- |
| 138 | 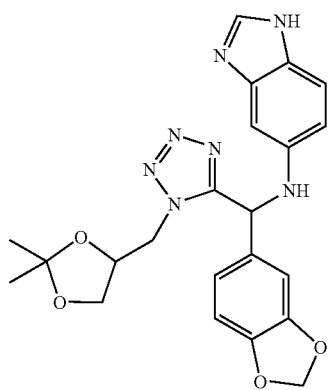 |
| 139 | 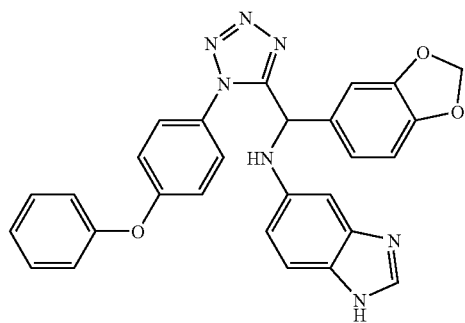 |
| 140 | 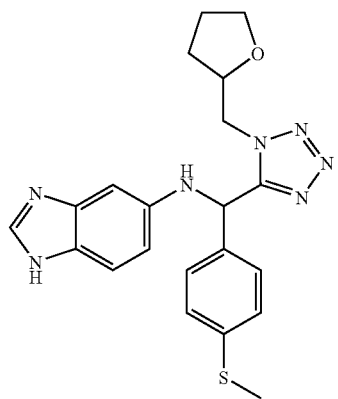 |

141 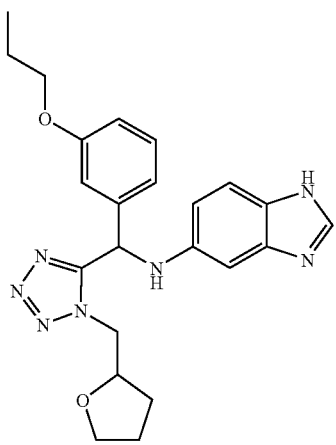
142 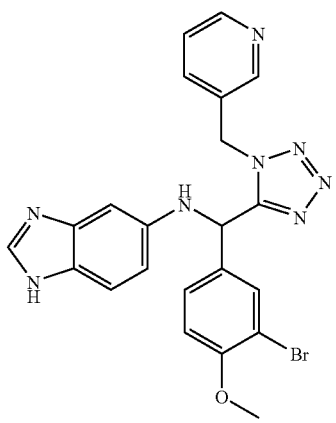
143 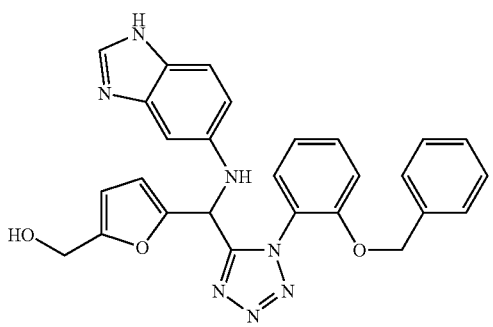
144 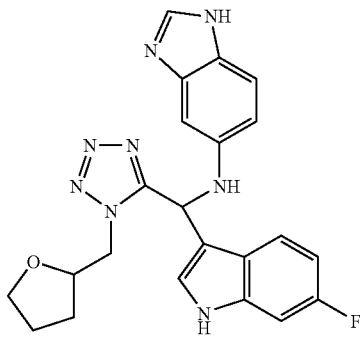

145 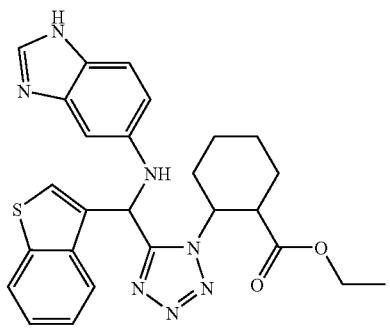
146 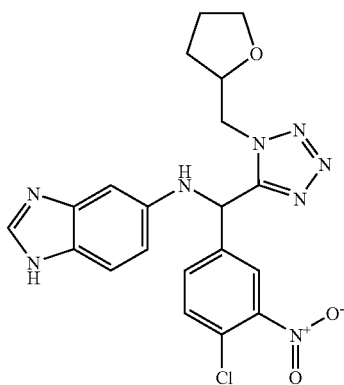
147 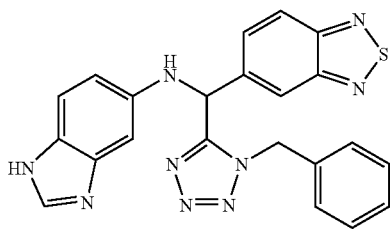
148 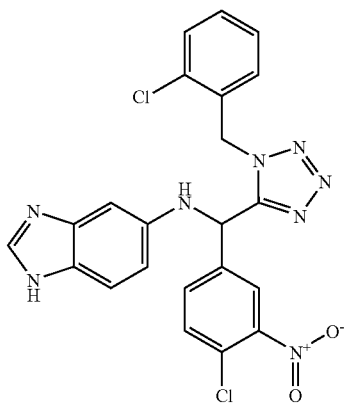

149
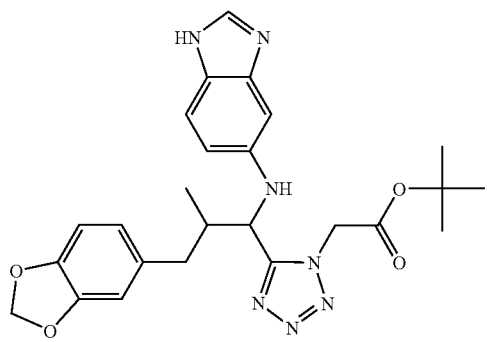
150
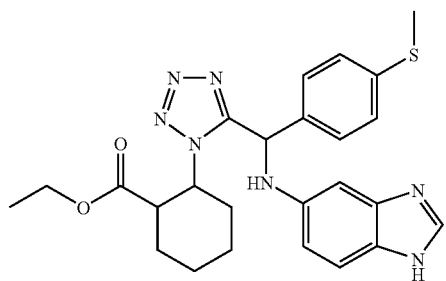
151
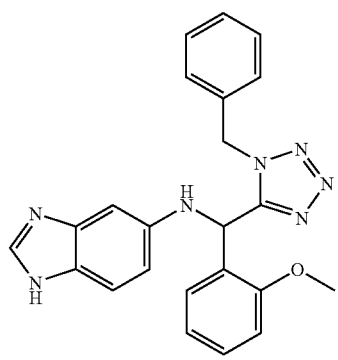
152
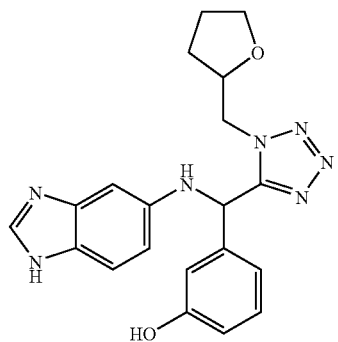

153 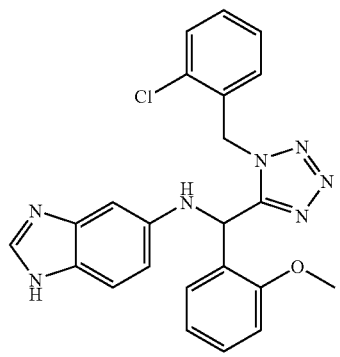
154 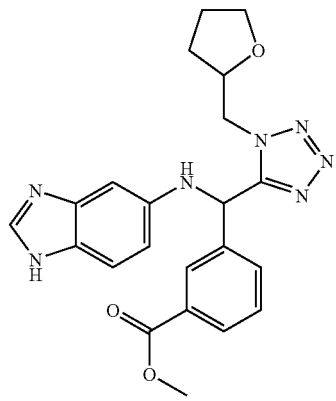
155 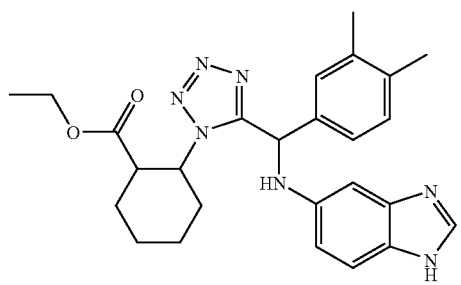
156 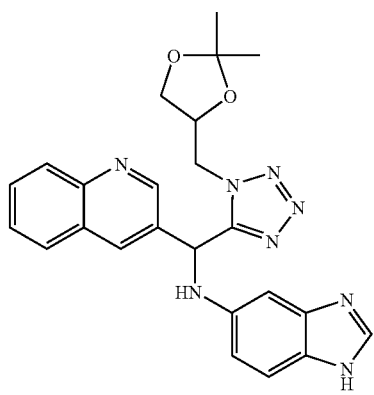

157 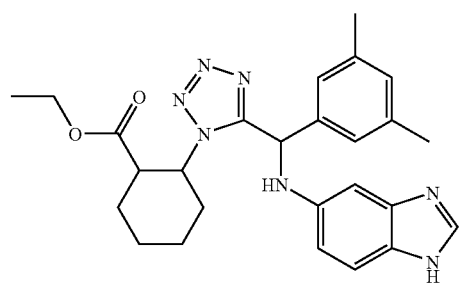
158 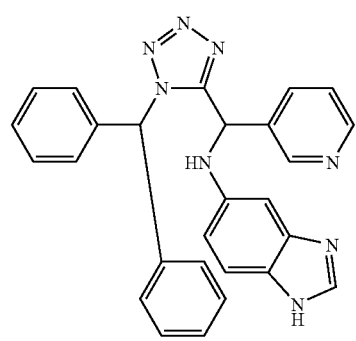
159 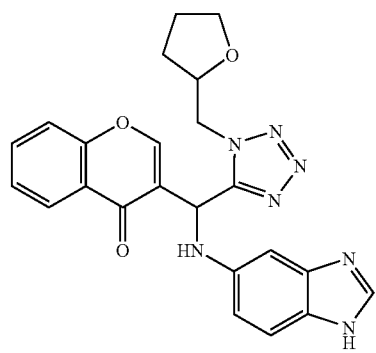
160 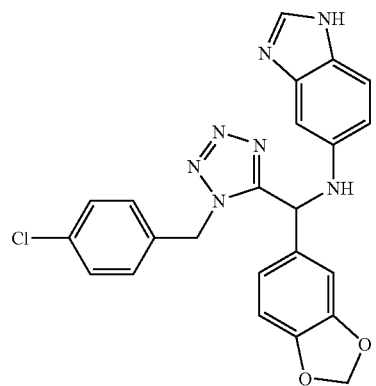

161 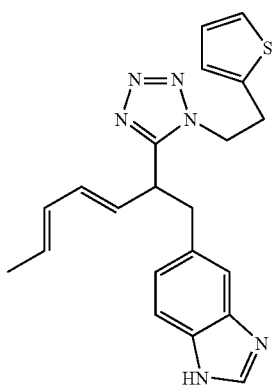
162 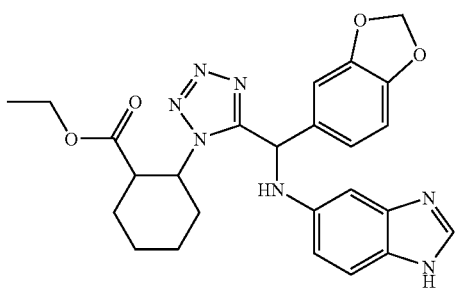
163 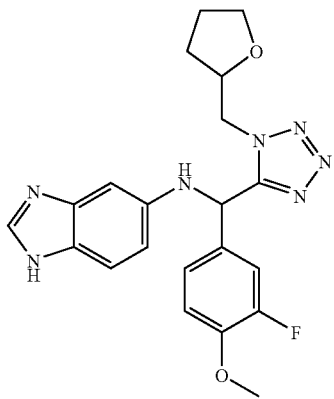
164 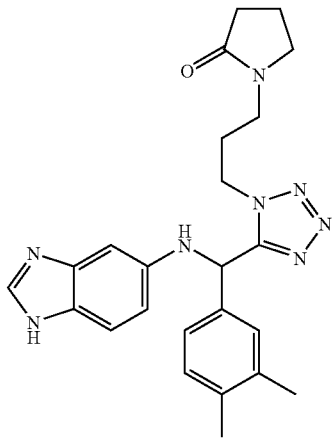

-continued
165
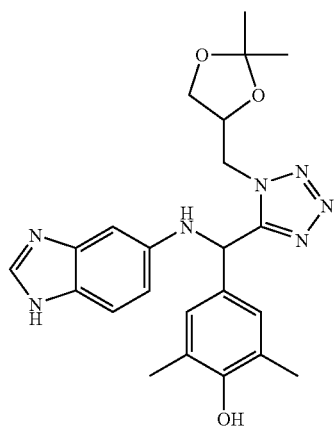
166
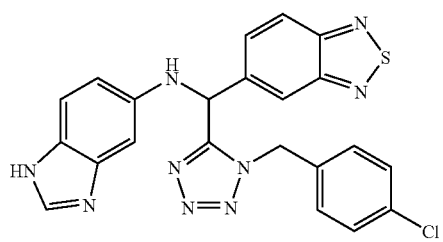
167
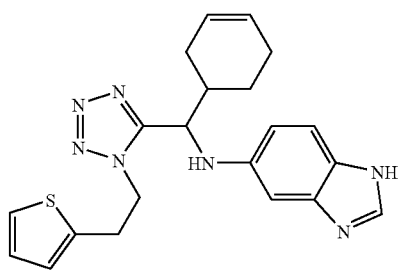
168
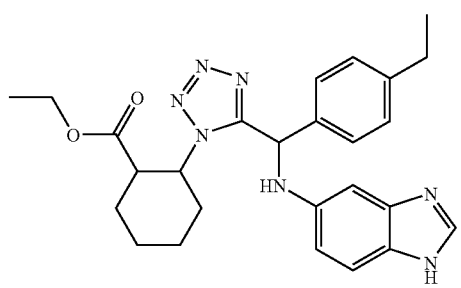
169
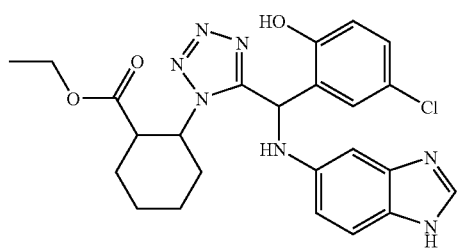

170 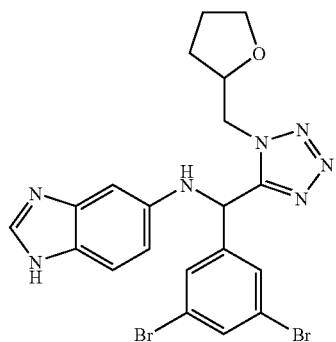
171 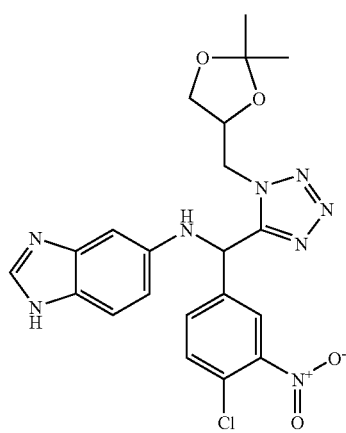
172 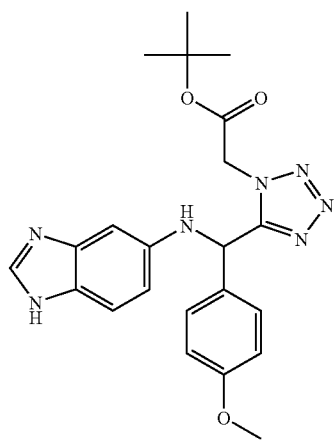
173 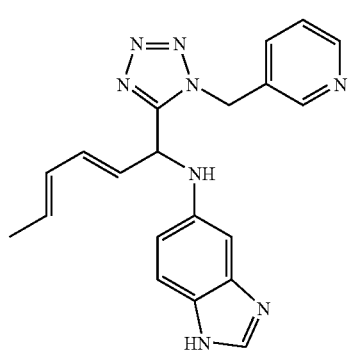

-continued
174
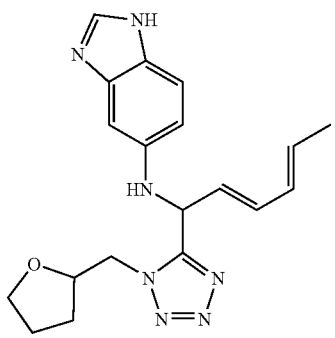
175
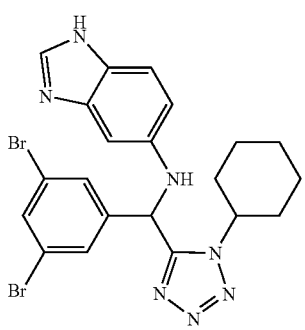
176
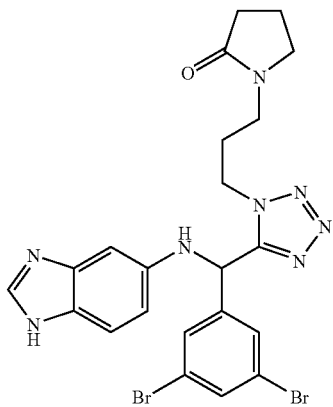
177
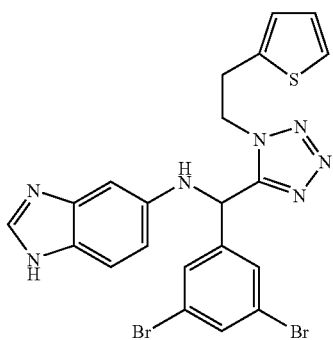

178 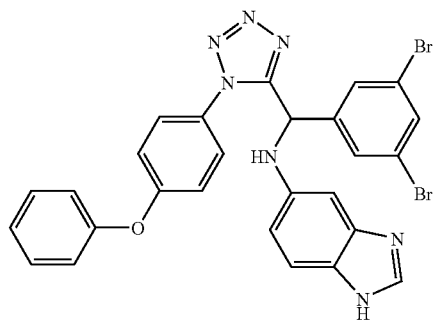
179 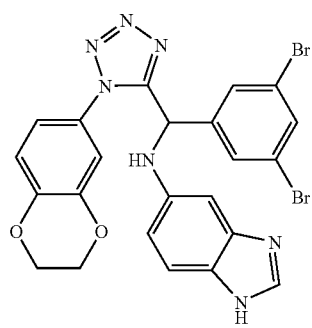
180 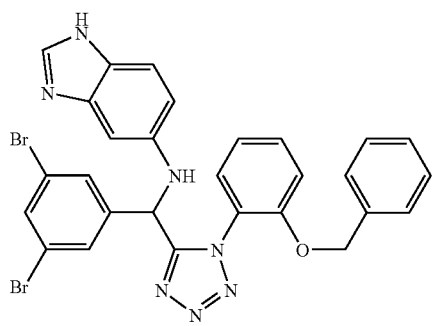
181 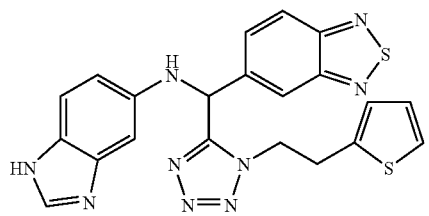
182 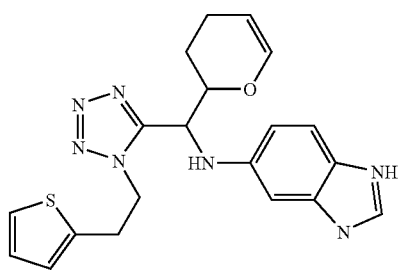

-continued
183
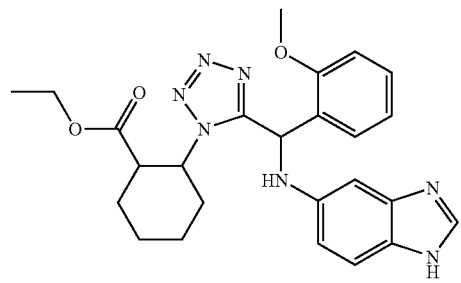
184
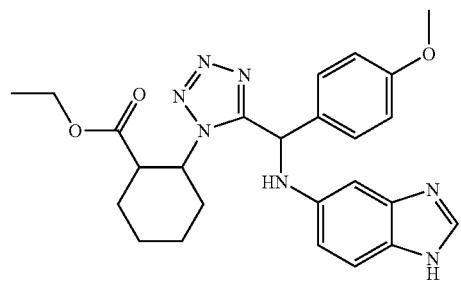
185
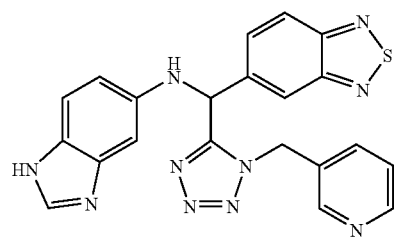
186
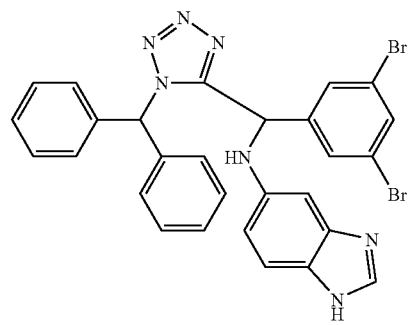
187
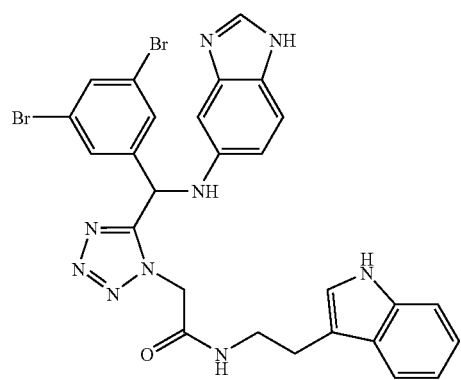

-continued
188
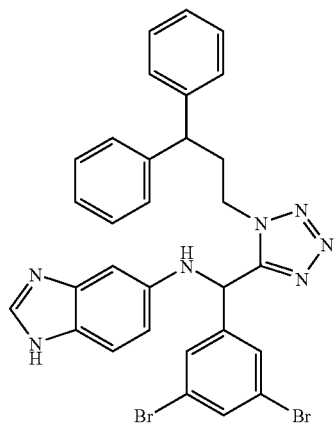
189
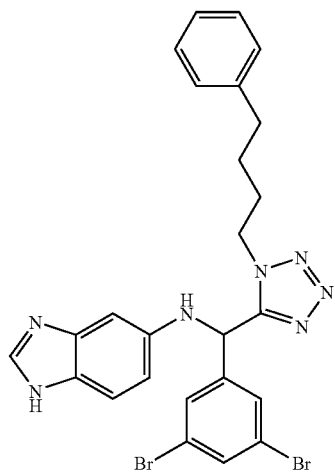
190
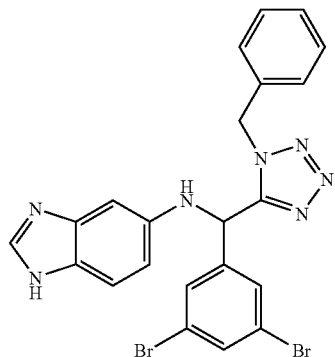
191
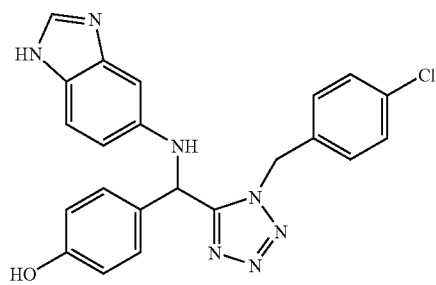

-continued
192
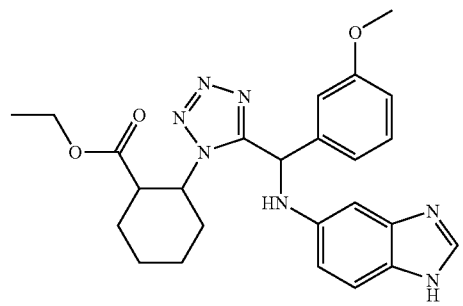
193
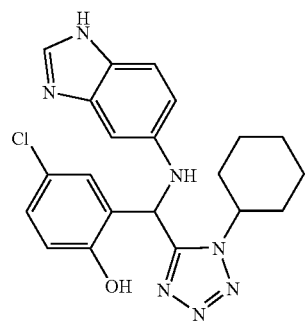
194
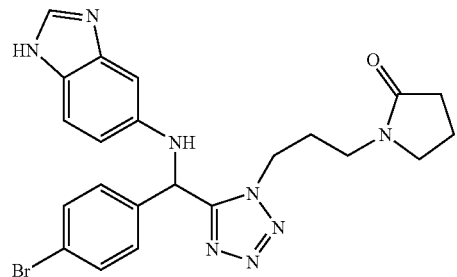
195
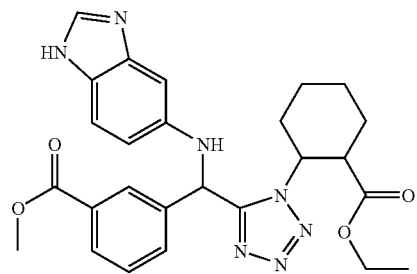
196
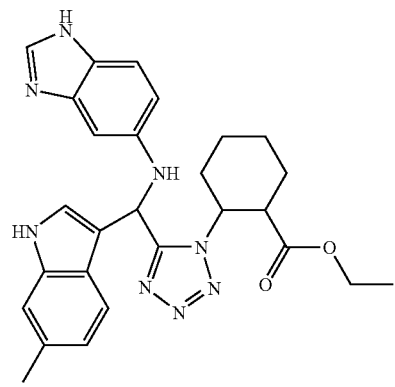

-continued
197
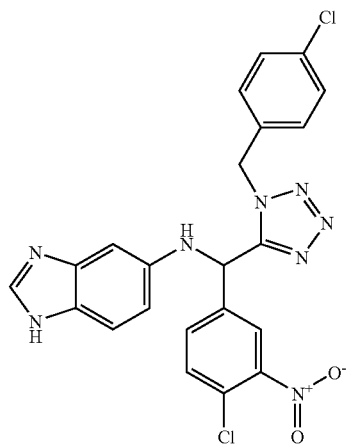
198
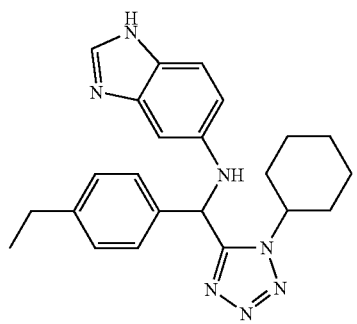
199
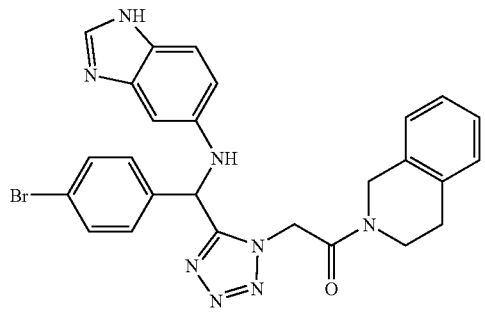
200
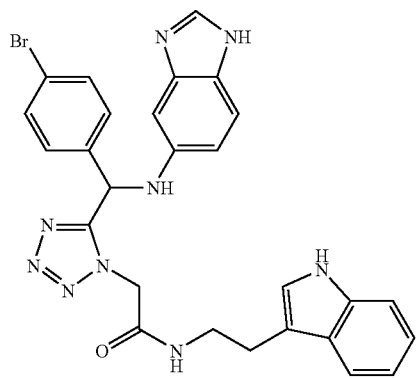

-continued
| | |
|---|---|
| 201 | 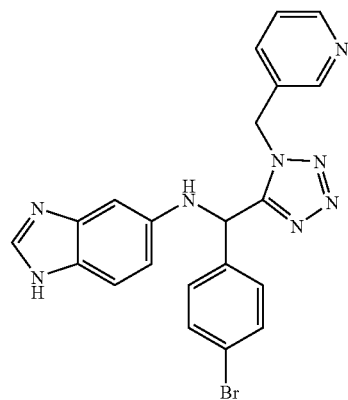 |
| 202 | 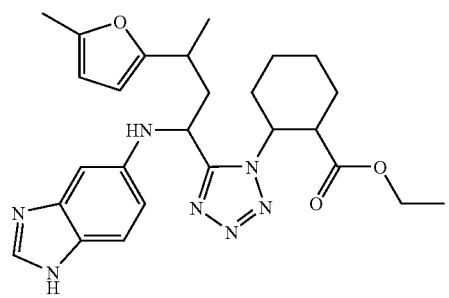 |
| 203 | 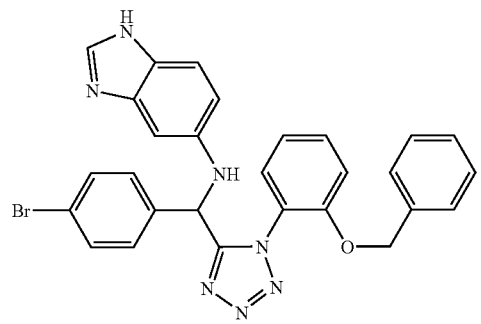 |
| 204 | 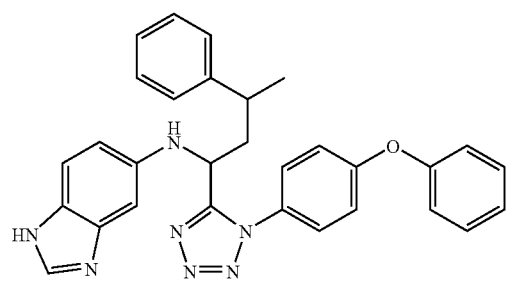 |
| 205 | 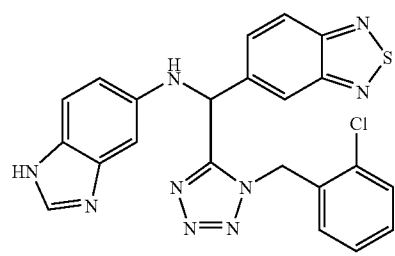 |

206 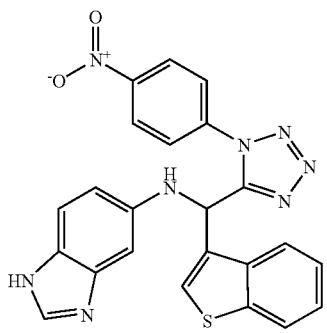
207 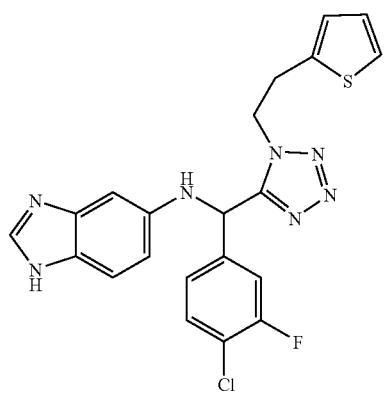
208 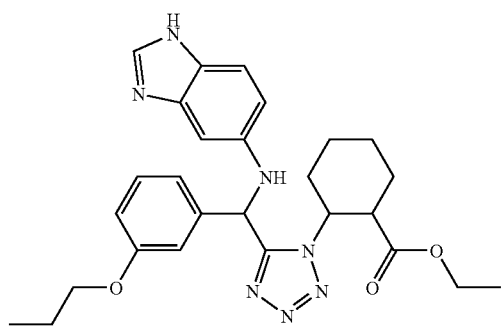
209 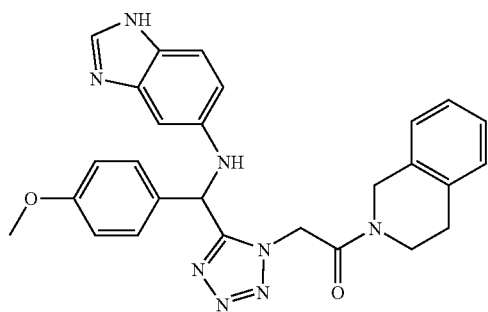

210

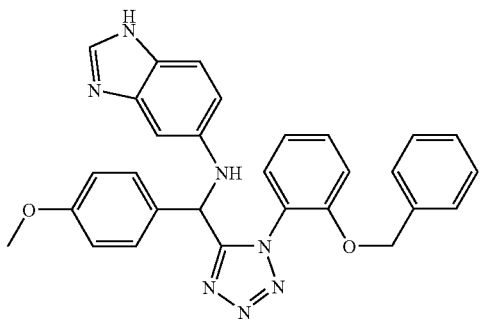

211

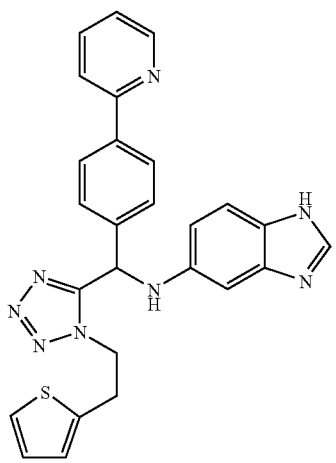

212

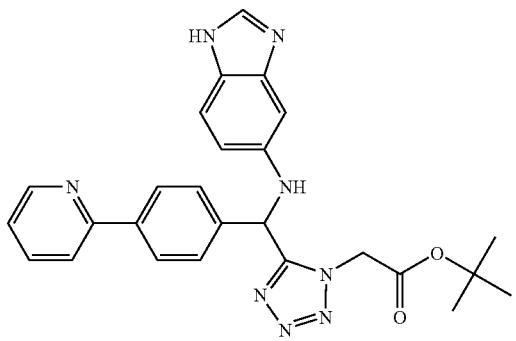

Synthesis of the Examples

Synthesis Scheme 1

The compounds were synthesized according the general synthesis scheme 1 and their identity was confirmed by mass spectrometry.

Scheme 1

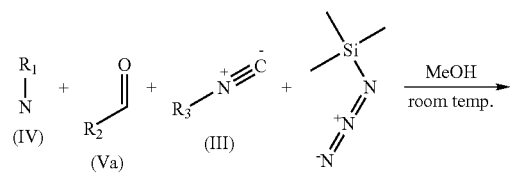

-continued

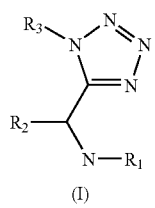

Amine (IV), 50 μl 0.2M, in methanol (dry) was dispensed on 96-well plates. Aldehyde (Va), 50 μl 0.2M in methanol (dry) was then added. The well plates were stacked for 30 minutes at room temperature. Subsequently isocyanide (III), 50 μl 0.2 M, in methanol (dry) and 50 μl 1M Trimethylsilylazide was added. The well plates were sealed and stacked for 48 hours at room temperature. After completion, the solvent was evaporated.

All compounds were immediately tested regarding their activity as hQC inhibitors. $IC_{50}$ values were found to be in the range of 0.01 to 10 uM when tested directly following synthesis (i.e. without purification).

Detailed Synthesis Description

Certain compounds of the invention were prepared by preparative synthesis following essentially the route used for the parallel synthesis.

General Workup

The appropriate amine (IV) (1 mmol) and aldehyde (Va) (1 mmol) were combined in methanol (2 ml, dry). After 2 hours Trimethylsilylazide (5 mmol) and the appropriate isocyanide (III) (1 mmol) was added. The reaction was stirred at room temperature for 48 h. After evaporation of the solvent the residue was purified with chromatographic methods.

The purity of the compounds was determined by HPLC-MS. The $IC_{50}$ value against hQC was measured using the fluorescent assay.

Purification and Characterisation

The resulting crude reaction products were purified in an automatic process using a semi-preparative HPLC-MS with mass-triggered sampling of the desired peak:

Purification via semi-preparative HPLC-MS

Instrumentation:
2× Varian PrepStar SD-1
1× Dionex P580 Pump 1 Channel(MakeUP I)
1× Dionex AXP-MS (MakeUP II)
1× Dionex MSQ
1× Dionex UVD 340V—Prep Flow Cell
Gilson 215 Liquid Handler Column:
SunFire Prep C18 OBD 5 um 19×50 mm Method:

| Column Flow: | 30 ml/min |
| Solvent A: | methanol, 0.3% acetic acid |
| Solvent B: | water, 0.3% acetic acid |

Time table for gradient:

| Time (min) | Solvent A | Solvent B |
| --- | --- | --- |
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

Detection:
UV 254 nm, Mass Spectrometer Detector (API-ES, positive)

Compound Verification

The compound verification via analytical HPLC-MS was done after purification using the following instrumentation, column and method:

Analytical Method for Compound Purity

Instrumentation:
Agilent MSD 1100

Column:
YMC ODS-A 2.1×50, 3 um

Method:

| Column Flow: | 0.600 ml/min |
| Solvent A: | acetonitrile, 0.5% acetic acid |
| Solvent B: | 90% water, 10% acetonitrile, 0.5% acetic acid |

Time table for gradient:

| Time (min) | Solvent A | Solvent B |
| --- | --- | --- |
| 0.0 | 0.00 | 100.00 |
| 2.5 | 90.00 | 10.00 |
| 4.0 | 90.00 | 10.00 |
| 4.5 | 0.00 | 100.00 |
| 6.0 | 0.00 | 100.00 |

Detection:
UV 254 nm, Mass Spectrometer Detector (API-ES, positive)

Compound 3: 2-[[1-(4-Chloro-benzyl)-1H-tetrazol-5-yl]-(3-imidazol-1-yl-propylamino)-methyl]-4-methyl-phenol

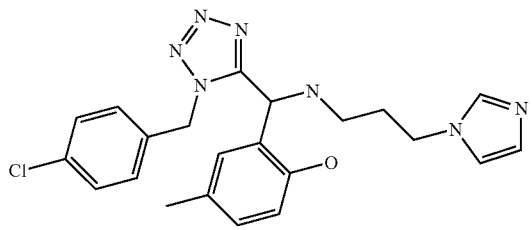

3-Imidazol-1-yl-propylamine (1 mmol) and 2-Hydroxy-5-methyl-benzaldehyde (1 mmol) were combined in methanol (2 ml, dry). After 2 hours Trimethylsilylazide (5 mmol) and 1-Chloro-4-isocyanomethyl-benzene (1 mmol) was added. The reaction was stirred at room temperature for 48 h. After evaporation of the solvent the residue was purified with chromatographic methods.

| molecular weight (g/mol): | 437.94 |
| RT-UV254nm (min): | 2.84 |
| $IC_{50}$ hQC (nM): | 584 |

181

Compound 6: [[1-(4-Chloro-benzyl)-1H-tetrazol-5-yl]-(1H-indol-5-yl)-methyl]-(3-imidazol-1-yl-propyl)-amine

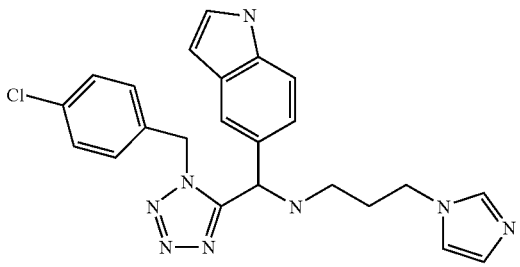

3-Imidazol-1-yl-propylamine (1 mmol) and 1H-Indole-5-carbaldehyde (1 mmol) were combined in methanol (2 ml, dry). After 2 hours Trimethylsilylazide (5 mmol) and 1-Chloro-4-isocyanomethyl-benzene (1 mmol) was added. The reaction was stirred at room temperature for 48 h. After evaporation of the solvent the residue was purified with chromatographic methods.

| | |
|---|---|
| molecular weight (g/mol): | 446.95 |
| RT-UV254nm (min): | 2.70 |
| IC$_{50}$ hQC (nM): | 450 |

Compound 28: [(1-Cyclopentyl-1H-tetrazol-5-yl)-(3,4-dihydro-2H-pyran-2-yl)-methyl]-(3-imidazol-1-yl-propyl)-amine

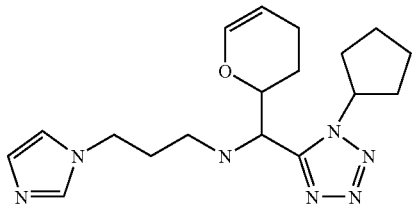

3-Imidazol-1-yl-propylamine (1 mmol) and 3,4-Dihydro-2H-pyran-2-carbaldehyde (1 mmol) were combined in methanol (2 ml, dry). After 2 hours Trimethylsilylazide (5 mmol) and Isocyano-cyclopentan (1 mmol) was added. The reaction was stirred at room temperature for 48 h. After evaporation of the solvent the residue was purified with chromatographic methods.

| | |
|---|---|
| molecular weight (g/mol): | 357.46 |
| RT-UV254nm (min): | 2.66 |
| IC$_{50}$ hQC (nM): | 3468 |

182

Compound 38: {(3,4-Dihydro-2H-pyran-2-yl)-[1-(2-dimethylamino-ethyl)-1H-tetrazol-5-yl]-methyl}-(3-imidazol-1-yl-propyl)-amine

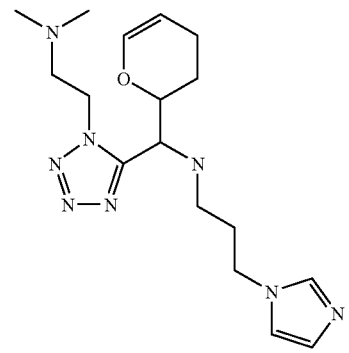

3-Imidazol-1-yl-propylamine (1 mmol) and 3,4-Dihydro-2H-pyran-2-carbaldehyde (1 mmol) were combined in methanol (2 ml, dry). After 2 hours Trimethylsilylazide (5 mmol) and (2-Isocyano-ethyl)-dimethyl-amine (1 mmol) was added. The reaction was stirred at room temperature for 48 h. After evaporation of the solvent the residue was purified with chromatographic methods.

| | |
|---|---|
| molecular weight (g/mol): | 360.47 |
| RT-UV254nm (min): | 0.33 |
| IC$_{50}$ hQC (nM): | 2880 |

Compound 63: 2-[[1-(2,2-Dimethyl-propyl)-1H-tetrazol-5-yl]-(3-imidazol-1-yl-propylamino)-methyl]-4-methyl-phenol

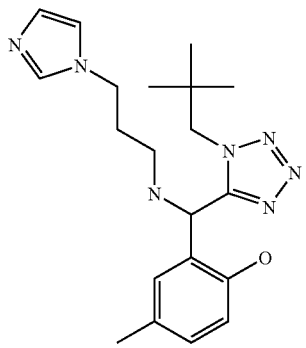

3-Imidazol-1-yl-propylamine (1 mmol) and 2-Hydroxy-5-methyl-benzaldehyde (1 mmol) were combined in methanol (2 ml, dry). After 2 hours Trimethylsilylazide (5 mmol) and 1-Isocyano-2,2-dimethyl-propane (1 mmol) was added. The reaction was stirred at room temperature for 48 h. After evaporation of the solvent the residue was purified with chromatographic methods.

| | |
|---|---|
| molecular weight (g/mol): | 383.50 |
| RT-UV254nm (min): | 2.63 |
| IC$_{50}$ hQC (nM): | 2368 |

Compound 64: 2-[[1-(2,2-Dimethyl-propyl)-1H-tetrazol-5-yl]-(3-imidazol-1-yl-propylamino)-methyl]-quinolin-8-ol

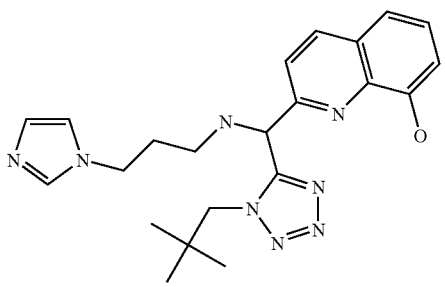

3-Imidazol-1-yl-propylamine (1 mmol) and 8-Hydroxy-quinoline-2-carbaldehyde (1 mmol) were combined in methanol (2 ml, dry). After 2 hours Trimethylsilylazide (5 mmol) and 1-Isocyano-2,2-dimethyl-propane (1 mmol) was added. The reaction was stirred at room temperature for 48 h. After evaporation of the solvent the residue was purified with chromatographic methods.

| | |
|---|---|
| molecular weight (g/mol): | 420.52 |
| RT-UV254nm (min): | 2.93 |
| $IC_{50}$ hQC (nM): | 1030 |

Compound 68: 2-[(1-Cyclopropyl-1H-tetrazol-5-yl)-(3-imidazol-1-yl-propylamino)-methyl]-4-methylphenol

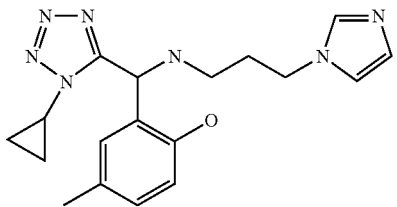

3-Imidazol-1-yl-propylamine (1 mmol) and 2-Hydroxy-5-methyl-benzaldehyde (1 mmol) were combined in methanol (2 ml, dry). After 2 hours Trimethylsilylazide (5 mmol) and Isocyano-cyclopropane (mmol) was added. The reaction was stirred at room temperature for 48 h. After evaporation of the solvent the residue was purified with chromatographic methods.

| | |
|---|---|
| molecular weight (g/mol): | 353.43 |
| RT-UV254nm (min): | 1.10 |
| $IC_{50}$ hQC (nM): | 668 |

EXAMPLES OF THE INVENTION

Example 1

Assays for Glutaminyl Cyclase Activity

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Horsholm, Denmark) in 0.2 M Tris/HCl, pH 8.0 containing 20 mM EDTA and an appropriately diluted aliquot of QC in a final volume of 250 μl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 μmol pGlu-βNA from H-Gln-βNA per minute under the described conditions.

In a second fluorometric assay, QC was activity determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 μl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 μl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 2

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 µl) were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of formula (I)).

The first QC inhibitors were disclosed in WO 2004/098591 and WO 2005/075436. There are no other potent QC inhibitors known in the art. The same holds true for combinations and compositions for the treatment of neuronal diseases comprising QC inhibitors. Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

What is claimed is:

1. A compound of formula (I)

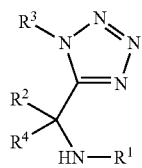

(I)

wherein
- R¹ represents heteroaryl, -carbocyclyl-heteroaryl, -alkenylheteroaryl or -alkylheteroaryl;
- R² represents alkyl, which may optionally be substituted by one or more groups selected from amino, halogen, hydroxyl, -alkoxy, -thioalkyl, —C(O)O-alkyl and —C(O)OH; carbocyclyl, which may optionally be substituted by one or more groups selected from alkyl, haloalkyl, amino, halogen, hydroxyl, alkoxy-, -thioalkyl, —C(O)O-alkyl and —C(O)OH; alkenyl; alkynyl; -alkyl-aryl; -alkyl-heteroaryl; -alkyl-heterocyclyl; -alkyl-carbocyclyl; -aryl-heteroaryl; -heteroaryl-aryl; -heteroaryl-heteroaryl; -aryl-aryl; -aryl; heteroaryl; heterocyclyl; or R² together with R⁴ may form a carbocyclyl group optionally substituted by one or more alkyl groups;
- R³ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)₂, -alkyl(heteroaryl)₂, -alkyl(aryl)(heteroaryl), -alkyl-heteroaryl; -alkyl-heterocyclyl which heterocyclyl group may optionally be substituted by one or more groups selected from alkyl, hydroxyl and oxo; -alkyl-carbocyclyl; -aryl-heteroaryl; -heteroaryl-aryl; -aryl-aryl; -aryl-O-aryl; -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl;
- R⁴ represents H or alkyl;

or a pharmaceutically acceptable salt thereof, including all tautomers and stereoisomers thereof.

2. A compound according to claim 1 wherein the following compounds are excluded from the scope of formula (I)

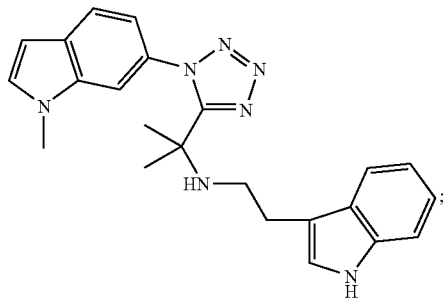

-continued

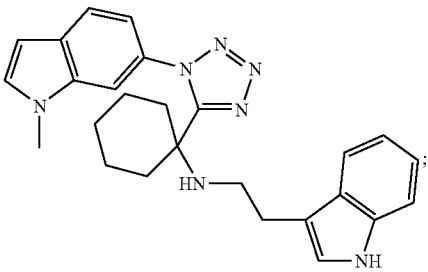

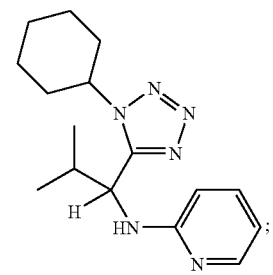

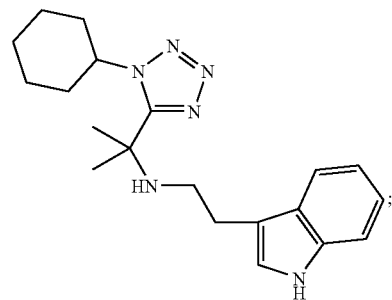

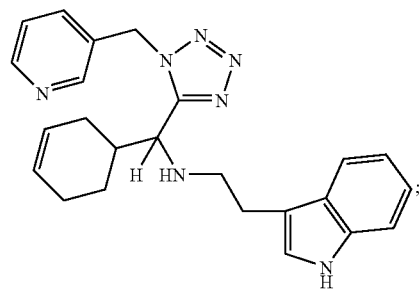

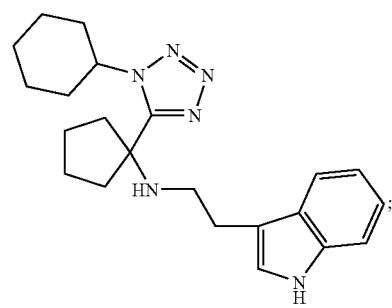

-continued

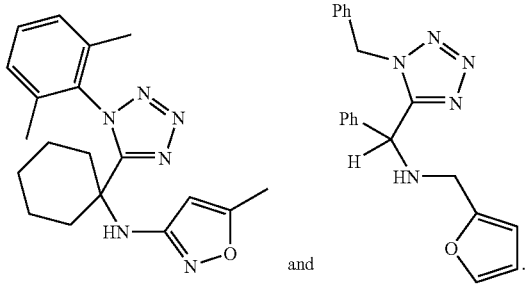

and

3. A compound according to claim 1, wherein R¹ represents -alkylheteroaryl.

4. A compound according to claim 3, wherein heteroaryl is 5 or 6 membered monocyclic heteroaryl.

5. A compound according to claim 4, wherein R¹ represents 3-imidazol-1-yl-propyl.

6. A compound according to claim 1 or claim 2, wherein R¹ represents -heteroaryl.

7. A compound according to claim 6, wherein R¹ represents 1H-benzoimidazol-5-yl.

8. A compound according to claim 1, wherein R² represents alkyl, which may optionally be substituted by one or more groups selected from -thioalkyl and —C(O)O-alkyl; carbocyclyl, which may optionally be substituted by one or more groups selected from -alkyl, -thioalkyl and —C(O)O-alkyl; alkenyl; -alkyl-aryl; -alkyl-heteroaryl; -aryl heteroaryl; -aryl; heteroaryl; heterocyclyl; or R² together with R⁴ represents carbocyclyl.

9. A compound according to claim 8, wherein R² represents aryl.

10. A compound according to claim 8, wherein R² represents heteroaryl.

11. A compound according to claim 8, wherein R² together with R⁴ represents cycloalkyl.

12. A compound according to claim 1, wherein R⁴ represents H.

13. A compound according to claim 1, wherein R³ represents alkyl, which may optionally be substituted by one or more groups selected from amino, halogen, hydroxyl, alkoxy-, -thioalkyl, —C(O)OH and —C(O)O-alkyl; carbocyclyl, which may optionally be substituted by one or more groups selected from alkyl, amino, halogen, haloalkyl, hydroxyl, -alkoxy, -thioalkyl, —C(O)OH and —C(O)O-alkyl; alkenyl; -alkyl-aryl; -alkyl(aryl)₂, -alkyl(heteroaryl)₂, -alkyl(aryl)(heteroaryl), -alkyl-heteroaryl; -alkyl-heterocyclyl which heterocyclyl group may optionally be substituted by one or more groups selected from alkyl, hydroxyl and oxo; -alkyl-carbocyclyl; -aryl-heteroaryl; -heteroaryl-aryl; -arylaryl; -heteroaryl-heteroaryl; -aryl; heteroaryl; heterocyclyl; -aryl-alkyl-aryl; -aryl-O-alkyl-aryl; -alkyl-C(O)—NH-alkyl-aryl; -alkyl-C(O)—NH-alkyl-heteroaryl; -alkyl-C(O)—NH-alkyl-heterocyclyl; -alkyl-C(O)—(N-piperidinyl) or -alkyl-C(O)—(N-pyrrolidinyl) in which piperidinyl or pyrrolidinyl may optionally be fused to optionally substituted phenyl.

14. A compound according to claim 13, wherein R³ represents unsubstituted alkyl.

15. A compound according to claim 13, wherein R³ represents alkyl substituted by —C(O)Oalkyl.

16. A compound according to claim 13, wherein R³ represents -alkyl-aryl.

17. A compound according to claim 13, wherein R³ represents -alkyl-heteroaryl.

18. A compound selected from the group consisting of examples 1-212 below and the pharmaceutically acceptable salts and solvates of them:

Example 1 [[1-(4-Chloro-benzyl)-1H-tetrazol-5-yl]-(3,4-dichloro-phenyl)-methyl]-(3-imidazol-1-yl-propyl)-amine, Example 2 [[1-(4-Chloro-benzyl)-1H-tetrazol-5-yl]-(2,4-dimethyl-phenyl)-methyl]-(3-imidazol-1-yl-propyl)-amine, Example 3 2-[[1-(4-Chloro-benzyl)-1H-tetrazol-5-yl]-(3-imidazol-1-yl-propylamino)-methyl]-4-methyl-phenol, Example 4 2-[[1-(4-Chloro-benzyl)-1H-tetrazol-5-yl]-(3-imidazol-1-yl-propylamino)-methyl]-quinolin-8-ol, Example 5 5-[[1-(4-Chloro-benzyl)-1H-tetrazol-5-yl]-(3-imidazol-1-yl-propylamino)-methyl]-2-fluoro-benzonitrile, Example 6 [[1-(4-Chloro-benzyl)-1H-tetrazol-5-yl]-(1H-indol-5-yl)-methyl]-(3-imidazol-1-yl-propyl)-amine, Example 7 {[-(4-Chloro-benzyl)-1H-tetrazol-5-yl]-quinolin-2-yl-methyl}-(3-imidazol-1-yl-propyl)-amine, Example 8 [[1-(4-Chloro-benzyl)-1H-tetrazol-5-yl]-((S)-2-methyl-cyclohex-2-enyl)-methyl]-(3-imidazol-1-yl-propyl)-amine, Example 9 {(S)-[1-(4-Chloro-benzyl)-1H-tetrazol-5-yl]-3,4-dihydro-2H-pyran-2-yl-methyl}-(3-imidazol-1-yl-propyl)-amine, Example 10 ((3,4-Dichloro-phenyl)-{1-[(S)-1-(tetrahydro-furan-2-yl)methyl]-1H-tetrazol-5-yl}-methyl)-(3-imidazol-1-yl-propyl)-amine, Example 11 2-((3-Imidazol-1-yl-propylamino)-{1-[(S)-1-(tetrahydro-furan-2-yl)methyl]-1H-tetrazol-5-yl}-methyl)-4-methyl-phenol, Example 12 2-((3-Imidazol-1-yl-propylamino)-{1-[(S)-1-(tetrahydro-furan-2-yl)methyl]-1H-tetrazol-5-yl}-methyl)-quinolin-8-ol, Example 13 (3-Imidazol-1-yl-propyl)-((1H-indol-5-yl)-{1-[(S)-1-(tetrahydro-furan-2-yl)methyl]-1H-tetrazol-5-yl}-methyl)-amine Example 14 (3-Imidazol-1-yl-propyl)-(quinolin-2-yl-{1-[(S)-1-(tetrahydro-furan-2-yl)methyl]-1H-tetrazol-5-yl}-methyl)-amine, Example 15 (Benzofuran-2-yl-{1-[(S)-1-(tetrahydro-furan-2-yl)methyl]-1H-tetrazol-5-yl}-methyl)-(3-imidazol-1-yl-propyl)-amine, Example 16 (3-Imidazol-1-yl-propyl)-((6-methyl-1H-indol-3-yl)-{1-[(S)-1-(tetrahydro-furan-2-yl)methyl]-1H-tetrazol-5-yl}-methyl)-amine, Example 17 (3-Imidazol-1-yl-propyl)-[{1-[(S)-1-(tetrahydro-furan-2-yl)methyl]-1H-tetrazol-5-yl}-(2,4,5-trimethyl-phenyl)-methyl]-amine, Example 18 [(1-Butyl-1H-tetrazol-5-yl)-(3,4-dichloro-phenyl)-methyl]-(3-imidazol-1-yl-propyl)-amine, Example 19 2-[(1-Butyl-1H-tetrazol-5-yl)-(3-imidazol-1-yl-propylamino)-methyl]-4-methyl-phenol, Example 20 2-[(1-Butyl-1H-tetrazol-5-yl)-(3-imidazol-1-yl-propylamino)-methyl]-quinolin-8-ol, Example 21 [(1-Butyl-1H-tetrazol-5-yl)-(1H-indol-5-yl)-methyl]-(3-imidazol-1-yl-propyl)-amine Example 22 [(1-Butyl-1H-tetrazol-5-yl)-quinolin-2-yl-methyl]-(3-imidazol-1-yl-propyl)-amine, Example 23 [Benzofuran-2-yl-(1-butyl-1H-tetrazol-5-yl)-methyl]-(3-imidazol-1-yl propyl)-amine, Example 24 [(1-Butyl-1H-tetrazol-5-yl)-(2,4,5-trimethyl-phenyl)-methyl]-(3-imidazol-1-yl-propyl)-amine, Example 25 2-[(1-Cyclopentyl-1H-tetrazol-5-yl)-(3-imidazol-1-yl-propylamino)-methyl]-quinolin-8-ol, Example 26 [(1-Cyclopentyl-1H-tetrazol-5-yl)-(1H-indol-5-yl)-methyl]-(3-imidazol-1-yl-propyl)-amine, Example 27 [(1-Cyclopentyl-1H-tetrazol-5-yl)-((S)-2-methyl-cyclohex-2-enyl)-methyl]-(3-imidazol-1-yl-propyl)-amine, Example 28 [(S)-(1-Cyclopentyl-1H-tetrazol-5-yl)-3,4-dihydro-2H-pyran-2-yl-methyl]-(3-imidazol-1-yl-propyl)-amine, Example 29 2-[(3-Imidazol-1-yl-propylamino)-(1-methyl-1H-tetrazol-5-yl)-methyl]-quinolin-8-ol, Example 30 (3-Imidazol-1-yl-propyl)-[(1H-indol-5-yl)-(1-methyl-1H-tetrazol-5-yl)-methyl]-amine, Example 31 (3-Imidazol-1-yl-propyl)-[(1-methyl-1H-tetrazol-5-yl)-quinolin-2-yl-methyl]-amine, Example 32 {(3,4-Dichloro-phenyl)-[1-(3-methoxy-propyl)-1H-tetrazol-5-yl]-methyl}-(3-imidazol-1-yl-propyl)-amine, Example 33 2-{(3-Imidazol-1-yl-propylamino)-[1-(3-methoxy-propyl)-1H-tetrazol-5-yl]-methyl}-4-methyl-phenol, Example 34 2-{(3-Imidazol-1-yl-propylamino)-[1-(3-methoxy-propyl)-1H-tetrazol-5-yl]-methyl}-quinolin-8-ol, Example 35 (3-Imidazol-1-yl-propyl)-{(1H-indol-5-yl)-[1-(3-methoxy-propyl)-1H-tetrazol-5-yl]-methyl}-amine, Example 36 (3-Imidazol-1-yl-propyl)-{[1-(3-methoxy-propyl)-1H-tetrazol-5-yl]-quinolin-2-yl-methyl}-amine, Example 37 2-[[1-(2-Dimethylamino-ethyl)-1H-tetrazol-5-yl]-(3-imidazol-1-yl-propylamino)-methyl]-quinolin-8-ol, Example 38 {(S)-3,4-Dihydro-2H-pyran-2-yl-[1-(2-dimethylamino-ethyl)-1H-tetrazol-5-yl]-methyl}-(3-imidazol-1-yl-propyl)-amine, Example 39 2-{(3-Imidazol-1-yl-propylamino)-[1-(2-methoxy-ethyl)-1H-tetrazol-5-yl]-methyl}-4-methyl-phenol, Example 40 2-{(3-Imidazol-1-yl-propylamino)-[1-(2-methoxy-ethyl)-1H-tetrazol-5-yl]-methyl}-quinolin-8-ol, Example 41 (3-Imidazol-1-yl-propyl)-{(1H-indol-5-yl)-[1-(2-methoxy-ethyl)-1H-tetrazol-5-yl]-methyl}-amine, Example 42 (3-Imidazol-1-yl-propyl)-{[1-(2-methoxy-ethyl)-1H-tetrazol-5-yl]-quinolin-2-yl-methyl}-amine, Example 43 (3-Imidazol-1-yl-propyl)-[[1-(2-methoxy-ethyl)-1H-tetrazol-5-yl]-(2,4,5-trimethyl-phenyl)-methyl]-amine, Example 44 2-[(1-Allyl-1H-tetrazol-5-yl)-(3-imidazol-1-yl-propylamino)-methyl]-4-methyl-phenol, Example 45 2-[(1-Allyl-1H-tetrazol-5-yl)-(3-imidazol-1-yl-propylamino)-methyl]-quinolin-8-ol, Example 46 [(1-Allyl-1H-tetrazol-5-yl)-(1H-indol-5-yl)-methyl]-(3-imidazol-1-yl-propyl)-amine, Example 47 [(1-Allyl-1H-tetrazol-5-yl)-quinolin-2-yl-methyl]-(3-imidazol-1-yl-propyl)-amine, Example 48 [(1-Allyl-1H-tetrazol-5-yl)-(2,4,5-trimethyl-phenyl)-methyl]-(3-imidazol-1-yl-propyl)-amine, Example 49 {5-[1-(3-Imidazol-1-yl-propylamino)-cyclobutyl]-tetrazol-1-yl}-acetic methyl ester, Example 50 {5-[(3,4-Dichloro-phenyl)-(3-imidazol-1-yl-propylamino)-methyl]-tetrazol-1-yl}-acetic methyl ester, Example 51 {5-[(2-Hydroxy-5-methyl-phenyl)-(3-imidazol-1-yl-propylamino)-methyl]-tetrazol-1-yl}-acetic methyl ester, Example 52 {5-[(8-Hydroxy-quinolin-2-yl)-(3-imidazol-1-yl-propylamino)-methyl]tetrazol-1-yl}-acetic methyl ester, Example 53 {5-[(3-Cyano-4-fluoro-phenyl)-(3-imidazol-1-yl-propylamino)-methyl]-tetrazol-1-yl}-acetic methyl ester, Example 54 {5-[(3-Imidazol-1-yl-propylamino)-(1H-indol-5-yl)-methyl]-tetrazol-1-yl}-acetic methyl ester, Example 55 {5-[(3-Imidazol-1-yl-propylamino)-quinolin-2-yl-methyl]-tetrazol-1-yl}-acetic methyl ester, Example 56 {5-[(S)-3,4-Dihydro-2H-pyran-2-yl-(3-imidazol-1-yl-propylamino)-methyl]-tetrazol-1-yl}-acetic methyl ester, Example 57 {5-[Cyclopropyl-(3-imidazol-1-yl-propylamino)-methyl]-tetrazol-1-yl}-acetic methyl ester, Example 58 {5-[(3-Hydroxy-4-methoxy-phenyl)-(3-imidazol-1-yl-propylamino)-methyl]-tetrazol-1-yl}-acetic methyl ester, Example 59 2-[(1-tert-Butyl-1H-tetrazol-5-yl)-(3-imidazol-1-yl-propylamino)-methyl]-4-methyl-phenol, Example 60 2-[(1-tert-Butyl-1H-tetrazol-5-yl)-(3-imidazol-1-yl-propylamino)-methyl]-quinolin-8-ol, Example 61 [(S)-(1-tert-Butyl-1H-tetrazol-5-yl)-3,4-dihydro-2H-pyran-2-yl-methyl]-(3-imidazol-1-yl-propyl)-amine, Example 62 [(1-tert-Butyl-1H-tetrazol-5-yl)-(2,4-dimethoxy-pyrimidin-5-yl)-methyl]-(3-imidazol-1-yl-propyl)-amine, Example 63 2-[[1-(2,2-Dimethyl-propyl)-1H-tetrazol-5-yl]-(3-imidazol-1-yl-propylamino)-methyl]-4-methyl-phenol, Example 64 2-[[1-(2,2-Dimethyl-propyl)-1H-tetrazol-5-yl]-(3-imidazol-1-yl-propylamino)-methyl]-quinolin-8-ol, Example 65 [[1-(2,2-Dimethyl-propyl)-1H-tetrazol-5-yl]-(1H-indol-5-yl)-methyl]-(3-imidazol-1-yl-propyl)-amine, Example 66 {[1-(2,2-Dimethyl-propyl)-1H-tetrazol-5-yl]-quinolin-2-yl-methyl}-(3-imidazol-1-yl-propyl)-amine, Example 67 {(S)-3,4-Dihydro-2H-pyran-2-yl-[1-(2,2-dimethyl-propyl)-1H-tetrazol-5-yl]-methyl}-(3-imidazol-1-yl-propyl)-amine, Example 68 2-[(1-Cyclopropyl-1H-tetrazol-5-yl)-(3-imidazol-1-yl-propylamino)-methyl]-4-methyl-phenol, Example 69 [(1-Cyclopropyl-1H-tetrazol-5-yl)-(1H-indol-5-yl)-methyl]-(3-imidazol-1-yl-propyl)-amine, Example 70 [(1-Cyclopropyl-1H-tetrazol-5-yl)-quinolin-2-yl-methyl]-(3-imidazol-1-yl-propyl)-amine, Example 71 [(S)-(1-Cyclopropyl-1H-tetrazol-5-yl)-3,4-dihydro-2H-pyran-2-yl-methyl]-(3-imidazol-1-yl-propyl)-amine, Example 72 (1H-Benzoimidazol-5-yl)-[(1-cyclohexyl-1H-tetrazol-5-yl)-(4-methoxy-phenyl)-methyl]-amine, Example 73 (1H-Benzoimidazol-5-yl)-[2-phenyl-1-(1-pyridin-3-ylmethyl-1H-tetrazol-5-yl)-ethyl]-amine, Example 74 (1H-Benzoimidazol-5-yl)-[(3-propoxy-phenyl)-(1-pyridin-3-ylmethyl-1H-tetrazol-5-yl)-methyl]-amine, Example 75 (1H-Benzoimidazol-5-yl)-[[1-(4-chloro-benzyl)-1H-tetrazol-5-yl]-(4-methoxy-2-methyl-phenyl)-methyl]-amine, Example 76 (1H-Benzoimidazol-5-yl)-{(4-pyridin-2-yl-phenyl)-[1-(tetrahydro-furan-2-ylmethyl)-1H-tetrazol-5-yl]-methyl}-amine, Example 77 (1H-Benzoimidazol-5-yl)-[[1-(2-chloro-benzyl)-1H-tetrazol-5-yl]-(4-methoxy-2-methyl-phenyl)-methyl]-amine, Example 78 {Benzo[b]thiophen-3-yl-[1-(tetrahydro-furan-2-ylmethyl)-1H-tetrazol-5-yl]-methyl}-(1H-benzoimidazol-5-yl)-amine, Example 79 [Benzofuran-2-yl-(1-cyclohexyl-1H-tetrazol-5-yl)-methyl]-(1H-benzoimidazol-5-yl)-amine, Example 80 (1H-Benzoimidazol-5-yl)-{(6-methyl-1H-indol-3-yl)-[1-(tetrahydro-furan-2-ylmethyl)-1H-tetrazol-5-yl]-methyl}-amine, Example 81 (1H-Benzoimidazol-5-yl)-[(1-cyclohexyl-1H-tetrazol-5-yl)-(6-fluoro-1H-indol-3-yl)-methyl]-amine, Example 82 (1H-Benzoimidazol-5-yl)-[(4-ethyl-phenyl)-(1-pyridin-3-ylmethyl-1H-tetrazol-5-yl)-methyl]-amine, Example 83 (1H-Benzoimidazol-5-yl)-{(3,4-dimethyl-phenyl)-[1-(tetrahydro-furan-2-ylmethyl)-1H-tetrazol-5-yl]-methyl}-amine, Example 84 2-{5-[(1H-Benzoimidazol-5-ylamino)-(4-chloro-3-fluoro-phenyl)-methyl]-tetrazol-1-yl}-cyclohexanecarboxylic acid ethyl ester, Example 85 3-{(1H-Benzoimidazol-5-ylamino)-[1-(4-chloro-benzyl)-1H-tetrazol-5-yl]-methyl}-benzoic acid methyl ester, Example 86 3-{(1H-Benzoimidazol-5-ylamino)-[1-(tetrahydro-furan-2-ylmethyl)-1H-tetrazol-5-yl]-methyl}-6-methyl-chromen-4-one, Example 87 {5-[(1H-Benzoimidazol-5-ylamino)-(4-bromo-phenyl)-methyl]-tetrazol-1-yl}-acetic acid tert-butyl ester, Example 88 (1H-Benzoimidazol-5-yl)-{(4-methoxy-phenyl)-[1-(tetrahydro-furan-2-ylmethyl)-1H-tetrazol-5-yl]-methyl}-amine, Example 89 (1H-Benzoimidazol-5-yl)-{(3-methoxy-phenyl)-[1-(tetrahydro-furan-2-ylmethyl)-1H-tetrazol-5-yl]-methyl}-amine, Example 90 {Benzofuran-2-yl-[1-(2-chloro-benzyl)-1H-tetrazol-5-yl]-methyl}-(1H-benzoimidazol-5-yl)-amine, Example 91 {5-[(1H-Benzoimidazol-5-ylamino)-(4-chloro-3-fluoro-phenyl)-methyl]-tetrazol-1-yl}-acetic acid tert-butyl ester, Example 92 (1H-Benzoimidazol-5-yl)-{(2E,4E)-1-[1-(2,2-dimethyl-[1,3]dioxolan-4-ylmethyl)-1H-tetrazol-5-yl]-hexa-2,4-dienyl}-amine, Example 93 {3-Benzo[1,3]dioxol-5-yl-2-methyl-1-[1-(tetrahydro-furan-2-ylmethyl)-1H-tetrazol-5-yl]-propyl}-(1H-benzoimidazol-5-yl)-amine, Example 94 2-{5-[(1H-Benzoimidazol-5-ylamino)-(4-chloro-phenyl)-methyl]-tetrazol-1-yl}-cyclohexanecarboxylic acid ethyl ester, Example 95 [1-(1-Benzhydryl-1H-tetrazol-5-yl)-3-methylsulfanyl-propyl]-(1H-benzoimidazol-5-yl)-amine, Example 96 (1H-Benzoimidazol-5-yl)-[1-(1-cyclohexyl-1H-tetrazol-5-yl)-3-(5-methyl-furan-2-yl)-butyl]-amine, Example 97 (1H-Benzoimidazol-5-yl)-{3-phenyl-1-[1-(tetrahydro-furan-2-ylmethyl)-1H-tetrazol-5-yl-butyl}-amine, Example 98 2-{5-[1-(1H-Benzoimidazol-5-ylamino)-2-methyl-pentyl]-tetrazol-1-yl}-1-(3,4-dihydro-1H-isoquinolin-2-yl)-ethanone, Example 99 (1H-Benzoimidazol-5-yl)-[(1-tert-butyl-1H-tetrazol-5-yl)-(4-methoxy-2,5-dimethyl-phenyl)-methyl]-amine, Example 100 (1H-Benzoimidazol-5-yl)-{2-phenyl-1-[1-(tetrahydro-furan-2-ylmethyl)-1H-tetrazol-5-yl]-propyl}-amine, Example 101 {Benzofuran-2-yl-[1-(tetrahydro-furan-2-ylmethyl)-1H-tetrazol-5-yl]-methyl}-(1H-benzoimidazol-5-yl)-amine, Example 102 (1H-Benzoimidazol-5-yl)-{quinolin-3-yl-[1-(tetrahydro-furan-2-ylmethyl)-1H-tetrazol-5-yl]-methyl}-amine, Example 103 2-{5-[(1H-Benzoimidazol-5-ylamino)-(4-bromo-phenyl)-methyl]-tetrazol-1-yl}-cyclohexanecarboxylic acid ethyl ester, Example 104 2-{(1H-Benzoimidazol-5-ylamino)-[1-(2-thiophen-2-yl-ethyl)-1H-tetrazol-5-yl]-methyl}-cyclopropanecarboxylic acid ethyl ester, Example 105 (1H-Benzoimidazol-5-yl)-{benzo[c][1,2,5]thiadiazol-5-yl-[1-(tetrahydro-furan-2-ylmethyl)-1H-tetrazol-5-yl]-methyl}-amine, Example 106 (1H-Benzoimidazol-5-yl)-[1-(1-tert-butyl-1H-tetrazol-5-yl)-3-phenyl-butyl]-amine, Example 107 (1H-Benzoimidazol-5-yl)-[(4-chloro-3-fluoro-phenyl)-(1-cyclohexyl-1H-tetrazol-5-yl)-methyl]-amine, Example 108 (1H-Benzoimidazol-5-yl)-{(4-dimethylamino-phenyl)-[1-(tetrahydro-furan-2-ylmethyl)-1H-tetrazol-5-yl]-methyl}-amine, Example 109 (1H-Benzoimidazol-5-yl)-{(3-bromo-4-methoxy-phenyl)-[1-(tetrahydro-furan-2-ylmethyl)-1H-tetrazol-5-yl]-methyl}-amine, Example 110 (1H-Benzoimidazol-5-yl)-[1-(1-benzyl-1H-tetrazol-5-yl)-butyl]-amine, Example 111 (1H-Benzoimidazol-5-yl)-{3-(5-methyl-furan-2-yl)-1-[1-(tetrahydro-furan-2-ylmethyl)-1H-tetrazol-5-yl]-butyl}-amine, Example 112 [(1-Benzhydryl-1H-tetrazol-5-yl)-benzo[c][1,2,5]thia-diazol-5-yl-methyl]-(1H-benzoimidazol-5-yl)-amine, Example 113 {3-Benzo[1,3]dioxol-5-yl-1-[1-(2-chloro-benzyl)-1H-tetrazol-5-yl]-2-methyl-propyl}-(1H-benzoimidazol-5-yl)-amine, Example 114 (1H-Benzoimidazol-5-yl)-[(1-cyclohexyl-1H-tetrazol-5-yl)-(3,4-dihydro-2H-pyran-2-yl)-methyl]-amine, Example 115 (1H-Benzoimidazol-5-yl)-[(4-dimethylamino-phenyl)-(1-pyridin-3-ylmethyl-1H-tetrazol-5-yl)-methyl]-amine, Example 116 [3-Benzo[1,3]dioxol-5-yl-1-(1-cyclohexyl-1H-tetrazol-5-yl)-2-methyl-propyl]-(1H-benzoimidazol-5-yl)-amine, Example 117 (1H-Benzoimidazol-5-yl)-{benzo[c][1,2,5]thiadiazol-5-yl-[1-(4-tert-butyl-phenyl)-1H-tetrazol-5-yl]-methyl}-amine, Example 118 {Benzo[1,3]dioxol-5-yl-[1-(tetrahydro-furan-2-ylmethyl)-1H-tetrazol-5-yl]-methyl}-(1H-benzoimidazol-5-yl)-amine, Example 119 {5-[Benzo[1,3]dioxol-5-yl-(1H-benzoimidazol-5-ylamino)-methyl]-tetrazol-1-yl}-acetic acid tert-butyl ester, Example 120 2-{5-[(1H-Benzoimidazol-5-ylamino)-thiophen-2-yl-methyl]-tetrazol-1-yl}-1-(3,4-dihydro-1H-isoquinolin-2-yl)-ethanone, Example 121 (5-{(1H-Benzoimidazol-5-ylamino)-[1-(4-chloro-benzyl)-1H-tetrazol-5-yl]-methyl}-furan-2-yl)-methanol, Example 122 3-{(1H-Benzoimidazol-5-ylamino)-[1-(2-thiophen-2-yl-ethyl)-1H-tetrazol-5-yl]-methyl}-chromen-4-one, Example 123 [Benzo[b]thiophen-3-yl-(1-tert-butyl-1H-tetrazol-5-yl)-methyl]-(1H-benzoimidazol-5-yl)-amine, Example 124 (1H-Benzoimidazol-5-yl)-[(1-benzyl-1H-tetrazol-5-yl)-(3,5-dimethyl-phenyl)-methyl]-amine, Example 125 (1H-Benzoimidazol-5-yl)-[[1-(4-chloro-benzyl)-1H-tetrazol-5-yl]-(3-fluoro-4-methoxy-phenyl)-methyl]-amine, Example 126 [(1-Benzhydryl-1H-tetrazol-5-yl)-quinolin-3-yl-methyl]-(1H-benzoimidazol-5-yl)-amine, Example 127 (1H-Benzoimidazol-5-yl)-[[1-(2-chloro-benzyl)-1H-tetrazol-5-yl]-(4-chloro-phenyl)-methyl]-amine, Example 128 3-{(1H-Benzoimidazol-5-ylamino)-[1-(4-tert-butyl-phenyl)-1H-tetrazol-5-yl]-methyl}-benzoic acid methyl ester, Example 129 (1H-Benzoimidazol-5-yl)-{(5-ethyl-thiophen-2-yl)-[1-(tetrahydro-furan-2-ylmethyl)-1H-tetrazol-5-yl]-methyl}-amine, Example 130 (1H-Benzoimidazol-5-yl)-[[1-(2,2-dimethyl-[1,3]dioxolan-4-ylmethyl)-1H-tetrazol-5-yl]-(4-methylsulfanyl-phenyl)-methyl]-amine, Example 131 4-{(1H-Benzoimidazol-5-ylamino)-[1-(tetrahydro-furan-2-ylmethyl)-1H-tetrazol-5-yl]-methyl}-2,6-dimethyl-phenol, Example 132 2-{5-[(1H-Benzoimidazol-5-ylamino)-(3-fluoro-4-methoxy-phenyl)-methyl]-tetrazol-1-yl}-cyclohexanecarboxylic acid ethyl ester, Example 133 (1H-Benzoimidazol-5-yl)-[(1-benzyl-1H-tetrazol-5-yl)-(5-ethyl-thiophen-2-yl)-methyl]-amine, Example 134 (1H-Benzoimidazol-5-yl)-{(4-pyrrolidin-1-yl-phenyl)-[1-(tetrahydro-furan-2-ylmethyl)-1H-tetrazol-5-yl]-methyl}-amine, Example 135 (1H-Benzoimidazol-5-yl)-{[1-(2-chloro-benzyl)-1H-tetrazol-5-yl]-pyridin-3-yl-methyl}-amine, Example 136 (1H-Benzoimidazol-5-yl)-[[1-(4-chloro-benzyl)-1H-tetrazol-5-yl]-(4-chloro-phenyl)-methyl]-amine, Example 137 2-{5-[(1H-Benzoimidazol-5-ylamino)-(3,5-dimethyl-phenyl)-methyl]-tetrazol-1-yl}-1-(3,4-dihydro-1H-isoquinolin-2-yl)-ethanone, Example 138 {Benzo[1,3]dioxol-5-yl-[1-(2,2-dimethyl-[1,3]dioxolan-4-ylmethyl)-1H-tetrazol-5-yl]-methyl}-(1H-benzoimidazol-5-yl)-amine, Example 139 {Benzo[1,3]dioxol-5-yl-[1-(4-phenoxy-phenyl)-1H-tetrazol-5-yl]-methyl}-(1H-benzoimidazol-5-yl)-amine, Example 140 (1H-Benzoimidazol-5-yl)-{(4-methylsulfanyl-phenyl)-[1-(tetrahydro-furan-2-ylmethyl)-1H-tetrazol-5-yl]-methyl}-amine, Example 141 (1H-Benzoimidazol-5-yl)-{(3-propoxy-phenyl)-[1-(tetrahydro-furan-2-ylmethyl)-1H-tetrazol-5-yl]-methyl}-amine, Example 142 (1H-Benzoimidazol-5-yl)-[(3-bromo-4-methoxy-phenyl)-(1-pyridin-3-ylmethyl-1H-tetrazol-5-yl)-methyl]-amine, Example 143 (5-{(1H-Benzoimidazol-5-ylamino)-[1-(2-benzyloxy-phenyl)-1H-tetrazol-5-yl]-methyl}-furan-2-yl)-methanol, Example 144 (1H-Benzoimidazol-5-yl)-{(6-fluoro-1H-indol-3-yl)-[1-(tetrahydro-furan-2-ylmethyl)-1H-tetrazol-5-yl]-methyl}-amine, Example 145 2-{5-[Benzo[b]thiophen-3-yl-(1H-benzoimidazol-5-ylamino)-methyl]-tetrazol-1-yl}-cyclohexanecarboxylic acid ethyl ester, Example 146 (1H-Benzoimidazol-5-yl)-{(4-chloro-3-nitro-phenyl)-[1-(tetrahydro-furan-2-ylmethyl)-1H-tetrazol-5-yl]-methyl}-amine, Example 147 (1H-Benzoimidazol-5-yl)-[benzo[c][1,2,5]thiadiazol-5-yl-(1-benzyl-1H-tetrazol-5-yl)-methyl]-amine, Example 148 (1H-Benzoimidazol-5-yl)-[[1-(2-chloro-benzyl)-1H-tetrazol-5-yl]-(4-chloro-3-nitro-phenyl)-methyl]-amine Example 149 {5-[3-Benzo[1,3]dioxol-5-yl-1-(1H-benzoimidazol-5-ylamino)-2-methyl-propyl]-tetrazol-1-yl}-acetic acid tert-butyl ester, Example 150 2-{5-[(1H-Benzoimidazol-5-ylamino)-(4-methylsulfanyl-phenyl)-methyl]-tetrazol-1-yl}-cyclohexanecarboxylic acid ethyl ester, Example 151 (1H-Benzoimidazol-5-yl)-[(1-benzyl-1H-tetrazol-5-yl)-(2-methoxy-phenyl)-methyl]-amine, Example 152 3-{(1H-Benzoimidazol-5-ylamino)-[1-(tetrahydro-furan-2-ylmethyl)-1H-tetrazol-5-yl]-methyl}-phenol, Example 153 (1H-Benzoimidazol-5-yl)-[[1-(2-chloro-benzyl)-1H-tetrazol-5-yl]-(2-methoxy-phenyl)-methyl]-amine, Example 154 3-{(1H-Benzoimidazol-5-ylamino)-[1-(tetrahydro-furan-2-ylmethyl)-1H-tetrazol-5-yl]-methyl}-benzoic acid methyl ester, Example 155 2-{5-[(1H-Benzoimidazol-5-ylamino)-(3,4-dimethyl-phenyl)-methyl]-tetrazol-1-yl}-cyclohexanecarboxylic acid ethyl ester, Example 156 (1H-Benzoimidazol-5-yl)-{[1-(2,2-dimethyl-[1,3]dioxolan-4-ylmethyl)-1H-tetrazol-5-yl]-quinolin-3-yl-methyl}-amine, Example 157 2-{5-[(1H-Benzoimidazol-5-ylamino)-(3,5-dimethyl-phenyl)-methyl]-tetrazol-1-yl}-cyclohexanecarboxylic acid ethyl ester, Example 158 [(1-Benzhydryl-1H-tetrazol-5-yl)-pyridin-3-yl-methyl]-(1H-benzoimidazol-5-yl)-amine, Example 159 3-{(1H-Benzoimidazol-5-ylamino)-[1-(tetrahydro-furan-2-ylmethyl)-1H-tetrazol-5-yl]-methyl}-chromen-4-one, Example 160 {Benzo[1,3]dioxol-5-yl-[1-(4-chloro-benzyl)-1H-tetrazol-5-yl]-methyl}-(1H-benzoimidazol-5-yl)-amine, Example 161 (1H-Benzoimidazol-5-yl)-{(2E,4E)-1-[1-(2-thiophen-2-yl-ethyl)-1H-tetrazol-5-yl]-hexa-2,4-dienyl}-amine, Example 162 2-{5-[Benzo[1,3]dioxol-5-yl-(1H-benzoimidazol-5-ylamino)-methyl]-tetrazol-1-yl}-cyclohexanecarboxylic acid ethyl ester, Example 163 (1H-Benzoimidazol-5-yl)-{(3-fluoro-4-methoxy-phenyl)-[1-(tetrahydro-furan-2-ylmethyl)-1H-tetrazol-5-yl]-methyl}-amine, Example 164 1-(3-{5-[(1H-Benzoimidazol-5-ylamino)-(3,4-dimethyl-phenyl)-methyl]-tetrazol-1-yl}-propyl)-pyrrolidin-2-one, Example 165 4-{(1H-Benzoimidazol-5-ylamino)-[1-(2,2-dimethyl-[1,3]dioxolan-4-ylmethyl)-1H-tetrazol-5-yl]-methyl}-2,6-dimethyl-phenol, Example 166 (1H-Benzoimidazol-5-yl)-{benzo[c][1,2,5]thiadiazol-5-yl-[1-(4-chloro-benzyl)-1H-tetrazol-5-yl]-methyl}-amine, Example 167 (1H-Benzoimidazol-5-yl)-{cyclohex-3-enyl-[1-(2-thiophen-2-yl-ethyl)-1H-tetrazol-5-yl]-methyl}-amine, Example 168 2-{5-[(1H-Benzoimidazol-5-ylamino)-(4-ethyl-phenyl)-methyl]-tetrazol-1-yl}-cyclohexanecarboxylic acid ethyl ester, Example 169 2-{5-[(1H-Benzoimidazol-5-ylamino)-(5-chloro-2-hydroxy-phenyl)-methyl]-tetrazol-1-yl}-cyclohexanecarboxylic acid ethyl ester,
Example 170 (1H-Benzoimidazol-5-yl)-{(3,5-dibromo-phenyl)-[1-(tetrahydro-furan-2-ylmethyl)-1H-tetrazol-5-yl]-methyl}-amine,
Example 171 (1H-Benzoimidazol-5-yl)-{(4-chloro-3-nitro-phenyl)-[1-(2,2-dimethyl-[1,3]dioxolan-4-ylmethyl)-1H-tetrazol-5-yl]-methyl}-amine,
Example 172 {5-[(1H-Benzoimidazol-5-ylamino)-(4-methoxy-phenyl)-methyl]-tetrazol-1-yl}-acetic acid tert-butyl ester,
Example 173 (1H-Benzoimidazol-5-yl)-[(2E,4E)-1-(1-pyridin-3-ylmethyl-1H-tetrazol-5-yl)-hexa-2,4-dienyl]-amine,
Example 174 (1H-Benzoimidazol-5-yl)-{(2E,4E)-1-[1-(tetrahydro-furan-2-ylmethyl)-1H-tetrazol-5-yl]-hexa-2,4-dienyl}-amine,
Example 175 (1H-Benzoimidazol-5-yl)-[(1-cyclohexyl-1H-tetrazol-5-yl)-(3,5-dibromo-phenyl)-methyl]-amine,
Example 176 1-(3-{5-[(1H-Benzoimidazol-5-ylamino)-(3,5-dibromo-phenyl)-methyl]-tetrazol-1-yl}-propyl)-pyrrolidin-2-one,
Example 177 (1H-Benzoimidazol-5-yl)-{(3,5-dibromo-phenyl)-[1-(2-thiophen-2-yl-ethyl)-1H-tetrazol-5-yl]-methyl}-amine,
Example 178 (1H-Benzoimidazol-5-yl)-{(3,5-dibromo-phenyl)-[1-(4-phenoxy-phenyl)-1H-tetrazol-5-yl]-methyl}-amine,
Example 179 (1H-Benzoimidazol-5-yl)-{(3,5-dibromo-phenyl)-[1-(2,3-dihydro-benzo[1,4]dioxin-6-yl)-1H-tetrazol-5-yl]-methyl}-amine,
Example 180 (1H-Benzoimidazol-5-yl)-[[1-(2-benzyloxy-phenyl)-1H-tetrazol-5-yl]-(3,5-dibromo-phenyl)-methyl]-amine,
Example 181 (1H-Benzoimidazol-5-yl)-{benzo[c][1,2,5]thiadiazol-5-yl-[1-(2-thiophen-2-yl-ethyl)-1H-tetrazol-5-yl]-methyl}-amine,
Example 182 (1H-Benzoimidazol-5-yl)-{(3,4-dihydro-2H-pyran-2-yl)-[1-(2-thiophen-2-yl-ethyl)-1H-tetrazol-5-yl]-methyl}-amine,
Example 183 2-{5-[(1H-Benzoimidazol-5-ylamino)-(2-methoxy-phenyl)-methyl]-tetrazol-1-yl}-cyclohexanecarboxylic acid ethyl ester,
Example 184 2-{5-[(1H-Benzoimidazol-5-ylamino)-(4-methoxy-phenyl)-methyl]-tetrazol-1-yl}-cyclohexanecarboxylic acid ethyl ester,
Example 185 (1H-Benzoimidazol-5-yl)-[benzo[c][1,2,5]thiadiazol-5-yl-(1-pyridin-3-ylmethyl-1H-tetrazol-5-yl)-methyl]-amine,
Example 186 [(1-Benzhydryl-1H-tetrazol-5-yl)-(3,5-dibromo-phenyl)-methyl]-(1H-benzoimidazol-5-yl)-amine,
Example 187 2-{5-[(1H-Benzoimidazol-5-ylamino)-(3,5-dibromo-phenyl)-methyl]-tetrazol-1-yl}-N-[2-(1H-indol-3-yl)-ethyl]-acetamide,
Example 188 (1H-Benzoimidazol-5-yl)-{(3,5-dibromo-phenyl)-[1-(3,3-diphenyl-propyl)-1H-tetrazol-5-yl]-methyl}-amine,
Example 189 (1H-Benzoimidazol-5-yl)-{(3,5-dibromo-phenyl)-[1-(4-phenyl-butyl)-1H-tetrazol-5-yl]-methyl}-amine,
Example 190 (1H-Benzoimidazol-5-yl)-[(1-benzyl-1H-tetrazol-5-yl)-(3,5-dibromo-phenyl)-methyl]-amine,
Example 191 4-{(1H-Benzoimidazol-5-ylamino)-[1-(4-chloro-benzyl)-1H-tetrazol-5-yl]-methyl}-phenol,
Example 192 2-{5-[(1H-Benzoimidazol-5-ylamino)-(3-methoxy-phenyl)-methyl]-tetrazol-1-yl}-cyclohexanecarboxylic acid ethyl ester,
Example 193 2-[(1H-Benzoimidazol-5-ylamino)-(1-cyclohexyl-1H-tetrazol-5-yl)-methyl]-4-chloro-phenol,
Example 194 1-(3-{5-[(1H-Benzoimidazol-5-ylamino)-(4-bromo-phenyl)-methyl]-tetrazol-1-yl}-propyl)-pyrrolidin-2-one,
Example 195 3-{(1H-Benzoimidazol-5-ylamino)-[1-(2-ethoxycarbonyl-cyclohexyl)-1H-tetrazol-5-yl]-methyl}-benzoic acid methyl ester,
Example 196 2-{5-[(1H-Benzoimidazol-5-ylamino)-(6-methyl-1H-indol-3-yl)-methyl]-tetrazol-1-yl}-cyclohexanecarboxylic acid ethyl ester,
Example 197 (1H-Benzoimidazol-5-yl)-[[1-(4-chloro-benzyl)-1H-tetrazol-5-yl]-(4-chloro-3-nitro-phenyl)-methyl]-amine,
Example 198 (1H-Benzoimidazol-5-yl)-[(1-cyclohexyl-1H-tetrazol-5-yl)-(4-ethyl-phenyl)-methyl]-amine,
Example 199 2-{5-[(1H-Benzoimidazol-5-ylamino)-(4-bromo-phenyl)-methyl]-tetrazol-1-yl}-1-(3,4-dihydro-1H-isoquinolin-2-yl)-ethanone,
Example 200 2-{5-[(1H-Benzoimidazol-5-ylamino)-(4-bromo-phenyl)-methyl]-tetrazol-1-yl}-N-[2-(1H-indol-3-yl)-ethyl]-acetamide,
Example 201 (1H-Benzoimidazol-5-yl)-[(4-bromo-phenyl)-(1-pyridin-3-ylmethyl-1H-tetrazol-5-yl)-methyl]-amine,
Example 202 2-{5-[1-(1H-Benzoimidazol-5-ylamino)-3-(5-methyl-furan-2-yl)-butyl]-tetrazol-1-yl}-cyclohexanecarboxylic acid ethyl ester,
Example 203 (1H-Benzoimidazol-5-yl)-[[1-(2-benzyloxy-phenyl)-1H-tetrazol-5-yl]-(4-bromo-phenyl)-methyl]-amine,
Example 204 (1H-Benzoimidazol-5-yl)-{1-[1-(4-phenoxy-phenyl)-1H-tetrazol-5-yl]-3-phenyl-butyl}-amine,
Example 205 (1H-Benzoimidazol-5-yl)-{benzo[c][1,2,5]thiadiazol-5-yl-[1-(2-chloro-benzyl)-1H-tetrazol-5-yl]-methyl}-amine,
Example 206 {Benzo[b]thiophen-3-yl-[1-(4-nitro-phenyl)-1H-tetrazol-5-yl]-methyl}-(1H-benzoimidazol-5-yl)-amine,
Example 207 (1H-Benzoimidazol-5-yl)-{(4-chloro-3-fluoro-phenyl)-[1-(2-thiophen-2-yl-ethyl)-1H-tetrazol-5-yl]-methyl}-amine,
Example 208 2-{5-[(1H-Benzoimidazol-5-ylamino)-(3-propoxy-phenyl)-methyl]-tetrazol-1-yl}-cyclohexanecarboxylic acid ethyl ester,
Example 209 2-{5-[(1H-Benzoimidazol-5-ylamino)-(4-methoxy-phenyl)-methyl]-tetrazol-1-yl}-1-(3,4-dihydro-1H-isoquinolin-2-yl)-ethanone,
Example 210 (1H-Benzoimidazol-5-yl)-[[1-(2-benzyloxy-phenyl)-1H-tetrazol-5-yl]-(4-methoxy-phenyl)-methyl]-amine,
Example 211 (1H-Benzoimidazol-5-yl)-{(4-pyridin-2-yl-phenyl)-[1-(2-thiophen-2-yl-ethyl)-1H-tetrazol-5-yl]-methyl}-amine,
Example 212 {5-[(1H-Benzoimidazol-5-ylamino)-(4-pyridin-2-yl-phenyl)-methyl]-tetrazol-1-yl}-acetic acid tert-butyl ester.

19. A compound selected from the group consisting of examples below and the pharmaceutically acceptable salts of them:

Example 1 [[1-(4-Chloro-benzyl)-1H-tetrazol-5-yl]-(3,4-dichloro-phenyl)-methyl]-(3-imidazol-1-yl-propyl)-amine, Example 6 [[1-(4-Chloro-benzyl)-1H-tetrazol-5-yl]-(1H-indol-5-yl)-methyl]-(3-imidazol-1-yl-propyl)-amine, Example 7 {[1-(4-Chloro-benzyl)-1H-tetrazol-5-yl]-quinolin-2-yl-methyl}-(3-imidazol-1-yl-propyl)-amine, Example 12 2-((3-Imidazol-1-yl-propylamino)-{1-[(S)-1-(tetrahydro-furan-2-yl)methyl]-1H-tetrazol-5-yl}-methyl)-quinolin-8-ol, Example 14 (3-Imidazol-1-yl-propyl)-(quinolin-2-yl-{1-[(S)-1-(tetrahydro-furan-2-yl)methyl]-1H-tetrazol-5-yl}-methyl)-amine, Example 19 2-[(1-Butyl-1H-tetrazol-5-yl)-(3-imidazol-1-yl-propylamino)-methyl]-4-methyl-phenol, Example 20 2-[(1-Butyl-1H-tetrazol-5-yl)-(3-imidazol-1-yl-propylamino)-methyl]-quinolin-8-ol, Example 25 2-[(1-Cyclopentyl-1H-tetrazol-5-yl)-(3-imidazol-1-yl-propylamino)-methyl]-quinolin-8-ol, Example 34 2-{(3-Imidazol-1-yl-propylamino)-[1-(3-methoxy-propyl)-1H-tetrazol-5-yl]-methyl}-quinolin-8-ol, Example 49 {5-[1-(3-Imidazol-1-yl-propylamino)-cyclobutyl]-tetrazol-1-yl}-acetic methyl ester, Example 51 {5-[(2-Hydroxy-5-methyl-phenyl)-(3-imidazol-1-yl-propylamino)-methyl]-tetrazol-1-yl}-acetic methyl ester, Example 55 {5-[(3-Imidazol-1-yl-propylamino)-quinolin-2-yl-methyl]-tetrazol-1-yl}-acetic methyl ester, Example 59 2-[(1-tert-Butyl-1H-tetrazol-5-yl)-(3-imidazol-1-yl-propylamino) methyl]-4-methyl-phenol, Example 63 2-[[1-(2,2-Dimethyl-propyl)-1H-tetrazol-5-yl]-(3-imidazol-1-yl-propylamino)-methyl]-4-methyl-phenol, Example 64 2-[[1-(2,2-Dimethyl-propyl)-1H-tetrazol-5-yl]-(3-imidazol-1-yl-propylamino)-methyl]-quinolin-8-ol, Example 72 (1H-Benzoimidazol-5-yl)-[(1-cyclohexyl-1H-tetrazol-5-yl)-(4-methoxy-phenyl)-methyl]-amine, Example 74 (1H-Benzoimidazol-5-yl)-[(3-propoxy-phenyl)-(1-pyridin-3-ylmethyl-1H-tetrazol-5-yl)-methyl]-amine, Example 75 (1H-Benzoimidazol-5-yl)-[[1-(4-chloro-benzyl)-1H-tetrazol-5-yl]-(4-methoxy-2-methyl-phenyl)-methyl]-amine, Example 77 (1H-Benzoimidazol-5-yl)-[[1-(2-chloro-benzyl)-1H-tetrazol-5-yl]-(4-methoxy-2-methyl-phenyl)-methyl]-amine, Example 78 {Benzo[b]thiophen-3-yl-[1-(tetrahydro-furan-2-ylmethyl)-1H-tetrazol-5-yl]-methyl}-(1H-benzoimidazol-5-yl)-amine, Example 85 3-{(1H-Benzoimidazol-5-ylamino)-[1-(4-chloro-benzyl)-1H-tetrazol-5-yl]-methyl}-benzoic acid methyl ester, Example 87 {5-[(1H-Benzoimidazol-5-ylamino)-(4-bromo-phenyl)-methyl]-tetrazol-1-yl}-acetic acid tert-butyl ester, Example 90 {Benzofuran-2-yl-[1-(2-chloro-benzyl)-1H-tetrazol-5-yl]-methyl}-(1H-benzoimidazol-5-yl)-amine, Example 102 (1H-Benzoimidazol-5-yl)-{quinolin-3-yl-[1-(tetrahydro-furan-2-ylmethyl)-1H-tetrazol-5-yl]-methyl}-amine, Example 109 (1H-Benzoimidazol-5-yl)-{(3-bromo-4-methoxy-phenyl)-[1-(tetrahydro-furan-2-ylmethyl)-1H-tetrazol-5-yl]-methyl}-amine, Example 119 {5-[Benzo[1,3]dioxol-5-yl-(1H-benzoimidazol-5-ylamino)-methyl]-tetrazol-1-yl}-acetic acid tert-butyl ester, Example 142 (1H-Benzoimidazol-5-yl)-[(3-bromo-4-methoxy-phenyl)-(1-pyridin-3-ylmethyl-1H-tetrazol-5-yl)-methyl]-amine, Example 145 2-{5-[Benzo[b]thiophen-3-yl-(1H-benzoimidazol-5-ylamino)-methyl]-tetrazol-1-yl}-cyclohexanecarboxylic acid ethyl ester, Example 147 (1H-Benzoimidazol-5-yl)-[benzo[c][1,2,5]thiadiazol-5-yl-(1-benzyl-1H-tetrazol-5-yl)-methyl]-amine, Example 148 (1H-Benzoimidazol-5-yl)-[[1-(2-chloro-benzyl)-1H-tetrazol-5-yl]-(4-chloro-3-nitro-phenyl)-methyl]-amine Example 160 {Benzo[1,3]dioxol-5-yl-[1-(4-chloro-benzyl)-1H-tetrazol-5-yl]-methyl}-(1H-benzoimidazol-5-yl)-amine, Example 166 (1H-Benzoimidazol-5-yl)-{benzo[c][1,2,5]thiadiazol-5-yl-[1-(4-chloro-benzyl)-1H-tetrazol-5-yl]-methyl}-amine, Example 177 (1H-Benzoimidazol-5-yl)-{(3,5-dibromo-phenyl)-[1-(2-thiophen-2-yl-ethyl)-1H-tetrazol-5-yl]-methyl}-amine, Example 181 (1H-Benzoimidazol-5-yl)-{benzo[c][1,2,5]thiadiazol-5-yl-[1-(2-thiophen-2-yl-ethyl)-1H-tetrazol-5-yl]-methyl}-amine, Example 187 2-{5-[(1H-Benzoimidazol-5-ylamino)-(3,5-dibromo-phenyl)-methyl]-tetrazol-1-yl}-N-[2-(1H-indol-3-yl)-ethyl]-acetamide, Example 190 (1H-Benzoimidazol-5-yl)-[(1-benzyl-1H-tetrazol-5-yl)-(3,5-dibromo-phenyl)-methyl]-amine, Example 197 (1H-Benzoimidazol-5-yl)-[[1-(4-chloro-benzyl)-1H-tetrazol-5-yl]-(4-chloro-3-nitro-phenyl)-methyl]-amine, Example 199 2-{5-[(1H-Benzoimidazol-5-ylamino)-(4-bromo-phenyl)-methyl]-tetrazol-1-yl}-1-(3,4-dihydro-1H-isoquinolin-2-yl)-ethanone, Example 200 2-{5-[(1H-Benzoimidazol-5-ylamino)-(4-bromo-phenyl)-methyl]-tetrazol-1-yl}-N-[2-(1H-indol-3-yl)-ethyl]-acetamide, Example 203 (1H-Benzoimidazol-5-yl)-[[1-(2-benzyloxy-phenyl)-1H-tetrazol-5-yl]-(4-bromo-phenyl)-methyl]-amine, Example 205 (1H-Benzoimidazol-5-yl)-{benzo[c][1,2,5]thiadiazol-5-yl-[1-(2-chloro-benzyl)-1H-tetrazol-5-yl]-methyl}-amine, Example 208 2-{5-[(1H-Benzoimidazol-5-ylamino)-(3-propoxy-phenyl)-methyl]-tetrazol-1-yl}-cyclohexanecarboxylic acid ethyl ester, Example 210 (1H-Benzoimidazol-5-yl)-[[1-(2-benzyloxy-phenyl)-1H-tetrazol-5-yl]-(4-methoxy-phenyl)-methyl]-amine, Example 211 (1H-Benzoimidazol-5-yl)-{(4-pyridin-2-yl-phenyl)-[1-(2-thiophen-2-yl-ethyl)-1H-tetrazol-5-yl]-methyl}-amine, and Example 212 {5-[(1H-Benzoimidazol-5-ylamino)-(4-pyridin-2-yl-phenyl)-methyl]-tetrazol-1-yl}-acetic acid tert-butyl ester.

20. A pharmaceutical composition comprising a compound according to claim 1 in combination with one or more therapeutically acceptable diluents or carriers.

21. The pharmaceutical composition of claim 20, which comprises additionally at least one compound, selected from the group consisting of neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

22. The pharmaceutical composition of claim 21, which comprises additionally at least one compound, selected from the group consisting of prolyl endopeptidase (PEP)-inhibitors, LiCl, inhibitors of dipeptidyl aminopeptidases, preferably inhibitors of dipeptidyl peptidase (DP) IV or DP IV-like enzymes, acetylcholinesterase (ACE) inhibitors, protein-L-isoaspartyl methyltransferase (PIMT) enhancers, inhibitors of beta secretases, inhibitors of gamma secretases, inhibitors of neutral endopeptidase, inhibitors of Phosphodiesterase-4 (PDE-4), tumor necrosis factor (TNF) alpha inhibitors, muscarinic M1 receptor antagonists, N-methyl-D-aspartic acid (NMDA) receptor antagonists, sigma-1 receptor inhibitors, histamine H3 antagonists, immunomodulatory agents, immunosuppressive agents, beta-amyloid antibodies, cysteine protease inhibitors, Monocyte chemoattractant protein-1 (MOP-1) antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

23. A process for preparation of a compound according to claim 1 comprising:

reacting a compound of formula (II)

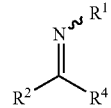
(II)

with a suitable azide such as trimethylsilylazide and a compound of formula (III)

(III)

wherein $R^1$, $R^2$, $R^3$, and $R^4$ are as defined in claim 1.

* * * * *